US012319737B2

(12) United States Patent
Miller et al.

(10) Patent No.: US 12,319,737 B2
(45) Date of Patent: Jun. 3, 2025

(54) NK ENGAGER MOLECULES AND METHODS OF USE THEREOF

(71) Applicant: Regents of the University of Minnesota, Minneapolis, MN (US)

(72) Inventors: Jeffrey S. Miller, Minneapolis, MN (US); Martin Felices, Minneapolis, MN (US); Daniel A. Vallera, Minneapolis, MN (US); Todd R. Lenvik, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1044 days.

(21) Appl. No.: 17/285,447

(22) PCT Filed: Oct. 17, 2019

(86) PCT No.: PCT/US2019/056777
§ 371 (c)(1),
(2) Date: Apr. 14, 2021

(87) PCT Pub. No.: WO2020/081841
PCT Pub. Date: Apr. 23, 2020

(65) Prior Publication Data
US 2021/0388093 A1    Dec. 16, 2021

Related U.S. Application Data

(60) Provisional application No. 62/747,983, filed on Oct. 19, 2018.

(51) Int. Cl.
*A61P 35/00* (2006.01)
*C07K 16/28* (2006.01)
*C07K 16/30* (2006.01)
*A61K 39/00* (2006.01)

(52) U.S. Cl.
CPC .......... *C07K 16/2851* (2013.01); *A61P 35/00* (2018.01); *C07K 16/283* (2013.01); *C07K 16/30* (2013.01); *A61K 2039/505* (2013.01); *C07K 2317/22* (2013.01); *C07K 2317/24* (2013.01); *C07K 2317/622* (2013.01)

(58) Field of Classification Search
CPC .................................................. C07K 16/2851
USPC ..................................................... 424/133.1
See application file for complete search history.

(56) References Cited

U.S. PATENT DOCUMENTS

| | | | |
|---|---|---|---|
| 9,090,876 | B2 | 7/2015 | Velardi et al. |
| 9,155,798 | B2 | 10/2015 | Vallera |
| 10,501,545 | B2 | 12/2019 | Kelley et al. |
| 2006/0104971 | A1 | 5/2006 | Garber et al. |
| 2006/0134102 | A1 | 6/2006 | Lepage et al. |
| 2010/0055724 | A1 | 3/2010 | Taylor et al. |
| 2012/0014957 | A1 | 1/2012 | Ghayur et al. |
| 2012/0315282 | A1 | 12/2012 | Bedinger et al. |
| 2014/0242025 | A1 | 8/2014 | Wong et al. |
| 2014/0378664 | A1 | 12/2014 | Suh et al. |
| 2016/0368994 | A1 | 12/2016 | Kelley et al. |
| 2018/0282386 | A1 | 10/2018 | Vallera et al. |
| 2020/0087369 | A1 | 3/2020 | Vallera et al. |
| 2020/0148737 | A1 | 5/2020 | Vallera et al. |

FOREIGN PATENT DOCUMENTS

| | | |
|---|---|---|
| EP | 2332994 A1 | 6/2011 |
| JP | 2010-500967 A | 1/2010 |
| JP | 2010-517048 A | 5/2010 |
| JP | 2012-100677 A | 5/2012 |
| JP | 2013-513370 A | 4/2013 |
| JP | 2013-535187 A | 9/2013 |
| JP | 2014-507150 A | 3/2014 |
| JP | 2014-518064 A | 7/2014 |
| JP | 2015-532278 A | 11/2015 |
| JP | 2018-502114 A | 1/2018 |
| JP | 2020-534269 A | 11/2020 |
| RU | 2014100350 A | 7/2015 |
| RU | 2644671 C2 | 2/2018 |
| WO | WO 2005/000894 A3 | 1/2005 |
| WO | 2005/089788 A1 | 9/2005 |
| WO | 2006/099141 A2 | 9/2006 |
| WO | 2008/011157 A2 | 1/2008 |
| WO | 2008/092164 A2 | 7/2008 |
| WO | WO 2009/007124 A1 | 1/2009 |
| WO | 2009/029601 A2 | 3/2009 |
| WO | 2011/070109 A1 | 6/2011 |
| WO | 2012/006490 A2 | 1/2012 |
| WO | 2012/017522 A1 | 2/2012 |
| WO | 2012/040323 A2 | 3/2012 |

(Continued)

OTHER PUBLICATIONS

Montrose-Rafizadeh (The Journal of Biological Chemistry, vol. 272, p. 21201-21206, 1997) (Year: 1997).*
Nonaka (Human Molecular Genetics, vol. 18, No. 18, p. 3353-3364, 2009) (Year: 2009).*
Martindale (Nature Genetics, vol. 18, p. 150-154, 1998) (Year: 1998).*
Huang (The Journal of Biological Chemistry, vol. 272, No. 43, p. 27155-27159, 1997) (Year: 1997).*
Ju (Proceedings of the National Academy of Sciences, U.S.A., vol. 88, p. 2658-2662, 1991) (Year: 1991).*

(Continued)

*Primary Examiner* — Sean E Aeder
(74) *Attorney, Agent, or Firm* — DLA Piper LLP (US)

(57) ABSTRACT

Provided are compositions for activating NK cells to stimulate an immune response for treating cancer and other disorders. In one embodiment, the invention provides a compound comprising an NK engaging domain that binds to CD 16; an NK activating domain operably linked to the NK engaging domain; and a targeting domain that selectively binds to a target cell and is operably linked to the NK activating domain and the NK engaging domain, wherein the targeting domain binds to CLEC12A.

14 Claims, 38 Drawing Sheets

Specification includes a Sequence Listing.

(56) References Cited

FOREIGN PATENT DOCUMENTS

| WO | 2012/113266 A1 | 8/2012 |
|---|---|---|
| WO | 2012/167143 A1 | 12/2012 |
| WO | 2013/039883 A1 | 3/2013 |
| WO | 2013/163427 A1 | 10/2013 |
| WO | 2014/138306 A1 | 9/2014 |
| WO | 2015/090229 A1 | 6/2015 |
| WO | WO 2016/014535 A1 | 1/2016 |
| WO | WO 2016/205200 A1 | 12/2016 |
| WO | WO 2017/062604 A1 | 4/2017 |
| WO | WO 2017/125897 A1 | 7/2017 |
| WO | WO 2019/055677 A1 | 3/2019 |
| WO | WO 2019/246593 A2 * | 12/2019 |

OTHER PUBLICATIONS

Lazar et al. Molecular and Cellular Biology 8:1247-1252, 1988). (Year: 1988).*
Burgess et al., J of Cell Bio. 111:2129-2138, 1990). (Year: 1990).*
Baxevanis (Expert Opinion: Drug Discovery, vol. 3, No. 4, p. 441-452, 2008) (Year: 2008).*
Mendoza et al. Arch. Immunol. Therap. Exp., 2005, vol. 53, pp. 47-60.*
Van Den Ouden-Rijn, 2005, WIPO DOcument, PDF WO 2005/000894 A2.*
Baker et al. Immunity, Oct. 2000, vol. 13, pp. 475-484.*
Kelly et al., 2016, WIPO document, PDF WO2016/205200 A1.*
Trzpis, "Epithelial cell adhesion molecule: more than a carcinoma marker and adhesion molecule" 2007 Am J Pathol., 171(2):386-95.
Vallera, "Genetic alteration of a bispecific ligand-directed toxin targeting human CD19 and CD22 receptors resulting in improved efficacy against systemic B cell malignancy" 2009 Leuk Res., 33:1233-42.
Vallera, "Heterodimeric bispecific single-chain variable-fragment antibodies against EpCAM and CD16 induce effective antibody-dependent cellular cytotoxicity against human carcinoma cells" 2013 Cancer Biother Radiopharm., (4):274-82.
Vallera, "Molecular modification of a recombinant, bivalent anti-human CD3 immunotoxin (Bic3) results in reduced in vivo toxicity in mice" 2005 Leuk Res., 29:331-41.
Verneris, "Mismatch Is Associated with Worse Outcomes after Unrelated Donor Reduced-Intensity Conditioning Hematopoietic Cell Transplantation: An Analysis from the Center for International Blood and Marrow Transplant Research" 2015 Biol Blood Marrow Transplant, 21:1783-9.
Vincke, "General strategy to humanize a camelid single-domain antibody and identification of a universal humanized nanobody scaffold" 2009 J Biol Chem., 284(5):3273-3284.
Waldmann, "Interleukin-15 in the treatment of cancer" 2014 Expert Rev Clin Immunol., 10:1689-701.
Waldron, "Targeting tumor-initiating cancer cells with dCD133KDEL shows impressive tumor reductions in a xenotransplant model of human head and neck cancer" 2011 Mal Cancer Ther., 10:1829-38.
Weskamp, "Pathological neovascularization is reduced by inactivation of ADAMI 7 in endothelial cells but not in pericytes" Mar. 2010 Circ Res., (5): 932-40.
Wiernik, "Targeting natural killer cells to acute myeloid leukemia in vitro with a CD16×33 bispecific killer cell engager and ADAMI 7 inhibition" 2013 Clin Cancer Res., (14): 3844-55.
Wu, "Expression of interleukin 15 in primary adult acute lymphoblastic leukemia" 2010 Cancer, (116):387-92.
Yamamoto, "Circulating CD4+CD25+ regulatory T cells in patients with pancreatic cancer" 2012 Pancreas, 41(3):409-15. doi: 10.1097/MPA.0b013e3182373a66.
Yokoyama, "Immune functions encoded by the natural killer gene complex" 2003 Nat Rev Immunol., (4):304-16.
Zambello, "Interleukin-15 triggers the proliferation and cytotoxicity of granular lymphocytes in patients with lymphoproliferative disease of granular lymphocytes" 1997 Blood, (89): 201-11.
Ko, "Safety, pharmacokinetics, and biological pharmacodynamics of the immunocytokine EMD 273066 (huKS-IL2): results of a phase I trial in patients with prostate cancer" 2004 J Immunother., 27(3):232-9.
Kuniyasu, "Interleukin-15 expression is associated with malignant potential in colon cancer cells" 2001 Pathobiology, (69):86-95.
Kuniyasu, "Production of interleukin 15 by human colon cancer cells is associated with induction of mucosal hyperplasia, angiogenesis, and metastasis" 2003 Clin Cancer Res., 9(13):4802-10.
Lanier, "Functional and biochemical analysis of CD16 antigen on natural killer cells and granulocytes" 1988 J Immunol., 141: 3478-85.
Lanier, "Natural killer cell receptor signaling" 2003 Curr Opin Immunol., (3):308-14.
Lanier, "The relationship of CD16 (Leu-11) and Leu-19 (NKH-1) antigen expression on human peripheral blood NK cells and cytotoxic T lymphocytes" 1986 J Immunol., 136(12):4480-6.
Lin, "The role of shared receptor motifs and common Stat proteins in the generation of cytokine pleiotropy and redundancy by IL-2, IL-4, IL-7, IL-13, and IL-15" 1995 Immunity, 2: 331-9.
M. K. Gleason et al: "Bispecific and Trispecific Killer Cell Engagers Directly Activate Human NK Cells through CD16 Signaling and Induce Cytotoxicity and Cytokine Production", Molecular Cancer Therapeutics, vol. 11, No. 12, Dec. 1, 2012 (Dec. 1, 2012), pp. 2674-2684.
Ma, "Myelodysplastic syndromes: incidence and survival in the United States" 2007 Cancer, (8): 1536-1542.
Maretzky, "A transforming Src mutant increases the bioavailability of EGFR ligands via stimulation of the cell-surface metalloproteinase ADAMI 7" 2011 Oncogene, (5): 611-8.
Martin Feli Ces et al: "CD16-IL15-CD33 Trispecific Killer Engager (TrikE) induces NK cell expansion, persistence, and myeloid blast antigen specific killing.", The Journal of Immunology, vol. 196 (1 Supplement), May 1, 2016 (May 1, 2016), p. 75.8.
McCall, "Isolation and characterization of an anti-CD16 single-chain Fv fragment and construction of an anti-HER2/neu/anti-CD16 bispecific scFv that triggers CD16-dependent tumor cytolysis" 1999 Mal Immunol., (7): 433-445.
Michelle K Gleason et al: "CD16×CD33 bispecific killer cell engager (BiKE) activates NK cells against primary MOS and MDSC CD33 1 targets", Blood, vol. 123, No. 19, May 8, 2014 (May 8, 2014), pp. 3016-3026.
Miller, "Expansion and homing of adoptively transferred human natural killer cells in immunodeficient mice varies with product preparation and in vivo cytokine administration: implications for clinical therapy" 2014 Biol Blood Marrow Transplant, 20:1252-7.
Miller, "Successful adoptive transfer and in vivo expansion of human haploidentical NK cells in patients with cancer" 2005 Blood, 105:3051-7.
Miller, "Therapeutic applications: natural killer cells in the clinic," Hematology Am Soc Hematol Educ Program. 2013; 2013(1):247-253.
Miller, "Trispecific Killer Engagers (TrikEs) that contain IL-15 to make NK cells antigen specific and to sustain their persistence and expansion" Dec. 2015 Blood, pp. 1-4.
Mishra, "Molecular pathways: Interleukin-15 signaling in health and cancer" 2014 Clin Cancer Res., 20: 2044-50.
Munger, "Studies evaluating the antitumor activity and toxicity of interleukin-15, a new T cell growth factor: comparison with interleukin-2" 1995 Cell Immunol., 165(2):289-93.
Munz, "The carcinoma-associated antigen EpCAM upregulates c-myc and induces cell proliferation" 2004 Oncogene, 23(34):5748-58.
Munz, "The emerging role of EpCAM in cancer and stem cell signaling" 2009 Cancer Res., 69(14):5627-9.
National Center for Biotechnology Information, National Library of Medicine, National Institutes of Health, Accession No. EF561292l, "Lama glama clone C21 immunoglobulin heavy chain variable region mRNA, partial eds," [online]. Bethesda, MD [retrieved on Apr. 4, 2019]. Retrieved from the Internet: https://www.ncbi.nlm.nih.gov/nuccore/EF561291. 1; 3 pgs.
NCCN. "NCCN Clinical Practice Guidelines in Oncology (NCCN Guidelines) Myelodysplastic Syndromes Version 2. 2014" 2013.
Ochoa, "Interleukin-15 in gene therapy of cancer" 2013 Curr Gene Ther.,13: 15-30.

(56) References Cited

OTHER PUBLICATIONS

Office Action and Search Report, dated Nov. 3, 2020, for Russian Patent Application No. 2018116565, including English translation, 20 pages.
Office Action and Search Report, dated Sep. 8, 2020, for Japanese Patent Application No. 2018-517586, 5 pages.
Office Action received for European Application No. 16854310.6, mailed on Apr. 1, 2020, 7 page.
Office Action received for European Application No. 16854310.6, mailed on Mar. 9, 2021, 8 pages.
Office Action received for European Application No. 16854310.6, mailed on Sep. 29, 2020, 8 pages.
Osenga, "A phase I clinical trial of the hu 14.18-IL2 (EMD 273063) as a treatment for children with refractory or recurrent neuroblastoma and melanoma: a study of the Children's Oncology Group" 2006 Clin Cancer Res., 12(6):1750-9.
Papadakis, "Tl1a synergizes with IL-12 and IL-18 to enhance IFN-gamma production in human T cells and NK cells" 2004 J Immunol., 172(11):7002-7.
Partial Supplementary European Search Report and Search Opinion Received for EP Application No. 16854310.6, mailed on Mar. 27, 2019, 15 pages.
Petrelli, "Regression of liver metastases after treatment with intraperitoneal catumaxomab for malignant ascites due to breast cancer" 2013 Target Oncol., 8(4):291-4. doi:10.1007/s11523-012-0240-y.
Pinz, "Preclinical targeting of human T cell malignancies using CD4-specific chimeric antigen receptor (CAR)-engineered T cells" 2015 Leukemia, 30(3):701-7. doi: 10.1038/leu.2015.311, Epub Nov. 3, 2015.
Ranson, "IL-15 is an essential mediator of peripheral NK-cell homeostasis" 2003 Blood, 101(12):4887-93.
Richards, "Anti-tumour effects of a specific anti-ADAM17 antibody in an ovarian cancer model in vivo" 2012 PLoS One, (7):e40597.
Rudikoff et al. "Single amino acid substitution altering antigen-binding specificity," Proc. Natl. Acad. Sci. USA, 1982, 79(6): 1979-1983.
Russian Office Action, dated Feb. 25, 2021, for Russian patent application No. 2018116565, 5 pages.
Schmohl, "Enhanced ADCC and NK Cell Activation of an Anticarcinoma Bispecific Antibody by Genetic Insertion of a Modified IL-15 Cross-linker" Jul. 2016 Amer Society of Gene Cell Ther., 24(7):1312-22. doi: 10.1038/mt.2016.88.
Schmohl, "Heterodimeric bispecific single chain variable fragments (scFv) killer engagers (BiKEs) enhance NK-cell activity against CD133+ colorectal cancer cells" Jun. 2016 Target Oncol., 11(3):353-361.
Schmohl, "Improvement in ADCC and NK cell activation of an anti-carcinoma bispecific antibody by genetic insertion of a modified IL-15 cross-linker" 2016 Oncal. Res. Treatm., 39:280-280.
Seimetz, "Development and approval of the trifunctional antibody catumaxomab (anti-EpCAM×anti-CD3) as a targeted cancer immunotherapy" 2010 Cancer Treat Rev., 36(6):458-67. doi:10.1016/j.ctrv.2010.03.001.
Shanmugham, "IL-15 an immunoregulatory and anti-cancer cytokine. Recent advances" 2006 J Exp Clin Cancer Res., 25:529-36.
Singer, "Effective elimination of acute myeloid leukemic cells by recombinant bispecific antibody derivatives directed against CD33 and CD16" Jul.-Aug. 2010 J Immunother., 33:599-610 (2010).
Spizzo, "High Ep-CAM expression is associated with poor prognosis in node-positive breast cancer" 2004 Breast Cancer Res Treat., 86(3):207-13.
Steel, "Interleukin-15 biology and its therapeutic implications in cancer" 2012 Trends Pharmacol Sci., 33: 35-41.
Stein, "Novel conjugates of single-chain Fv antibody fragments specific for stem cell antigen CD123 mediate potent death of acute myeloid leukaemia cells" 2010 Br J Haematol., 148;879-885.
Strohlein, "Immunotherapy of peritoneal carcinomatosis with the antibody catumaxomab in colon, gastric, or pancreatic cancer: an open-label, multicenter, phase I/II trial" 2011 Onkologie., 34(3):101-8. doi:10.1159/000324667.
Supplementary European Search Report and Search Opinion Received for EP Application No. 16854310.6, mailed on Jul. 5, 2019, 14 pages.
Trentin, "Interleukin-15 promotes the growth of leukemic cells of patients with B-cell chronic lymphoproliferative disorders" 1996 Blood, 87(8):3327-35.
Dirks, "Brain Tumor Stem Cells: Bringing Order to the Chaos of Brain Cancer", Journal of Clinical Oncology, 2008, 26(17): 2916-2924.
JP Office Action in Japanese Application No. 2021-521098, dated Sep. 28, 2023, 13 pages (with English translation).
Lopez-Lazaro, "The migration ability of stem cells can explain the existence of cancer of unknown primary site. Rethinking metastasis", Oncoscience, May 2015, 2(5):467-475.
RU Office Action in Russian Application No. 2021113936, dated Jul. 20, 2023, 13 pages (With English translation).
Sagar et al., "Antibody blockade of CLEC12A delays EAE onset and attenuates disease severity by impairing myeloid cell CNS infiltration and restoring positive immunity", Scientific Reports, Jun. 2017, 7:2707, 16 pages.
Tran et al., "Survival comparison between glioblastoma multiforme and other incurable cancers", Journal of Clinical Neuroscience, Apr. 2010, 17(4):417-421.
Wang et al., "Silence of MCL-1 upstream signaling by shRNA abrogates multiple myeloma growth", Experimental Hematology & Oncology, 2014, 3(1): 1-7.
EP Extended Search Report in European Application No. 19873982, dated Oct. 10, 2022, 9 pages.
Sunil et al., "CD16-IL15-CLEC12A Trispecific Killer Engager (Trike) Drives NK Cell Expansion, Activation, and Antigen Specific Killing of Cancer Stem Cells in Acute Myeloid Leukemia", Blood, American Society of Hematology, Nov. 2018, 132:1454.
Alderson, "Clinical cancer therapy by NK cells via antibody-dependent cell-mediated cytotoxicity" 2011 Journal of biomedicine & biotechnology, 2011:379123.
Almagro et al., "Humanization of Antibodies," Frontiers in Bioscience, 2008; 13:1619-1633.
American Type Culture Collection, "ATCC HL-60, CCl-240, a CD33+ human acute promyelocytic leukemia cell line," organism: *Homo sapiens*, human; [online] Manassas, VA [retrieved on Apr. 4, 2019 from the Internet: https://www.atcc.org/~/ps/CCL-240.ashx. 3 pgs.
American Type Culture Collection, "HT29, ATCC HTB38," organism: *Homo sapiens*, human; [online] Manassas, VA [retrieved on Apr. 4, 2019] from the Internet: https://www.ncbi.nlm.nih.gov/nuccore/EF561291.1. 3 pgs.
Artis, "The biology of innate lymphoid cells" 2015 Nature, 517:293-301.
Bachanova, "Clearance of acute myeloid leukemia by haploidentical natural killer cells is improved using IL-2 diphtheria toxin fusion protein" 2014 Blood, 123:3855-63.
Badolato, "Interleukin-15 (IL-15) induces IL-8 and monocyte chemotactic protein 1 production in human monocytes" 1997 Blood, 90: 2804-9.
Baeuerle, "EpCAM (CD326) finding its role in cancer" 2007 Br J Cancer, 96(3):417-23.
Bargou, "Tumor regression in cancer patients by very low doses of a T cell-engaging antibody" 2008 Science, 321(5891):974-7.
Barrett, "Toxicity management for patients receiving novel T-cell engaging therapies" 2014 Curr Opin Pediatr., 26(1):43-9.
Basak, "Interleukin 15 augments antitumor activity of cytokine gene-modified melanoma cell vaccines in a murine model" 2008 Oncol Rep., 19(5):1173-9.
Becknell, "Interleukin-2, interleukin-15, and their roles in human natural killer cells" 2005 Adv Immunol., 86: 209-39.
Bell, "Sustained in vivo signaling by long-lived IL-2 induces prolonged increases of regulatory T cells" 2015 J Autoimmun., 56:66-80.

(56) References Cited

OTHER PUBLICATIONS

Berger, "Safety and immunologic effects of IL-15 administration in nonhuman primates" 2009 Blood, (12): 2417-2426.
Bezan, "Systemic effect of catumaxomab in a patient with metastasized colorectal cancer: a case report" 2013 BMC Cancer, 13:618. doi:10.1186/1471-2407-13-618.
Budagian, "IL-15/IL-15 receptor biology: a guided tour through an expanding universe" 2006 Cytokine Growth Factor Rev., 17: 259-80.
Budagian, "Reverse signaling through membrane-bound interleukin-15" 2004 J Biol Chem., 279: 42192-2.
Caligiuri, "Functional consequences of interleukin 2 receptor expression on resting human lymphocytes. Identification of a novel natural killer cell subset with high affinity receptors" 1990 J ExpMed., 171(5):1509-26.
Carson, "Interleukin (IL) 15 is a novel cytokine that activates human natural killer cells via components of the IL-2 receptor" 1994 J Exp Med., 180(4): 1395-403.
Chen et al., "Enhancement and destruction of antibody function by somatic mutation: unequal occurrence is controlled by V gene combinatorial associations," EMBO Journal, 1995, 14(12): 2784-2794.
Colman, "Effects of amino acid sequence changes on antibody-antigen interactions," Research in Immunology, 1994, 145:33-36.
Conlon, "Redistribution, hyperproliferation, activation of natural killer cells and CD8 T cells, and cytokine production during first-in-human clinical trial of recombinant human interleukin-15 in patients with cancer" 2015 J Clin Oncol., 33(1):74-82.
Connor, "Ex vivo evaluation of anti-EpCAM immunocytokine huKS-IL2 in ovarian cancer" 2004 J Immunother., 27(3):211-9.
Cooper, "Human natural killer cells: a unique innate immunoregulatory role for the CD56(bright) subset" 2001 Blood, 97(10):3146-51.
D. A. Vallera et al: "IL15 Trispecific Killer Engagers (TriKE) Make Natural Killer Cells Specific to CD33+ Targets While Also Inducing Persistence, In Vivo Expansion, and Enhanced Function", Clinical Cancer Research, vol. 22, No. 14, Feb. 4, 2016 (Feb. 4, 2016), pp. 3440-3450.
Ensinger, "EpCAM overexpression in thyroid carcinomas: a histopathological study of 121 cases" 2006 J Immunother., 29(5):569-73.
Fehniger, "Differential cytokine and chemokine gene expression by human NK cells following activation with IL-18 or IL-15 in combination with IL-12: implications for the innate immune response" 1999 J Immunol., 162(8):4511-20.
Fehniger, "Fatal leukemia in interleukin 15 transgenic mice follows early expansions in natural killer and memory phenotype CD8+ T cells" 2001 J Exp Med., (193): 219-31.
Felices et al., "Generation of BiKEs and TriKEs to improve NK cell-mediated targeting of tumor cells," Methods Mal Biol., 2016; 1441:333-346.
Finco, "Cytokine release assays: current practices and future directions" 2014 Cytokine, 66(2):143-55. doi: 10.1016/j.cyto.2013.12.009. Epub Jan. 10, 2014. Review.
Finney, "Activation of resting human primary T cells with chimeric receptors: costimulation from CD28, inducible costimulator, CD134, and CD137 in series with signals from the TCR zeta chain" 2004 J Immunol., 172(1):104-13.

Fogh, "One hundred and twenty-seven cultured human tumor cell lines producing tumors in nude mice" 1977 J Natl Cancer Inst., 59(1):221-6.
Foley, "NK cell education after allogeneic transplantation: dissociation between recovery of cytokine-producing and cytotoxic functions" 2011 Blood, 118:2784-92.
Foley, "The biology of NK cells and their receptors affects clinical outcomes after hematopoietic cell transplantation (HCT)" 2014 Immunol Rev., 258:45-63.
Gastl, "Ep-CAM overexpression in breast cancer as a predictor of survival" 2000 Lancet, 356(9246):1981-2.
Gleason, "The Functional Role of the Activating Receptors Tim-3 and Cdl6 in Human Natural Killer (NK) Cell Biology" dissertation University of Minnesota, Sep. 2012. 199 pages.
Grupp, "Chimeric antigen receptor-modified T cells for acute lymphoid leukemia" 2013 N Engl J Med., 368(16):1509-18.
Gutzmer, "A tumor-associated glycoprotein that blocks MHC class II-dependent antigen presentation by dendritic cells" 2004 J Immunol., 173(2):1023-32.
Heiss, "The trifunctional antibody catumaxomab for the treatment of malignant ascites due to epithelial cancer: Results of a prospective randomized phase 11/111 trial" 2010 Int J Cancer, 127(9):2209-21.
Hodge, "Interleukin-15 enhances proteasomal degradation of bid in normal lymphocytes: implications for large granular lymphocyte leukemias" 2009 Cancer Res., 69(9):3986-94.
Huntington, "IL-15 trans-presentation promotes human NK cell development and differentiation in vivo" 2009 J Exp Med., 206(1):25-34.
Imai, "Chimeric receptors with 4-1BB signaling capacity provoke potent cytotoxicity against acute lymphoblastic leukemia" 2004 Leukemia, 18(4):676-84.
International Preliminary Report on Patentability received for PCT Patent Application No. PCT/US2016/055722, mailed on Apr. 19, 2018, 8 pages.
International Preliminary Report on Patentability received for PCT Patent Application No. PCT/US2019/056777, mailed on Apr. 29, 2021, 8 pages.
International Search Report and Written Opinion received for PCT Patent Application No. PCT/US2016/055722, mailed on Feb. 17, 2017, 11 pages.
International Search Report and Written Opinion received for PCT Patent Application No. PCT/US2019/056777, mailed on Mar. 18, 2020, 12 pages.
Jakobisiak, "Interleukin 15 as a promising candidate for tumor immunotherapy" 2011 Cytokine Growth Factor Rev., 22: 99-108.
Khawam, "Human renal cancer cells express a novel membrane-bound interleukin-15 that induces, in response to the soluble interleukin-15 receptor alpha chain, epithelial-to-mesenchymal transition" 2009 Cancer Res., 69(4):1561-9.
King, "Phase I clinical trial of the immunocytokine EMD 273063 in melanoma patients" 2004 J Clin Oncol., 22(22):4463-73.
Klein, "Surface IgM-kappa specificity on a Burkitt lymphoma cell in vivo and in derived culture lines" 1968 Cancer Res., 28(7):1300-10.

* cited by examiner

NK ENGAGER MOLECULES AND METHODS OF USE THEREOF

CROSS-REFERENCE TO RELATED APPLICATIONS

This application is a 35 USC § 371 National Stage application of International Application No. PCT/US2019/056777 filed Oct. 17, 2019, now pending; which claims the benefit under 35 USC § 119 (e) to U.S. Application Ser. No. 62/747,983 filed Oct. 19, 2018, now expired. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under CA111412, CA065493, CA036725, CA072669, CA077598, and CA197292 awarded by the National Institutes of Health. The government has certain rights in the invention. This invention was made with government support under W81XWH-16-1-0380 awarded by The Department of the United States Army. The government has certain rights in the invention

SEQUENCE LISTING

The material in the accompanying sequence listing is hereby incorporated by reference into this application. The accompanying sequence listing text file, name GTBIO2090_1WO_Sequence_Listing.txt, was created on Oct. 15, 2019, and is 23 kb. The file can be accessed using Microsoft Word on a computer that uses Windows OS.

BACKGROUND OF THE INVENTION

Field of the Invention

The invention relates generally to immunotherapy and more specifically to compositions useful for engaging natural killer (NK) cells in an immune response.

Background Information

Natural killer (NK) cells are cytotoxic lymphocytes of the innate immune system capable of immune surveillance. Like cytotoxic T cells, NK cells deliver a store of membrane penetrating and apoptosis-inducing granzyme and perforin granules. Unlike T cells, NK cells do not require antigen priming and recognize targets by engaging activating receptors in the absence of MHC recognition. NK cells express CD16, an activation receptor that binds to the Fc portion of IgG antibodies and is involved in antibody-dependent cell-mediated cytotoxicity (ADCC). NK cells are regulated by IL-15, which can induce increased antigen-dependent cytotoxicity, lymphokine-activated killer activity, and/or mediate interferon (IFN), tumor-necrosis factor (TNF) and/or granulocyte-macrophage colony-stimulating factor (GM-CSF) responses. All of these IL-15-activated functions contribute to improved cancer defense.

Therapeutically, adoptive transfer of NK cells can, for example, induce remission in patients with refractory acute myeloid leukemia (AML) when combined with lymphodepleting chemotherapy and IL-2 to stimulate survival and in vivo expansion of NK cells. This therapy can be limited by lack of antigen specificity and IL-2-mediated induction of regulatory T (Treg) cells that suppress NK cell proliferation and function. Generating a reagent that drives NK cell antigen specificity, expansion, and/or persistence, while bypassing the negative effects of Treg inhibition, can enhance NK-cell-based immunotherapies.

SUMMARY OF THE INVENTION

The present invention relates to compounds and compositions for activating NK cells to stimulate an immune response for treating cancer and other disorders. In one embodiment, the invention provides a compound including an NK engaging domain; an NK activating domain operably linked to the NK engaging domain; and a targeting domain that selectively binds to a target cell and is operably linked to the NK activating domain and the NK engaging domain, wherein the targeting domain selectively binds to CLEC12A.

In some embodiments, the NK engaging domain includes a moiety that selectively binds to CD16. In some embodiments, the NK engaging domain moiety includes an antibody or a binding fragment thereof or a nanobody, also known as single domain antibody (sdAb or VHH). In some embodiments, the antibody binding fragment includes an scFv, a F(ab)2, or a Fab. In some embodiments, the antibody or a binding fragment thereof or the nanobody is human or humanized. In some embodiments, the antibody or a binding fragment thereof or the nanobody is camelid.

In some embodiments, the NK activating domain includes a cytokine or functional fragment thereof. In some embodiments, the NK activating domain includes IL-15 or a functional fragment thereof. In some embodiments, the IL-15 includes the amino acid sequence of SEQ ID NO:9 or a functional variant thereof. In one aspect, the functional variant of IL-15 includes an N72D or N72A amino acid substitution compared to SEQ ID NO:9.

In some embodiments, the targeting domain moiety includes an antibody or a binding fragment thereof or a nanobody. In some embodiments, the antibody binding fragment includes an scFv, a F(ab)2, or a Fab.

In some embodiments, the NK engaging domain includes a moiety that selectively binds to CD16, the NK activating domain includes IL-15, and the targeting domain selectively binds to CLEC12A.

In some embodiments, the compounds and compositions described herein include at least one flanking sequence linking two of the domains. In some embodiments, the compounds and compositions described herein further include a second flanking sequence linking the two linked domains with a third domain. In some embodiments, the flanking sequences flank the NK activating domain. In some embodiments, a first flanking sequence is C-terminal to the NK engaging domain and a second flanking sequence is N-terminal to the anti-CLEC12A targeting domain.

In some embodiments, provided herein is an isolated amino acid sequence including SEQ ID NO.: 1. In some embodiments, provided herein is an isolated DNA sequence encoding the amino acid sequence of SEQ ID NO.: 1.

In some embodiments, provided herein is an isolated amino acid sequence including SEQ ID NO.: 2. In some embodiments, provided herein is an isolated DNA sequence encoding the amino acid sequence of SEQ ID NO.: 2.

In some embodiments, provided herein is an isolated amino acid sequence including SEQ ID NO.: 4. In some embodiments, provided herein is an isolated DNA sequence encoding the amino acid sequence of SEQ ID NO.: 4.

In some embodiments, provided herein are compositions including the compounds described herein and a pharmaceutically acceptable carrier.

In some embodiments, provided herein are methods including: administering to a subject a compound described herein in an amount effective to induce NK-mediated killing of a target cell. In some embodiments, the target cell is a cancer cell.

In some embodiments, provided herein are methods for stimulating expansion of NK cells in vivo, the methods including: administering to a subject an amount of a compound described herein effective to stimulate expansion of NK cells in the subject.

In some embodiments, provided herein are methods of treating cancer in a subject, the methods including: administering to the subject an amount of a compound described herein effective for treating the cancer. In some embodiments, the cancer includes prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, or hematopoietic cancer. In some embodiments, the methods provided herein further include administering the compound prior to, simultaneously with, or following chemotherapy, surgical resection of a tumor, or radiation therapy. In some embodiments, the chemotherapy includes altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine. In some embodiments, the hematopoietic cancer is AML.

DETAILED DESCRIPTION OF THE INVENTION

Figure 1A:
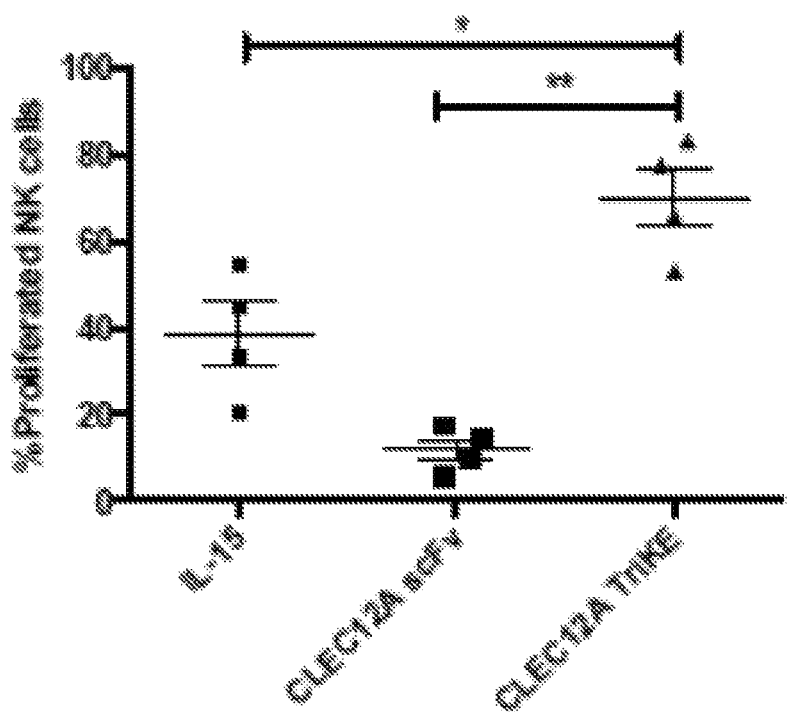
FIGS. 1A-1C illustrate NK cell proliferation (FIG. 1A), NK cell killing (FIG. 1B), and functional assays (FIG. 1C) upon treatment with CLEC12A TriKE.

Natural killer (NK) cells are cytotoxic lymphocytes of the innate immune system capable of immune surveillance. Like cytotoxic T cells, NK cells deliver a store of membrane penetrating and apoptosis-inducing granzyme and perforin granules. Unlike T cells, NK cells do not require antigen priming and recognize targets by engaging activating receptors in the absence of MHC recognition. NK cells express CD16, an activation receptor that binds to the Fc portion of IgG antibodies and is involved in antibody-dependent cell-mediated cytotoxicity (ADCC). NK cells are regulated by IL-15, which can induce increased antigen-dependent cytotoxicity, lymphokine-activated killer activity, and/or mediate interferon (IFN), tumor-necrosis factor (TNF) and/or granulocyte-macrophage colony-stimulating factor (GM-CSF) responses. All of these IL-15-activated functions contribute to improved cancer defense.

Therapeutically, adoptive transfer of NK cells can, for example, induce remission in patients with refractory acute myeloid leukemia (AML) when combined with lymphodepleting chemotherapy and IL-2 to stimulate survival and in vivo expansion of NK cells. This therapy can be limited by lack of antigen specificity and IL-2-mediated induction of regulatory T (Treg) cells that suppress NK cell proliferation and function. Generating a reagent that drives NK cell antigen specificity, expansion, and/or persistence, while bypassing the negative effects of Treg inhibition, can enhance NK-cell-based immunotherapies.

This disclosure describes generating a tri-specific molecule that includes two domains capable of driving NK-cell-mediated killing of tumor cells (e.g., CD33+ and/or CD33– tumor cells) and an intramolecular NK activating domain capable of generating an NK cell self-sustaining signal. The tri-specific molecule can drive NK cell proliferation and/or enhance NK-cell-driven cytotoxicity against, for example, HL-60 targets, cancer cells, or cancer cell-derived cell lines.

The invention is based on the development of a CD16/IL-15/CD33 trispecific killer engager (TriKE) molecule to target acute myeloid leukemia (AML) cells using Natural Killer (NK) cells. This molecule contains an anti-CD16 camelid nanobody to activate NK cells, an anti-CD33 single chain variable fragment (scFv) to engage cancer targets, and an IL-15 molecule that drives NK cell priming, expansion and survival. Using an earlier version of this molecule, the CD33 TriKE was shown to be effective at activating NK cells against AML targets in vitro and in vivo. This preclinical data has led to the establishment of a clinical trial in refractory AML patients at the University of Minnesota, set to open Q3 2018. While these previous studies have validated the use of TriKEs as an effective strategy of harnessing NK cells in cancer immunotherapy, CD33 has limitations as a target antigen.

The high mortality and poor five-year survival rates (26%) for AML patients can be attributed to chemotherapy resistance and disease relapse. A majority of chemotherapy resistant leukemia stem cells (LSCs) that are hypothesized to facilitate relapse do not express CD33. In addition, all hematopoietic stem cells and normal myeloid cells express CD33, thus targeting this antigen can lead to severe defects in hematopoiesis and on-target/off-tumor toxicity. To address these limitations, described herein is the development of a TriKE that targets CLEC12A or C-type lectin-like molecule 1 (CLL-1). CLEC12A is highly expressed on AML cells and over 70% of CD33 negative cells express CLEC12A. It has been attributed as a stem cell marker in AML, being selectively overexpressed in LSCs. CLEC12A is expressed by CD34+/CD38− LSCs but not normal CD34+/CD38− hematopoietic stem cells in regenerating bone marrow, thus minimizing off-target effects. C-type lectin domain family 12 member A is a protein that in humans is encoded by the CLEC12A gene. This gene encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13.

BiKE and TriKE Compounds

Bi-specific fusions have been made that incorporate an anti-human anti-CD16 scFv derived from a human phage display library technology (McCall et al., 1999. Mol Immunol. 36:433-445). NK cells mediate antibody-dependent cell-mediated cytotoxicity (ADCC) through the CD16 (FcγRIII) receptor. Signaling through the CD16 receptor induces calcium fluxes and phosphorylation of ITAMs, triggering the release of lytic granules and cytokines such as interferon (IFNγ) and tumor necrosis factor (TNFα). A bi-specific molecule has been designed to trigger the CD16 receptor in conjunction with other targeting molecules (Gleason et al. Blood. 2014 (19):3016-26), a so-called bispecific killer engager (BiKE). With one scFv recognizing NK cells and a second scFv recognizing a tumor antigen, BiKEs can markedly enhance cytotoxic killing in various human cancers. One exemplary BiKE targeted CD33 and enhanced NK cell responses against acute myeloid leukemia (AML) and myelodyplastic syndrome (MDS). MDS is a clonal heterogeneous stem cell disorder characterized by normal or hypercellular bone marrow (BM) with peripheral blood (PB) cytopenias and an increased risk of progressing to AML.

NK cells are responsive to a variety of cytokines including, for example, IL-15, which is involved in NK cell homeostasis, proliferation, survival, activation, and/or development. For example, IL-15 can activate NK cells, and can restore functional defects in engrafting NK cells after hematopoietic stem cell transplantation (HSCT). IL-15 and IL-2 share several signaling components, including the IL-2/IL-15Rβ (CD122) and the common gamma chain (CD132). Unlike IL-2, IL-15 does not stimulate Tregs, allowing for NK cell activation while bypassing Treg inhibition of the immune response. Besides promoting NK cell homeostasis and proliferation, IL-15 can rescue NK cell functional defects that can occur in the post-transplant setting. IL-15 also can stimulate CD8+ T cell function, further enhancing its immunotherapeutic potential. In addition, based on pre-clinical studies, toxicity profiles of IL-15 may be more favorable than IL-2 at low doses. In accordance with some embodiments, the compositions described herein can be used to activate NK cells and drive NK cell priming, expansion and survival.

This disclosure describes, in one aspect, tri-specific killer engager (TriKE) molecules that generally include one or, one or more targeting domains (that target, e.g., a tumor cell or virally-infected cell), and one or more cytokine NK activating domains (e.g., IL-15, IL-12, IL-18, IL-21, or other NK cell enhancing cytokine, chemokine, and/or activating molecule), with each domain operably linked to the other domains. As used herein, the term "operably linked" refers to direct or indirect covalent linking. Thus, two domains that are operably linked may be directly covalently coupled to one another. Conversely, the two operably linked domains may be connected by mutual covalent linking to an intervening moiety (e.g., and flanking sequence). Two domains may be considered operably linked if, for example, they are separated by the third domain, with or without one or more intervening flanking sequences.

Exemplary BiKE and TriKE molecules or compounds are described in WO2017062604, the disclosure of which is incorporated herein by reference in its entirety.

This disclosure describes, in some embodiments, compounds that include an NK engaging domain; an NK activating domain operably linked to the NK engaging domain; and a targeting domain that selectively binds to a target cell and is operably linked to the NK activating domain and the NK engaging domain, wherein the targeting domain selectively binds to a target molecule. The target molecule can be expressed on the surface of a target cell, for example. The target cell can be a tumor cell, for example. In some embodiments, the targeting domain selectively binds to CLEC12A.

As used herein, the terms "selectively binding" or "selectively binds" in reference to the interaction of a binding molecule or a domain described herein, e.g., an antibody or an engaging domain, an activating domain, or a targeting domain, and its binding partner, e.g., an antigen or a receptor, means that the interaction is dependent upon the presence of a particular structure, e.g., an antigenic determinant or epitope or amino acid sequence, on the binding partner. In other words, the binding molecule or domain preferentially binds or recognizes the binding partner even when the binding partner is present in a mixture of other molecules. The binding may be mediated by covalent or non-covalent interactions or a combination of both. The terms "selectively binding" or "selectively binds" and "specifically binding" or "specifically binds" may be used interchangeably.

The compounds described herein can possess or lack a His tag. A His tag allows for purification of a protein and can be useful in research applications, for example. The His tag may be placed at the C-terminus or at the N-terminus of the compounds or molecules described herein and may include a spacer N-terminal or C-terminal to the His tag. As an example, a His tag that is placed at the C-terminus of a compound or molecule described herein can include a spacer N-terminal to the His tag. As another example, a His tag that is placed at the N-terminus of a compound or molecule described herein can include a spacer C-terminal to the His tag. An exemplary His tag with spacer is SEQ ID NO:3. SEQ ID NO:3 can be placed at the C-terminus of the compounds described herein. A person skilled in the art will appreciate that any number of His repeats can constitute a His tag and that any spacer sequence of any length or no spacer can be used.

In some embodiments, the TriKE compound or molecule that selectively binds to CLEC12A includes the isolated amino acid sequence of SEQ ID NO:1. In some embodiments, the TriKE compound or molecule that selectively binds to CLEC12A includes the isolated amino acid sequence of SEQ ID NO:2. In some embodiments, the targeting domain of the compounds described herein that selectively binds to CLEC12A includes the isolated amino acid sequence of SEQ ID NO:4.

Also described herein are nucleic acid sequences that encode the sequences of SEQ ID NO:1, SEQ ID NO:2, and SEQ ID NO:4. For example, SEQ ID NO:1 can be encoded by SEQ ID NO:5, SEQ ID NO:2 can be encoded by SEQ ID NO:6, and SEQ ID NO:4 can be encoded by SEQ ID NO:7. A person of skill in the art will appreciate that any functional variants of the nucleic acid molecules provided herein are contemplated in the present disclosure. Functional variants are nucleic acid sequences that can be translated to provide an amino acid sequence homologous or identical to that translated from a parent molecule.

NK Engaging Domain

The NK engaging domain can include any moiety that binds to and/or activates an NK cell and/or any moiety that blocks inhibition of an NK cell. Exemplary NK cell engaging domains include a moiety that binds to, e.g., CD16, CD16+CD2, CD16+DNAM, or CD16+NKp46. In some embodiments, the engaging domain includes a moiety that selectively binds to CD16. In some embodiments, the NK engaging domain activates an NK cell. In some embodiments, the NK engaging domain blocks inhibition of an NK cell.

In some embodiments, the NK engaging domain can include an antibody that selectively binds to a component of the surface of an NK cell. In other embodiments, the NK engaging domain can include a ligand or small molecule that selectively binds to a component of the surface of an NK cell. As used herein, the term "selectively binds" refers to the ability to differentiate between two or more alternatives such as, for example, having differential affinity, to any degree, for a particular target. As used herein, "antibody" refers generally an immunoglobulin or a fragment thereof and thus encompasses a monoclonal antibody, a fragment thereof (e.g., scFv, Fab, F(ab')2, Fv or other modified forms), a combination of monoclonal antibodies and/or fragments thereof, and/or a combination of polyclonal antibodies. Thus, for brevity, reference to an antibody that selectively binds to a component of the surface of an NK cell includes any antibody fragment that exhibits the described binding character. Similarly, reference to a ligand that selectively binds to a component of the surface of an NK cell includes any fragment of the ligand that exhibits the described binding character.

In some embodiments, the NK engaging domain can selectively bind to a receptor at least partially located at the surface of an NK cell. In certain embodiments, the NK engaging domain can serve a function of binding an NK cell and thereby bring the NK into spatial proximity with a target to which the targeting domain—described in more detail below—selectively binds. In certain embodiments, however, the NK engaging domain can selectively bind to a receptor that activates the NK cell and, therefore, also possess an activating function. As described above, activation of the CD16 receptor can elicit antibody-dependent cell-mediated cytotoxicity. Thus, in certain embodiments, the NK engaging domain can include at least a portion of an anti-CD16 receptor antibody effective to selectively bind to the CD16 receptor. In other embodiments, the NK engager cell domain may interrupt mechanisms that inhibit NK cells. In such embodiments, the NK engager domain can include, for example, anti-PD1/PDL1, anti-NKG2A, anti-TIGIT, anti-killer-immunoglobulin receptor (KIR), and/or any other inhibition blocking domain.

One can design the NK engaging domain to possess a desired degree of NK selectivity and, therefore, a desired immune engaging character. For example, CD16 has been identified as Fc receptors FcγRIIIa (CD16a) and FcγRIIIb (CD16b). These receptors bind to the Fc portion of IgG antibodies that then activates the NK cell for antibody-dependent cell-mediated cytotoxicity. Anti-CD16 antibodies selectively bind to NK cells, but also can bind to neutrophils. Anti-CD16a antibodies selectively bind to NK cells, but do not bind to neutrophils. A TriKE embodiment that includes an NK engaging domain that includes an anti-CD16a antibody can bind to NK cells but not bind to neutrophils. Thus, in circumstances where one may want to engage NK cells but not engage neutrophils, one can design the NK engaging domain of the TriKE to include an anti-CD16a antibody.

While described herein in the context of various embodiments in which the NK engaging domain includes an anti-CD16 receptor scFv, the NK engaging domain can include any antibody or other ligand that selectively binds to the CD16 receptor. Moreover, the NK engaging domain can include an antibody or ligand that selectively binds to any NK cell receptor such as, for example, the cell cytotoxicity receptor 2B4, low affinity Fc receptor CD16, killer immunoglobulin like receptors (KIR), CD2, NKG2A, TIGIT, NKG2C, LIR-1, and/or DNAM-1. In one embodiment, the invention composition is a construct in operable linkage NKG2C/IL-15/CD33. It should be understood that the positioning of the moieties may be changed based on activity assays (e.g., CD33/IL-15/NKG2C).

In some embodiments, the NK engaging domain includes an antibody or a binding fragment thereof, or a nanobody. The antibody binding fragment can be an scFv, a F(ab)2, or a Fab. In some embodiments, the NK engaging domain includes a nanobody. In some embodiments, the NK cell engager can involve the use of a humanized CD16 engager derived from an animal nanobody. While an scFv has a heavy variable chain component and a light variable chain component joined by a linker, a nanobody consists of a single monomeric variable chain—i.e., a variable heavy chain or a variable light chain—that is capable of specifically engaging a target. A nanobody may be derived from an antibody of any suitable animal such as, for example, a camelid (e.g., a llama or camel) or a cartilaginous fish. A nanobody can provide superior physical stability, an ability to bind deep grooves, and increased production yields compared to larger antibody fragments.

In one exemplary embodiment, a nanobody-based NK engager molecule can involve a humanized CD16 nanobody derived from a published llama nanobody (GeneBank sequence EF561291; Behar et al., 2008. Protein Eng Des Sel. 21(1):1-10), termed EF91. Llama EF91 was initially constructed into a BiKE containing CD19 to test the ability of this CD16 engager to drive NK cell activation. It showed functionality similar to rituximab-mediated killing in a chromium release assay with Raji targets. Upon confirming functionality of the molecule, the CDRs were cloned into a humanized camelid scaffold (Vincke et al., 2009. J Biol Chem. 284(5):3273-3284) to humanize the CD16 engager, now termed HuEF91. The binding of HuEF91 is equivalent to binding observed using a standard CD16 scFv, indicating that incorporating the llama nanobody variable heavy chain into the humanized backbone has not hindered the specificity of the molecule. The use HuEF91 as an NK engager in the TriKE molecules described herein can increase drug yield, increase stability, and/or increase NK-cell-mediated ADCC efficacy.

Thus, in accordance with some embodiments, the antibody or a binding fragment thereof or the nanobody is human or humanized. In some embodiments, the antibody or a binding fragment thereof or the nanobody is camelid.

NK Activating Domain

The NK activating domain can include an amino acid sequence that activates NK cells, promotes sustaining NK cells, or otherwise promotes NK cell activity. The NK activating domain can be, or can be derived from, one or more cytokines that can activate and/or sustain NK cells. As used herein, the term "derived from" refers to an amino acid fragment of a cytokine (e.g., IL-15) that is sufficient to provide NK cell activating and/or sustaining activity. In embodiments that include more than one NK activating domain, the NK activating domains may be provided in series or in any other combination. Additionally, each cytokine-based NK activating domain can include either the full amino acid sequence of the cytokine or may be an amino acid fragment, independent of the nature of other NK activating domains included in the TriKE molecule. Exemplary cytokines on which an NK activating domain may be based include, for example, IL-15, IL-18, IL-12, and IL-21. Thus, while described in detail herein in the context of an exemplary model embodiment in which the NK activating domain is derived from IL-15, a TriKE may be designed using an NK activating domain that is, or is derived from, any suitable cytokine.

For brevity in this description, reference to an NK activating domain by identifying the cytokine on which it is based includes both the full amino acid sequence of the cytokine, any suitable amino acid fragment of the cytokine, and or a modified version of the cytokine that includes one or more amino acid substitutions. Thus, reference to an "IL-15" NK activating domain includes an NK activating domain that includes the full amino acid sequence of IL-15, an NK activating domain that includes a fragment of IL-15, or an NK activating domain such as, for example, IL-15N72D or IL-15N72A, that includes an amino acid substitution compared to the wild-type IL-15 amino acid sequence.

The use of an IL-15 NK activating domain in a TriKE can provide sustained NK cell activity—as evidenced in a mouse model showing human NK cells are dramatically elevated and cancer reduced—even after three weeks. NK cells are activated in mice to produce an array of anti-cancer factors and cytokines. Moreover, an IL-15 NK activating domain can alter the chemistry of these molecules so that they refold more easily and/or are recoverable in greater yield, thus rendering the TriKE molecules more suitable for clinical scale-up.

Thus, in some embodiments, the NK activating domain includes a cytokine or functional fragment thereof. In some embodiments, the activating domain includes IL-15 or a functional fragment thereof. In some embodiments, the IL-15 is wild-type IL-15. In some embodiments, the IL-15 is human. In some embodiments, the IL-15 is wild-type human IL-15. In some embodiments, the IL-15 comprises an amino acid sequence of SEQ ID NO:9 or a functional variant thereof. In some embodiments, the functional variant of IL-15 comprises an N72D or N72A amino acid substitution as compared to SEQ ID NO:9.

As used herein, the term "functional variant" refers to a molecule, including a binding molecule, for example, comprises a nucleotide and/or amino acid sequence that is altered by one or more nucleotides and/or amino acids compared to the nucleotide and/or amino acid sequences of the parent molecule. For a binding molecule, a functional variant is still capable of competing for binding to the binding partner with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis.

Functional variants can also include, but are not limited to, derivatives that are substantially similar in primary structural sequence, but which contain e.g., in vitro or in vivo modifications, chemical and/or biochemical, that are not found in the parent binding molecule. Such modifications include inter alia acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

Targeting Domain and Targets

The targeting domain can include any moiety that selectively binds to an intended target such as, for example, a tumor cell, a target in the cancer stroma, a target on an inhibitory cell such as myeloid derived suppressor cells that are CD33+, or a target on a virally-infected cell. Thus, a targeting domain can include, for example, an anti-tumor antibody such as rituximab (anti-CD20), afutuzumab (anti-CD20), trastuzumab (anti-HER2/neu), pertuzumab (anti-HER2/neu), labetuzumab (anti-CEA), adecatumumab (anti-EpCAM), citatuzumab bogatox (anti-EpCAM), edrecolomab (anti-EpCAM), arcitumomab (anti-CEA), bevacizumab (anti-VEGF-A), cetuximab (anti-EGFR), nimotuzumab (anti-EGFR), panitumumab (anti-EGFR), zalutumumab (anti-EGFR), gemtuzumab ozogamicin (anti-CD33), lintuzumab (anti-CD33), etaracizumab (anti-integrin $\alpha_v\beta_3$), intetumumab (anti-CD51), ipilimumab (anti-CD152), oregovomab (anti-CA-125), votumumab (anti-tumor antigen CTAA16.88), or pemtumumab (anti-MUC1), anti-CD19, anti-CD22, anti-CD133, anti-CD38 anti-mesothelin, anti-ROR1, CSPG4, SS1, or IGFR1. Any tumor marker can be targeted. In some embodiments, the targeting domain, or tumor-associated antigen targeted, can include CD133, CD20, HER2, CEA, EpCAM, VEGF-A, EGFR, CD33, integrin $\alpha V\beta 3$, CD51, CD152, CD125, CTAA16.88, MUC1, CD19, CD22, CD38, mesothelin, ROR1, CSPG4, SS1, or IGFR1, NKG2 family members, including but not limited to 2A, 2B, 2C, and the like, BCMA, APRIL, B7H3, and PSMA, by way of example.

In some embodiments, the target cell is a tumor cell. In some embodiments, the tumor cell is CD33+. In some embodiments, the tumor cell is CD33−. In some embodiments, the tumor cell is a hematopoietic cancer cell. In some embodiments, the tumor cell is a leukemic cell. In some embodiments, the leukemic cell is an acute myeloid leukemia (AML) cell. In other embodiments, the targeting domain can selectively bind to a target on a cell infected by a virus such as, for example, EBV, HBV, HCV, and/or HPV. In some embodiments, a viral target is a tumor marker or a tumor antigen. Any viral tumor marker or viral or non-viral tumor antigen can be targeted.

The targeting domain moiety can include an antibody or a binding fragment of an antibody, or a nanobody, as described above. The antibody binding fragment can comprise an scFv, a F(ab)2, or a Fab.

In certain particular embodiments, the targeting domain can include an anti-CLEC12A antibody. In other particular embodiments, a second targeting domain can be included. The second targeting domain can include a moiety that can bind to any of the targets described above. In some embodiments, the second targeting domain can selectively bind to CD33.

In some embodiments, the compounds described herein include an NK engaging domain having a moiety that selectively binds to CD16, an activating domain having IL-15, and a targeting domain that selectively binds to CLEC12A. The terms "CLEC12A Trike," "1615CLEC12A TriKe," and "CD16-IL15-CLEC12A TriKE" can be used interchangeably to refer to a TriKE that targets CLEC12A, unless the context clearly indicates otherwise.

Flanking Sequences

In some embodiments, the compounds described herein can further include a flanking sequence or linker sequence that can link two of the above-described domains. The terms "flanking sequence" and "linker sequence" can be used interchangeably, unless context clearly indicates otherwise. In some embodiments, the presence of the flanking sequence can further increase NK cell activation. Any amino acid sequence can be a flanking sequence or a linker sequence. One exemplary flanking sequence includes the 20 amino acids of SEQ ID NO:13. Another exemplary flanking sequence includes the seven amino acids of SEQ ID NO:14. Yet other exemplary flanking sequences include SEQ ID NO:11, SEQ ID NO:12, and SEQ ID NO:15. As yet another example, any number of repeats of an amino acid sequence can be a flanking sequence or a linker sequence. For example, any number of repeats of the sequence of SEQ ID NO:15 can be a flanking sequence or a linker sequence. Sequence repeats can be complete or partial, and complete or partial repeats can be at the beginning, i.e., at the N-terminus, or the end, i.e., at the C-terminus, of a flanking sequence or linker sequence. Flanking sequences can be in any orientation.

Certain embodiments (e.g., the 1615CLEC12A TriKE without a His tag, SEQ ID NO:1 or 1615CLEC12A TriKE with a His tag, SEQ ID NO:2) can include more than one flanking sequence. As one example, SEQ ID NO:1 and/or SEQ ID NO:2 include the flanking sequence of SEQ ID NO:11 to link the NK engaging domain (e.g., anti-CD16 receptor scFv) with the NK activating domain (e.g., IL-15). SEQ ID NO:1 and/or SEQ ID NO:2 also include the flanking sequence of SEQ ID NO:12 to link the NK activating domain with the targeting domain (e.g., anti-CLEC12A scFv). The flanking sequences that link the domains of the molecule can be the same or can be different. As an example, the same or different flanking sequences can link the NK engaging domain (e.g., anti-CD16 receptor scFv) with the NK activating domain (e.g., IL-15) and the NK activating domain with the targeting domain (e.g., anti-CLEC12A scFv). In some embodiments, constructs that lack a flanking sequence exhibit reduced activity compared to constructs that possess the flanking sequence.

In some embodiments, the compounds described herein include at least one flanking sequence linking two of the domains. In some embodiments, the compounds described herein further include a second flanking sequence linking the two linked domains with a third domain. In some embodiments, the flanking sequences are the same. In some embodiments, the flanking sequences are different.

In some embodiments, the flanking sequences flank the NK activating domain. In some embodiments, a first flanking sequence is C-terminal to the NK engaging domain. In some embodiments, a second flanking sequence is N-terminal to the anti-CLEC12A targeting domain. In some embodiments, a first flanking sequence is C-terminal to the NK engaging domain and a second flanking sequence is N-terminal to the anti-CLEC12A targeting domain.

Formulations

The compounds described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with a TriKE molecule without causing any undesirable biological effects or interacting in a deleterious manner with any of the other components of the pharmaceutical composition in which it is contained.

A TriKE molecule may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, a TriKE molecule may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing a TriKE molecule into association with a carrier that constitutes one or more accessory ingredients. In general, a formulation may be prepared by uniformly and/or intimately bringing the active molecule into association with a liquid carrier, a finely divided solid carrier, or both, and then, if necessary, shaping the product into the desired formulations.

Methods of Treatment

In some embodiments, provided herein, are methods that include administering to a subject a compound or molecule described herein in an amount effective to induce NK-mediated killing of a target cell. Any cell can be a target cell. In some embodiments, the target cell is a cancer cell. The methods described herein can include administering to the subject a TriKE molecule in an amount effective to induce NK-mediated killing of the target cells in the subject. In some embodiments, TriKE molecules are administered to treat a disease or condition of the subject.

As used herein, "treat" or variations thereof refer to reducing, limiting progression, ameliorating, or resolving, to any extent, the symptoms or signs related to a condition. As used herein, "ameliorate" refers to any reduction in the extent, severity, frequency, and/or likelihood of a symptom or clinical sign characteristic of a particular condition; "symptom" refers to any subjective evidence of disease or of a patient's condition; and "sign" or "clinical sign" refers to an objective physical finding relating to a particular condition capable of being found by one other than the subject or patient.

As used herein, the term "subject" refers to any individual or patient on which the methods disclosed herein are performed. The term "subject" can be used interchangeably with the term "individual" or "patient." A "subject" can be any animal such as, for example, a mammal (e.g., dog, cat, horse, cow, sheep, goat, monkey, etc.). In certain embodiments, the subject can be a human.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Thus, in certain embodiments, the method can involve prophylactic treatment of a subject at risk of developing a condition. "At risk" refers to a subject that may or may not actually possess the described risk. Thus, for example, a subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of a condition can include, for example, genetic predisposition, ancestry, age, sex, geographical location, lifestyle, or medical history. Treatment may also be continued after symptoms have resolved, for example to prevent or delay their recurrence.

In other embodiments, methods for stimulating expansion of NK cells in vivo are provided herein that include administering to a subject a compound or molecule described herein in an amount effective to stimulate expansion of NK cells in the subject. In some embodiments, TriKE molecules are administered to treat a disease or condition of the subject. Using a TriKE molecule as a part of an in vivo treatment can make NK cells antigen specific with simultaneous co-stimulation, enhancement of survival, and expansion, which may be antigen specific. In other cases, the TriKE can be used in vitro as an adjuvant to NK cell adoptive transfer therapy.

In still other embodiments, methods of treating cancer are provided herein that include administering to s subject a compound or molecule described herein effective for treating the cancer. In some embodiments, the cancer is prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, or hematopoietic cancer. In some embodiments, the hematopoietic cancer is a myelodysplastic syndrome (MDS). In some embodiments, the hematopoietic cancer is a lymphoma. In some embodiments, the hematopoietic cancer is a leukemia. In some embodiments, the hematopoietic cancer is acute myeloid leukemia (AML).

As used herein, the term "myeloid leukemia" refers to leukemia characterized by proliferation of myeloid tissue and an abnormal increase in the number of granulocytes, myelocytes and myeloblasts in the circulating blood. This term is synonymous with the terms myelocytic leukemia, myelogenic leukemia, myelogenous leukemia and granulocytic leukemia. The term "myeloid leukemia" can represent inter alia acute and chronic myeloid leukemias (AML and CML), acute promyelocytic leukemia (APL), chronic myelomonocytic leukemia ("CMML"), myelodysplastic syndrome and juvenile myelomonocytic leukemia which involve the myeloid elements of the bone marrow (e.g., white cells, red cells and megakaryocytes) and includes all subtypes which are defined by morphological, histochemical and immunological techniques that are well known by those skilled in the art. Subtypes of AML include according to the FAB classification FAB-M0, FAB-M1, FAB-M2, FAB-M3, FAB-M4, FAB-M5, FAB-M6 and FAB-M7.

As used herein, the term "myelodysplastic syndrome" encompasses a heterogeneous group of closely related clonal hematopoietic disorders that originate in an early blood-forming cell in the marrow. All disorders are characterized by a cellular marrow with impaired morphology and maturation (dysmyelopoiesis) and peripheral blood cytopenias, resulting from ineffective blood cell production. In other words, the maturing blood cells often die in the marrow before they reach full maturity and enter the blood, accounting for the low blood cell concentrations. In patients suffering from myelodysplastic syndrome there may also be an accumulation of very immature marrow cells, called leukemic blast cells.

The amount of TriKE molecule administered can vary depending on various factors including, but not limited to, the specific TriKE molecule being used, the weight, physical condition, and/or age of the subject, and/or the route of administration. Thus, the absolute weight of TriKE molecule included in a given unit dosage form can vary widely, and depends upon factors such as the species, age, weight and physical condition of the subject, and/or the method of administration. Accordingly, it is not practical to set forth generally the amount that constitutes an amount of TriKE molecule effective for all possible applications. Those of ordinary skill in the art, however, can readily determine the appropriate amount with due consideration of such factors.

In some embodiments, the method can include administering sufficient amounts of a TriKE molecule to provide a dose of, for example, from about 100 ng/kg to about 50 mg/kg to the subject, although in some embodiments the methods may be performed by administering a TriKE molecule in a dose outside this range. In some of these embodiments, the method includes administering sufficient amounts of a TriKE molecule to provide a dose of from about 10 μg/kg to about 5 mg/kg to the subject, for example, a dose of from about 100 μg/kg to about 1 mg/kg.

Alternatively, the dose may be calculated using actual body weight obtained just prior to the beginning of a treatment course. For the dosages calculated in this way, body surface area (m2) is calculated prior to the beginning of the treatment course using the Dubois method: m2=(wt kg0.425×height cm0.725)×0.007184.

In some embodiments, the method can include administering sufficient amounts of a TriKE molecule to provide a dose of, for example, from about 0.01 mg/m2 to about 10 mg/m2.

In some embodiments, a TriKE molecule may be administered, for example, from a single dose to multiple doses per week, although in some embodiments the method can be performed by administering a TriKE molecule at a frequency outside this range. In certain embodiments, a TriKE molecule may be administered from about once per month to about five times per week.

In some embodiments, the method further includes administering one or more additional therapeutic agents. The one or more additional therapeutic agents may be administered before, after, and/or coincident to the administration of a TriKE molecule. A TriKE molecule and the additional therapeutic agents may be co-administered. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another. In other embodiments, the TriKE molecule and the additional therapeutic agent may be administered as part of a mixture or cocktail. In some aspects, the administration of TriKE molecule may allow for the effectiveness of a lower dosage of other therapeutic modalities when compared to the administration of the other therapeutic agent or agents alone, thereby decreasing the likelihood, severity, and/or extent of the toxicity observed when a higher dose of the other therapeutic agent or agents is administered.

Exemplary additional therapeutic agents include altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine.

Accordingly, in some embodiments, methods of treating cancer provided herein further include administering a compound, molecule, composition, or formulation described herein prior to, simultaneously with, or following chemotherapy, surgical resection of a tumor, or radiation therapy. The chemotherapy can include altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine, for example.

In some embodiments, the methods provided herein can include administering sufficient TriKE molecules as described herein and administering at least one additional therapeutic agent, with administration of TriKE molecules and at least one additional therapeutic agent demonstrating therapeutic synergy. In some aspects of the methods of the present invention, a measurement of response to treatment observed after administering both a TriKE molecule as described herein and the additional therapeutic agent is improved over the same measurement of response to treatment observed after administering either the TriKE molecule or the additional therapeutic agent alone. In some embodiments, an additional therapeutic agent can include an additional agent that targets EpCAM including, for example, an EpCAM specific monoclonal antibody, such as, for example, Catumaxomab, a monoclonal hybrid antibody targeting EpCAM and CD3.

As used herein, the term "and/or" means one or all of the listed elements or a combination of any two or more of the listed elements; the terms "comprises," "comprising," and variations thereof are to be construed as open ended—i.e., additional elements or steps are optional and may or may not be present.

As used herein, the singular forms "a", "an", and "the" include plural references unless the context clearly dictates otherwise. Unless otherwise specified, "a," "an," "the," and "at least one" can be used interchangeably and can mean one or more than one. Thus, for example, references to "the method" includes one or more methods, and/or steps of the type described herein which will become apparent to those persons skilled in the art upon reading this disclosure and so forth.

As used herein, the recitations of numerical ranges by endpoints include all numbers subsumed within that range (e.g., 1 to 5 includes 1, 1.5, 2, 2.75, 3, 3.80, 4, 5, etc.).

"About" as used herein when referring to a measurable value such as an amount, a temporal duration, and the like, is meant to encompass variations of ±20%, or ±10%, or ±5%, or even ±1% from the specified value, as such variations are appropriate for the disclosed methods or to perform the disclosed methods.

Unless defined otherwise, all technical and scientific terms used herein have the same meaning as is commonly understood by one of skill in the art to which this invention belongs.

As used herein, the term "protein" refers to any polymeric chain of amino acids. The terms "peptide" and "polypeptide" are used interchangeably with the term "protein" and also refer to a polymeric chain of amino acids. The term "protein" encompasses native or artificial proteins, protein fragments and polypeptide analogs of a protein sequence. A protein may be monomeric or polymeric. The term "protein" encompasses fragments and variants (including fragments of variants) thereof, unless otherwise contradicted by context.

As used herein, the term "nucleic acid" refers to any deoxyribonucleic acid (DNA) molecule, ribonucleic acid (RNA) molecule, or nucleic acid analogues. A DNA or RNA molecule can be double-stranded or single-stranded and can be of any size. Exemplary nucleic acids include, but are not limited to, chromosomal DNA, plasmid DNA, cDNA, cell-free DNA (cfDNA), mRNA, tRNA, rRNA, siRNA, micro RNA (miRNA or miR), hnRNA. Exemplary nucleic analogues include peptide nucleic acid, morpholino- and locked nucleic acid, glycol nucleic acid, and threose nucleic acid.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. Further, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

This example describes development of the CD16-IL15-CLEC12A TriKE.

Figure 1B:
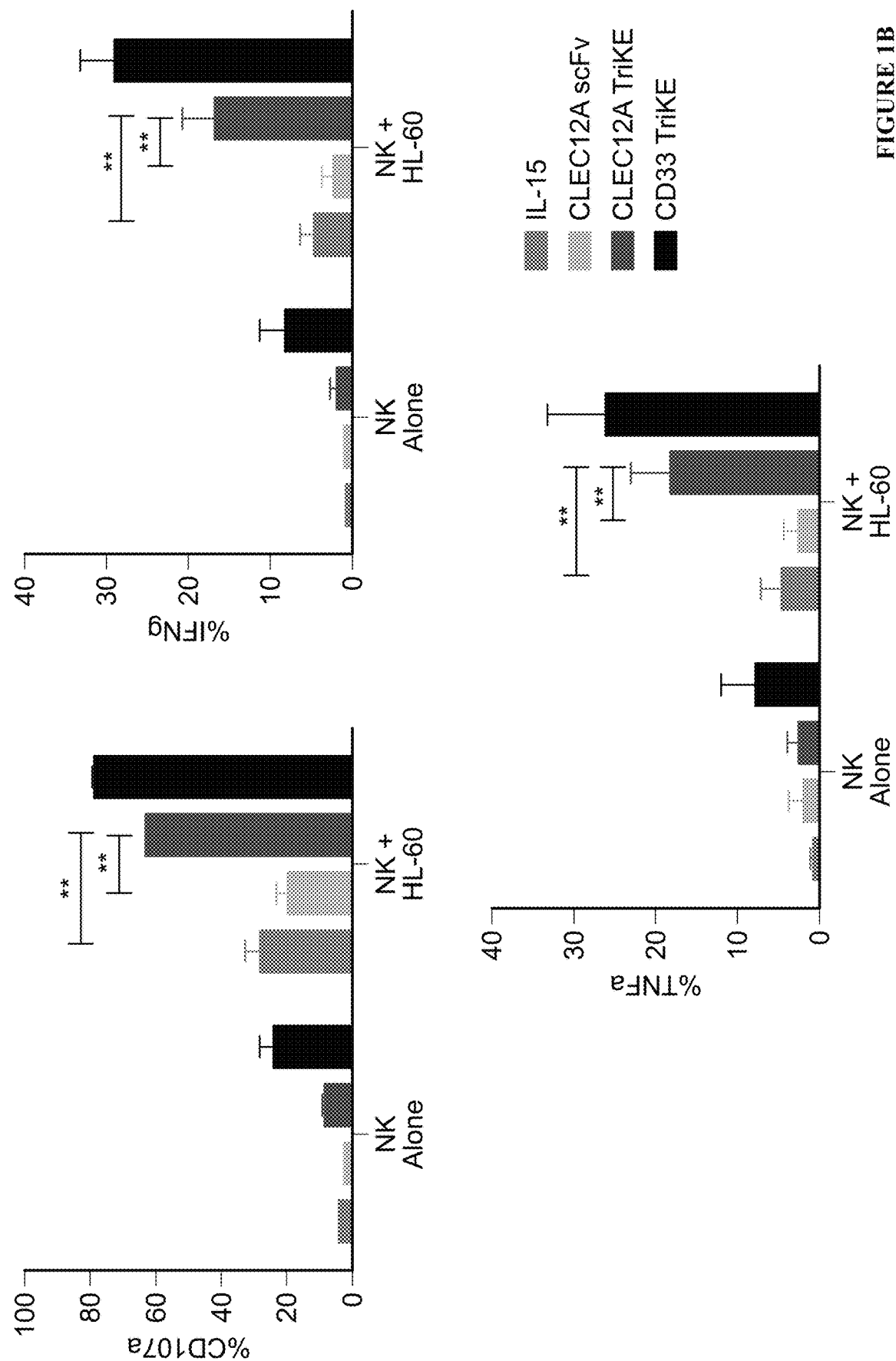
Figure 1C:
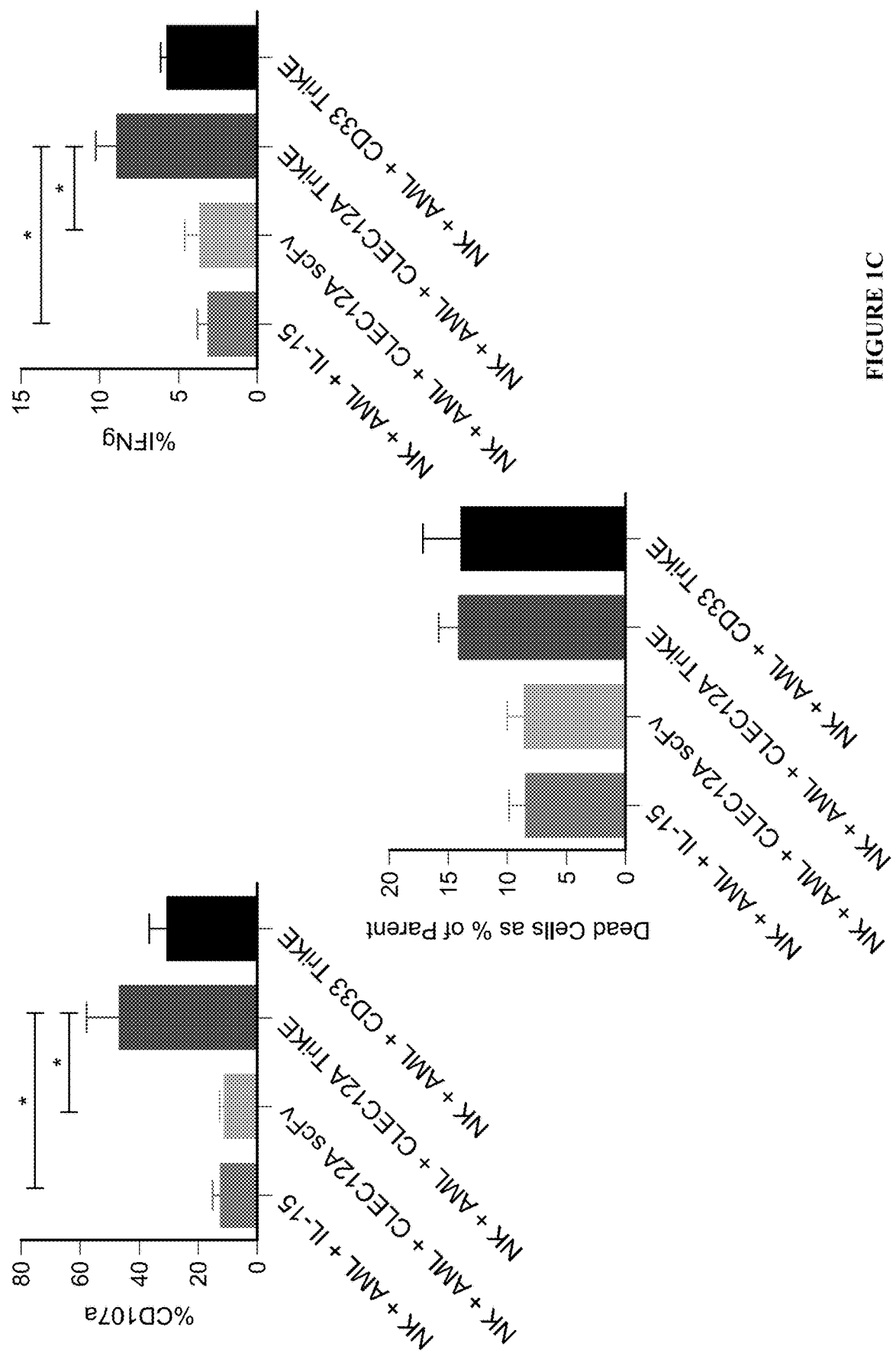

The 1615CLEC12A TriKE was developed in a mammalian cell system to ensure that appropriate post-translational modifications are present. Specific binding of the TriKE to HL-60 and THP-1 target cells that express CLEC12A compared to Raji cells that do not express CLEC12A was confirmed. Treatment of peripheral blood mononuclear cells (PBMCs) with the 1615CLEC12A TriKE drove a significant increase in NK cell specific proliferation over 7 days as measured by CellTrace dilution compared to treatment with a CLEC12A scFv or IL-15 alone (69.7±6.7% vs 11.9±2.5% vs 38.4±7.3%) (FIG. 1A). To measure NK cell killing, an IncuCyte Zoom assay was conducted. Here, HL-60 target cells were labeled with a caspase 3/7 reagent where a color change indicates target cell death. The 1615CLEC12A TriKE was able to induce more target cell killing than CLEC12A scFv or IL-15 as measured by number of live target cells at the end of the 48 hour assay (53.9±1.9% vs 103.3±3.4% vs 71.1±1.4%). The 1615CLEC12A TriKE induced an increase in NK cell degranulation, measured by CD107a expression against HL-60 AML tumor targets in a 4 hour functional assay compared to treatment with CLEC12A scFv or IL-15 alone (62.3±1.1% vs 19.4±3.8% vs 27.5±4.9%). In this assay, there was also an increase in cytokine production, measured by IFNg and TNFa respectively (16.7±4.2% vs 2.3±1.5% vs 4.7±1.9% and 18.0±5.1% vs 2.5±1.7% vs 4.6±2.5%) (FIG. 1B). A similar enhanced functional response with THP-1 AML tumor targets was observed. In these functional assays, treatment with the 1615CLEC12A TriKE produced less background activation compared to the CD33 TriKE, indicating less off-target effects on PBMCs. To confirm the clinical relevance of this molecule, the efficacy of the 1615CLEC12A TriKE against primary AML targets was tested. AML blasts were identified as SSC low, CD45 intermediate and CD34 high cells. Out of the 9 AML samples tested, 7 expressed high levels of CD33 (70.4±6.3%) and CLEC12A (78.1±5.2%). In functional assays with these samples, the 1615CLEC12A TriKE was able to induce greater CD107a and IFNg expression, and enhanced killing of tumor targets as measured by a live/dead stain compared to CLEC12A scFv or IL-15 (FIG. 1C). In these assays, the efficacy of the 1615CLEC12A TriKE was comparable to the CD33 TriKE. These data demonstrate that the 1615CLEC12A TriKE drives NK cell specific proliferation, degranulation, cytokine secretion, and killing of tumor targets in vitro. Apart from AML, CLEC12A is expressed on cancer cells and LSCs in patients with myelodysplastic syndromes (MDS). These findings highlight the clinical potential of the 1615CLEC12A TriKE individually or in combination with the CD33 TriKE for the treatment of MDS and AML.

Example 2

This example describes expression of CD33 and CLEC12A on AML cells.

A majority of all deaths from hematopoietic malignancies are caused by acute myeloid leukemia (AML) which has a poor five-year survival rate of 26%, highlighting the need for new therapies. The most common antigen used to target AML cells is CD33. However, there are many limitations of developing therapies against CD33. For example, not all cancer cells express CD33, including cancer cells in patients with refractory AML. In addition, all cells of the myeloid lineage and some cells of the lymphoid lineage like activated NK cells and T cells express CD33, leading to off-target toxicity. Further, cancer stem cells, which are thought to facilitate relapse, do not express CD33.

A novel antigen called C-type Lectin-like molecule 1 (CLL-1) or CLEC12A was targeted to address the above limitations.

Figure 2:
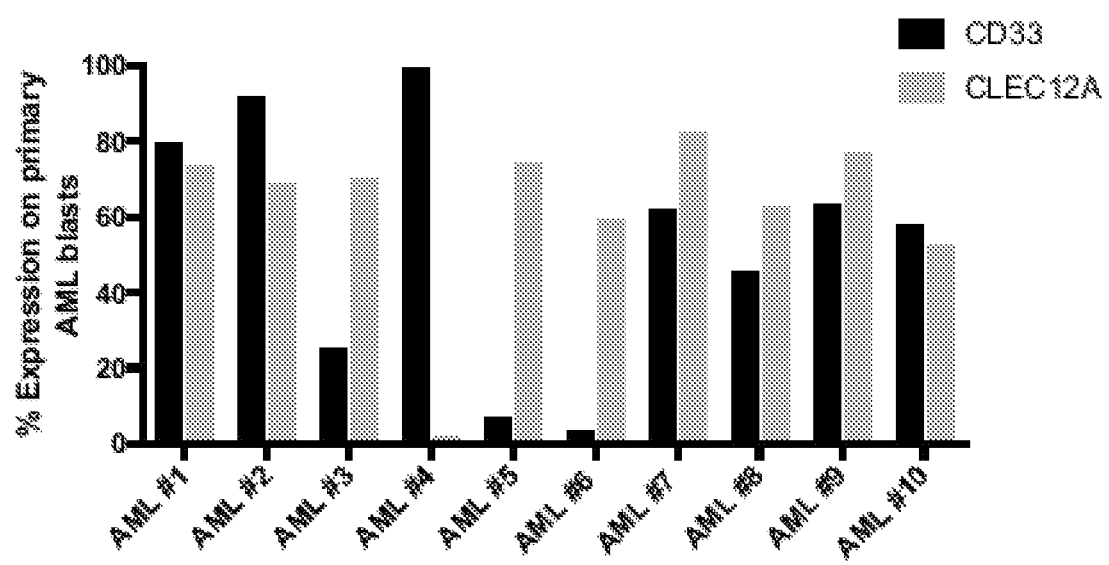
FIG. 2 illustrates the percentage of CD33 and CLEC12A surface expression on primary AML samples from 10 patients.

FIG. 2 shows the percentage of CD33 and CLEC12A surface expression measured by flow cytometry analysis of primary AML samples from 10 patients. CLEC12A was highly expressed on AML cells. About 70% of CD33 negative cells expressed CLEC12A. The expression of CLEC12A was restricted to a subset of myeloid cells, limiting off-target toxicity. CLEC12A was present on leukemic stem cells but not hematopoietic stem cells.

These data establish CLEC12A as a surface marker on both primary AML cells that express CD33 and that lack CD33 expression. Thus, in accordance with some embodiments, CLEC12A can be targeted by a tri-specific killer engager (TriKE) molecule on AML and other cells that express or lack CD33.

Example 3

This example describes the tri-specific killer engager (TriKE) molecule targeting CLEC12A.

To target cancer cells using Natural Killer (NK) cells, a tri-specific killer engager (TriKE) molecule was developed containing an anti-CD16 heavy chain antibody that activates NK cells, an IL-15 molecule that drives NK cell priming, expansion and survival, and an anti-CLEC12A single chain variable fragment (scFv) that engages cancer targets. A schematic of the CD16-IL15-CLEC12A TriKE and mechanism of action is shown in FIGS. 3A-B.

Figure 3A:
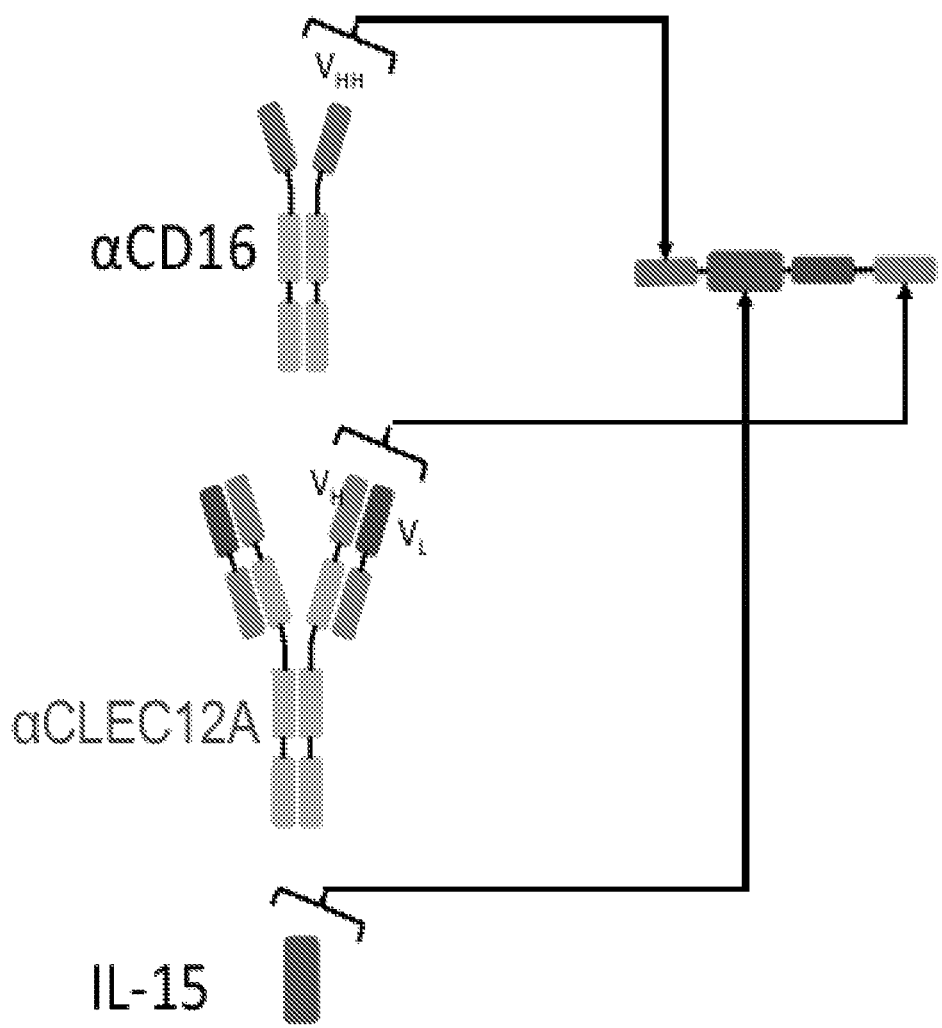
FIGS. 3A-3B illustrate the CD16-IL15-CLEC12A TriKE (FIG. 3A) and mechanisms of action (FIG. 3B).
Figure 3B:
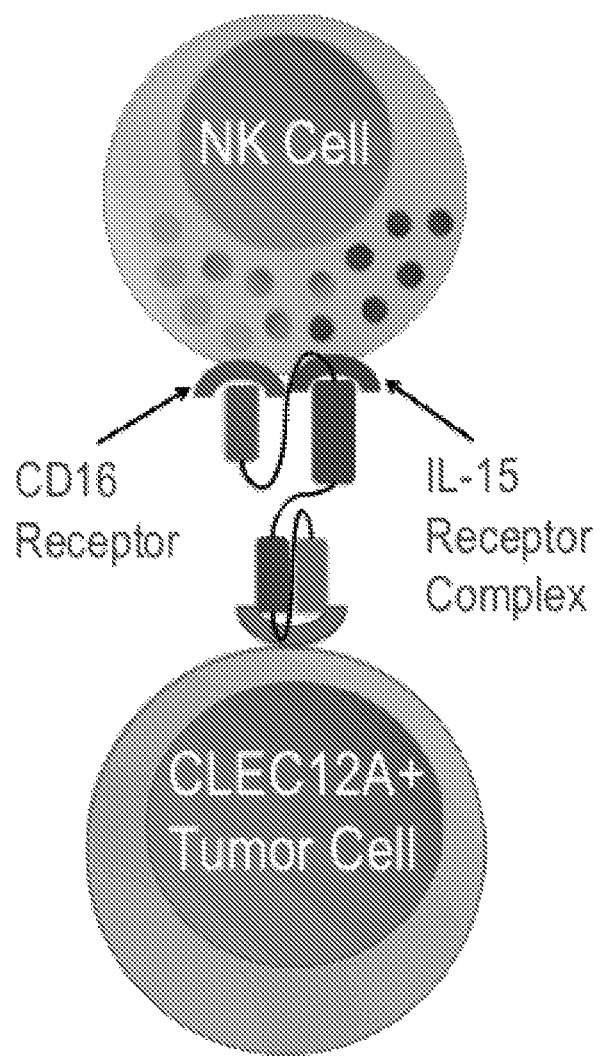

The TriKE contains an anti-CD16 heavy-chain antibody constructed by incorporating the CDRs of a llama anti-CD16 $V_{HH}$ into a humanized $V_{HH}$ backbone (FIG. 3A). This is linked to a wild type IL-15 molecule which is linked to the scFv from an anti-CLEC12A antibody. The TriKE (SEQ ID NO.:1) was produced in a mammalian system with Expi-293 cells and contains a His tag which was used to purify the molecule. In accordance with some embodiments, the TriKE molecule may lack a His tag. A TriKE molecule that lacks a His tag can be suitable for use in clinical applications, although a TriKE containing a His tag can be used as well. The TriKE creates an immunological synapse between a CLEC12A+ tumor cell and NK cell promoting release of cytotoxic granules and secretion of cytokines that kills the target cell (FIG. 3B).

In addition to the scFv from an anti-CLEC12A antibody described above as an illustrative example (SEQ ID NO.:4; corresponding to SC02-357 of U.S. Pat. No. 7,741,443), the TriKE targeting domain can comprise any sequence capable of targeting or binding to CLEC12A, such as scFvs SC02-378 and SC02-161 and any derivatives of scFvs SC02-357, SC02-378, and SC02-161. scFvs SC02-357, SC02-378, and SC02-161 are described in U.S. Pat. No. 7,741,443, the disclosure of which is incorporated herein in its entirety, specifically with respect to scFvs SC02-357, SC02-378, and SC02-161 sequences.

Example 4

This example describes binding validation of the CD16-IL15-CLEC12A TriKE to target cells.

Figure 4:
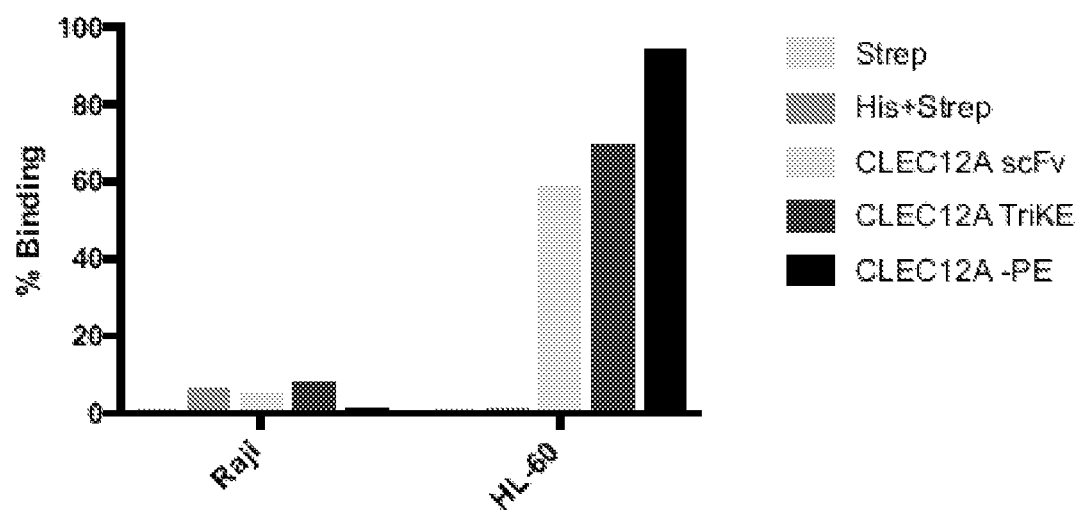
FIG. 4 illustrates binding of the CD16-IL15-CLEC12A TriKE to targets that express CLEC12A.

CLEC12A+ HL-60 and CLEC12A− Raji targets were incubated with the 1615CLEC12A TriKE or scFv at equimolar concentrations. Binding was assessed by an anti-His antibody that binds to the His tag on the TriKE or scFv. A secondary Streptavidin antibody was used that was detected by flow cytometry. Data in FIG. 4 shows that 1615CLEC12A TriKE bound to HL-60 targets, but not Raji targets.

Figure 14A:
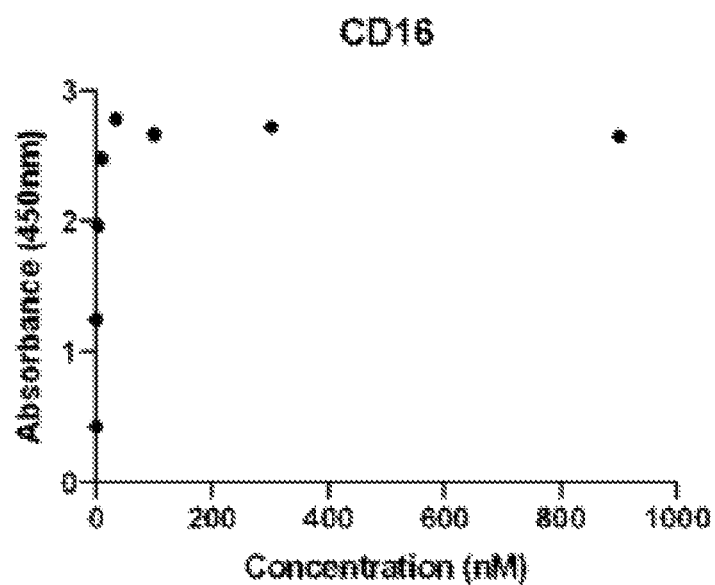
FIGS. 14A-14C illustrate binding validation of the CD16-IL15-CLEC12A TriKE.
Figure 14B:
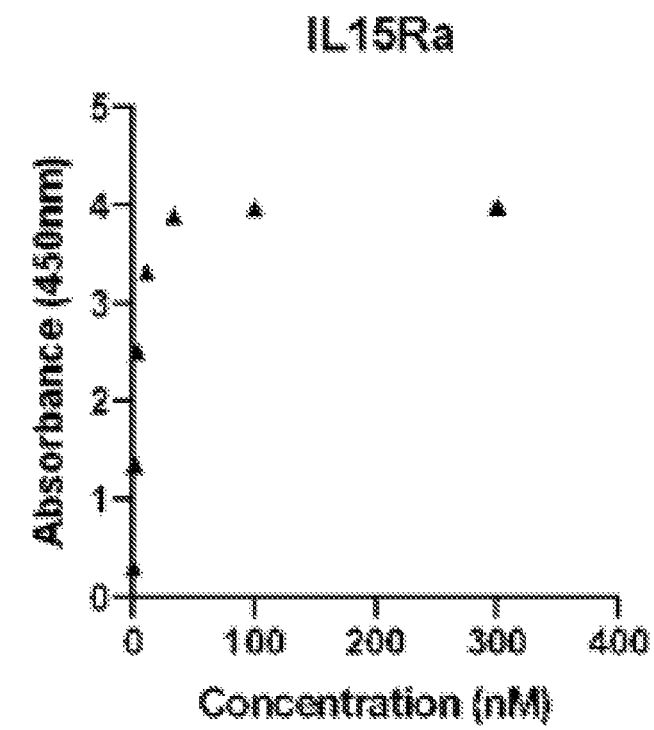
Figure 14C:
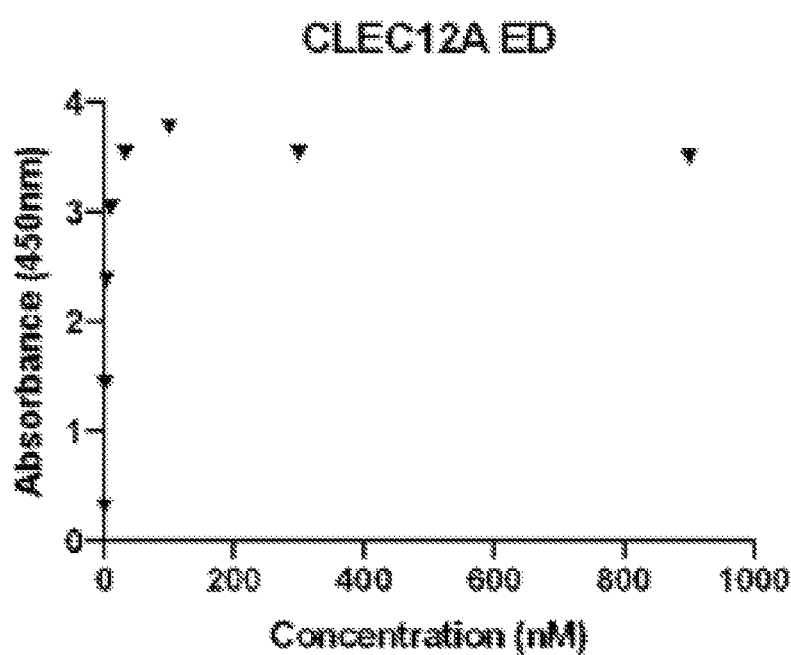

Binding of the different components of the 1615CLEC12A TriKE was tested using an ELISA against CD16 (FIG. 14A), IL15 receptor alpha (FIG. 14B), and CLEC12A extracellular domain (ED; FIG. 14C). The TriKE was tested in 3 fold serial dilutions from 900 nM to 0.4 nM and had the highest binding at 30 nM, which was used in subsequent experiments, unless otherwise noted.

These data show that each component of the 1615CLEC12A TriKE bound to its respective target molecule and that CD16-IL15-CLEC12A TriKE specifically bound to targets that express CLEC12A.

Example 5

This example describes NK cell proliferation induced by CD16-IL15-CLEC12A TriKE.

Figure 5A:
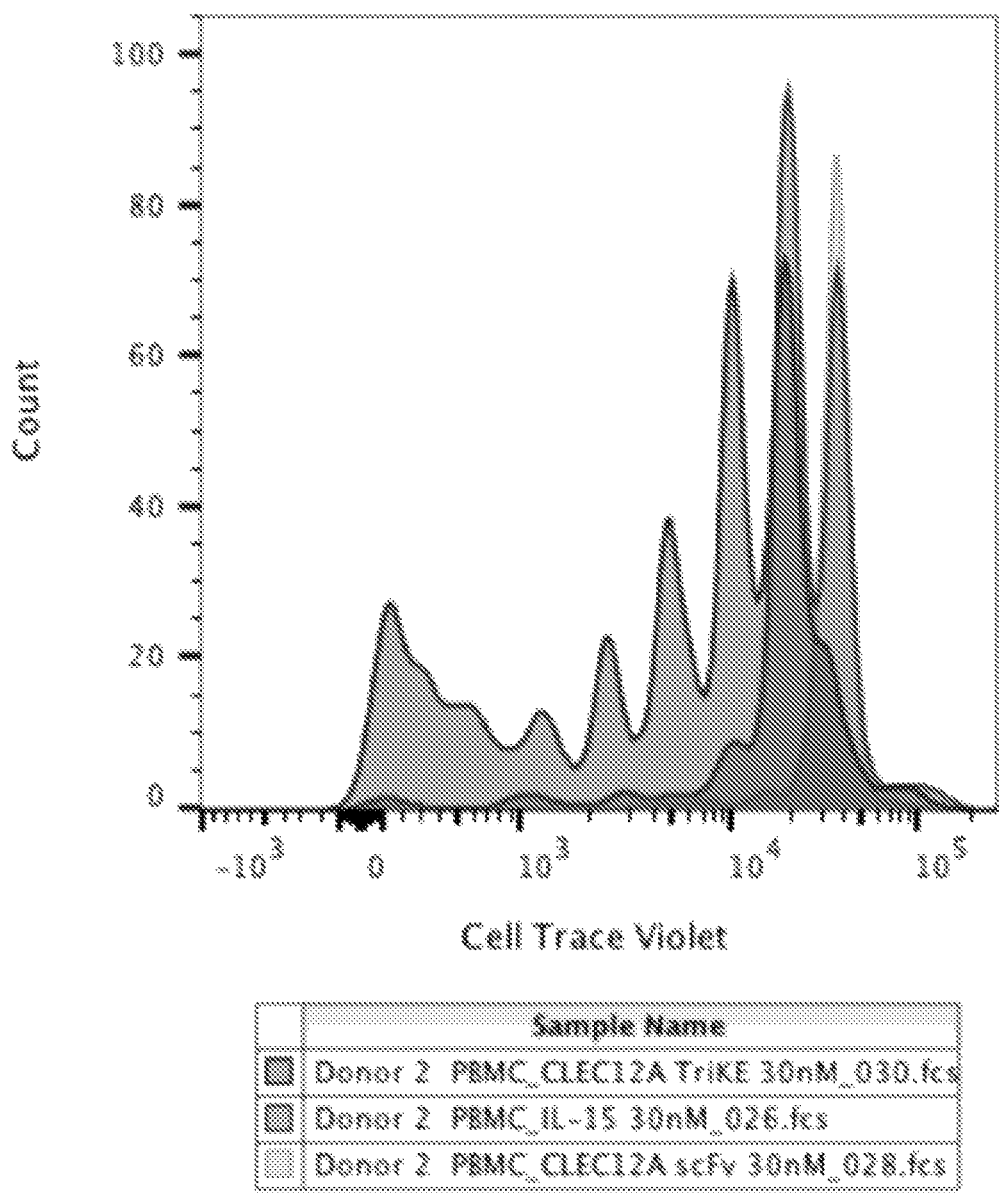
FIGS. 5A-5B illustrate CD16-IL15-CLEC12A TriKE promotion of NK cell proliferation.
Figure 5B:
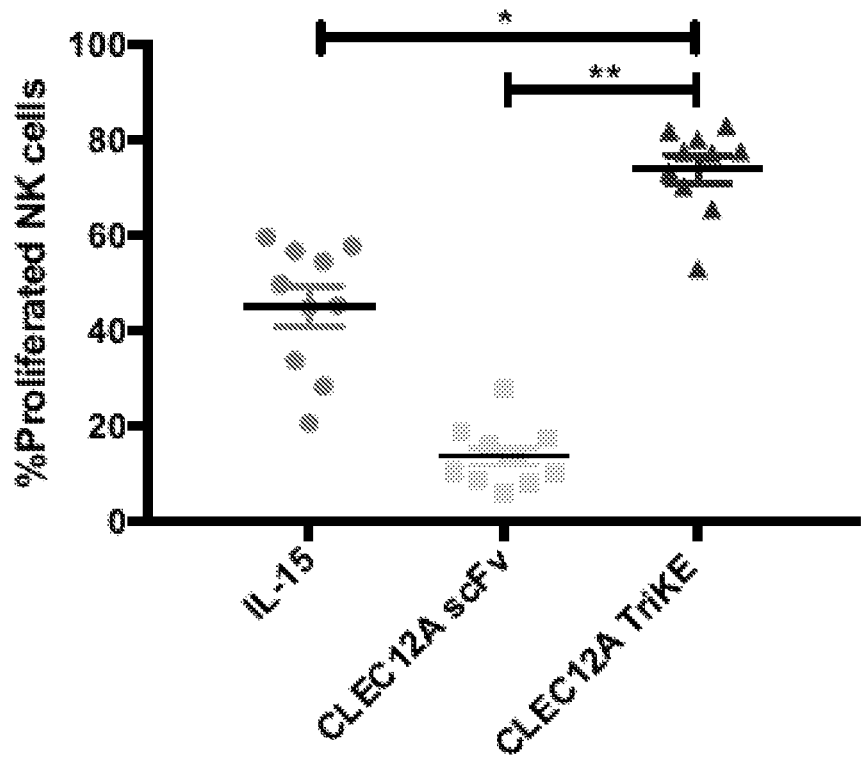

PBMCs were labeled with Cell Trace and incubated with equimolar concentrations of IL-15, CLEC12A scFv or CLEC12A TriKE for 7 days (FIG. 5A). The NK cell population was assessed by evaluating dilution of Cell Trace dye in the CD56+CD3− population using flow cytometry (FIG. 5B). The percentage of proliferated NK cells was calculated using FlowJo Analyzer. Statistics reflect significant differences between the groups as calculated with a One Way ANOVA, *$P<0.05$, **$P<0.005$, N=10. A greater percentage of proliferated NK cells was seen in the presence of CLEC12A TriKE as compared to IL-15 or CLEC12A scFv.

In other experiments, PBMCs were isolated from fresh healthy donor samples (n=6), CellTrace Violet labeled, and incubated for 7 days with 1615CLEC12A TriKE or control treatments at 30 nM, as described above. After the incubation period, cells were harvested and NK cell (CD3−, CD56+) proliferation was evaluated by flow cytometry.

Figure 9A:
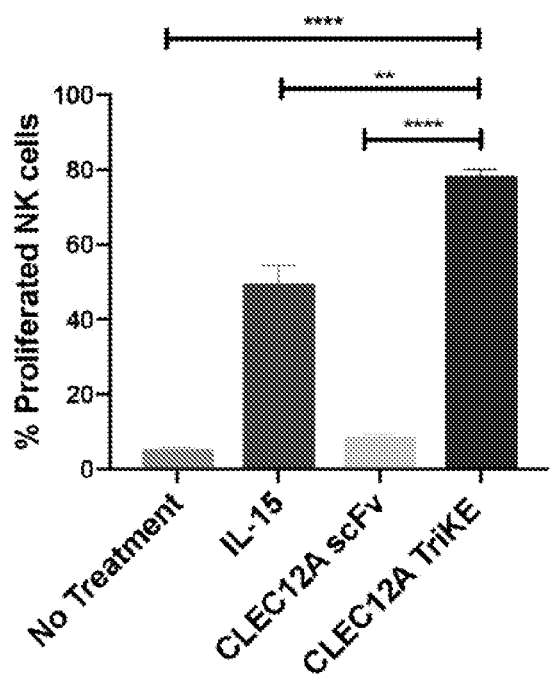
FIGS. 9A-9C illustrate CD16-IL15-CLEC12A TriKE induction of NK cell proliferation.
Figure 9B:
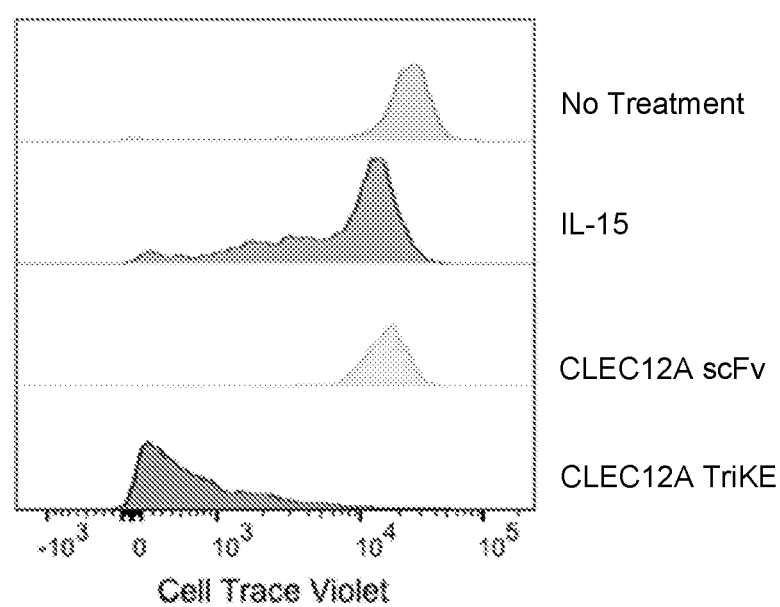
Figure 9C:
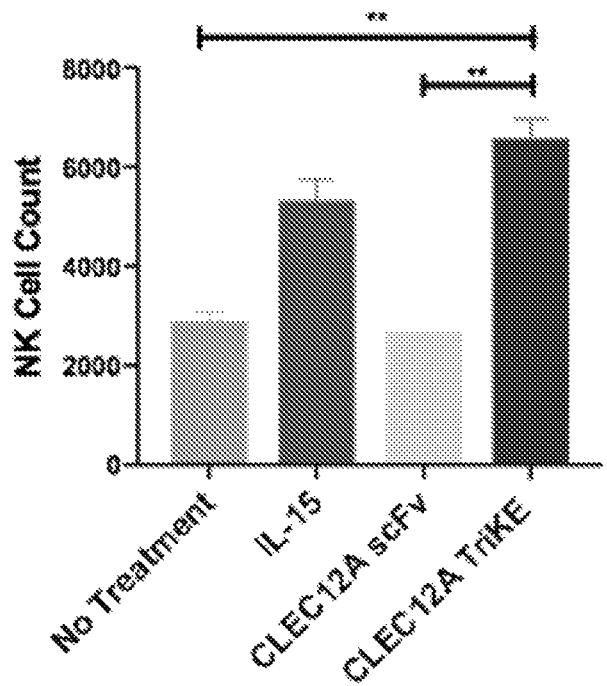

Pooled data (FIG. 9A) and representative histograms (FIG. 9B) show NK cell proliferation (by CellTrace dilution) for the different treatment groups. FIG. 9C shows pooled NK cell count (45 seconds at constant speed) at the time of harvest. One-way analysis of variance (ANOVA) with repeated measures was used to calculate differences compared to the 1615CLEC12A group. Error bars indicate +/− standard error of the mean. Statistical significance are determined as $P<0.005$, **$P<0.0001$. Significantly greater percentages of proliferated NK cells were seen upon treatment with CLEC12A TriKE as compared to no treatment, treatment with IL-15, or treatment with CLEC12A scFv.

These data show that the 1615CLEC12A TriKE induced potent NK cell proliferation.

Example 6

This example describes functional validation of the CD16-IL15-CLEC12A TriKE.

Figure 6A:
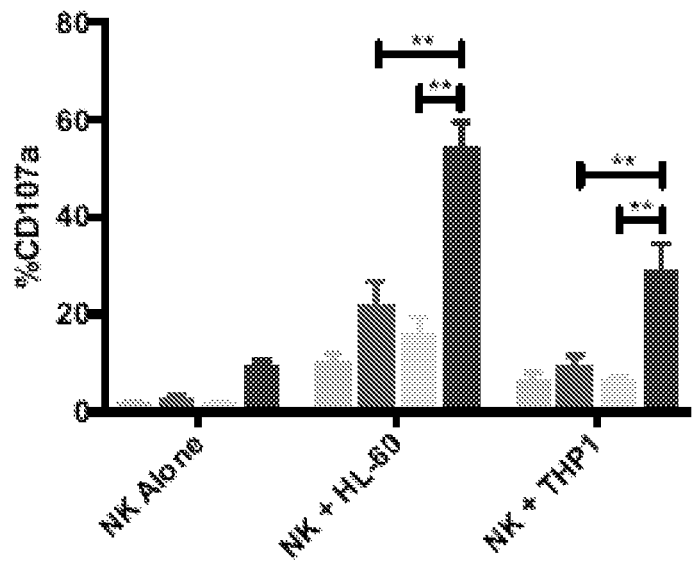
FIGS. 6A-6C illustrate CD16-IL15-CLEC12A TriKE induction of degranulation (FIG. 6A) and cytokine production (FIGS. 6B-C) against AML target cells.
Figure 6B:
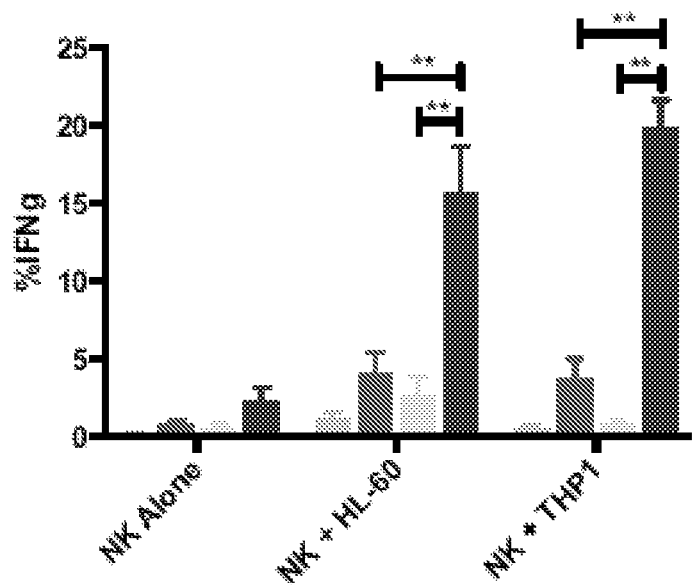
Figure 6C:
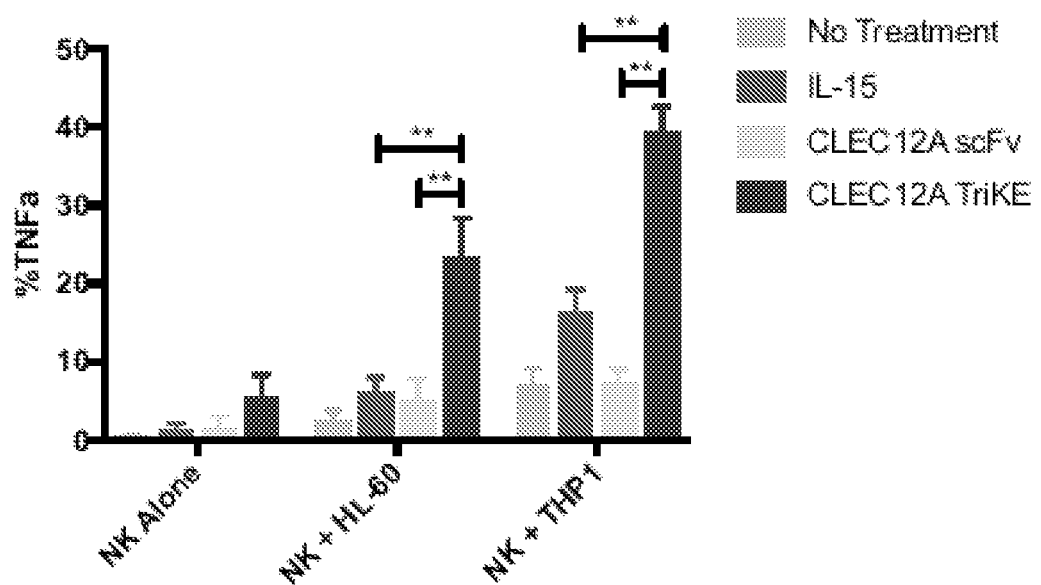

PBMCs were incubated with CLEC12A+ HL-60 and THP1 cells at a 2:1 effector to target ratio in the presence of IL-15, CLEC12A scFv or CLEC12A TriKE at equimolar concentrations. Surface CD107a, to evaluate degranulation (FIG. 6A), intracellular IFNg (FIG. 6B), and TNFa to evaluate inflammatory cytokine production (FIG. 6C), were assessed on CD56$^+$CD3$^−$ NK cells by flow cytometry. Statistics comparing treatment with CLEC12A TriKE to treatment with IL-15 or CLEC12A scFv controls reflect significant differences between the groups as calculated with a One Way ANOVA, **$P<0.005$, N=6. A greater percentage of CD107a surface staining and greater percentages of IFNg and TNFa intracellular staining on NK cells were seen in the presence of CLEC12A TriKE as compared to no treatment, treatment with IL-15, or treatment with CLEC12A scFv for both HL60 and THP1 target cells.

Figure 10A:
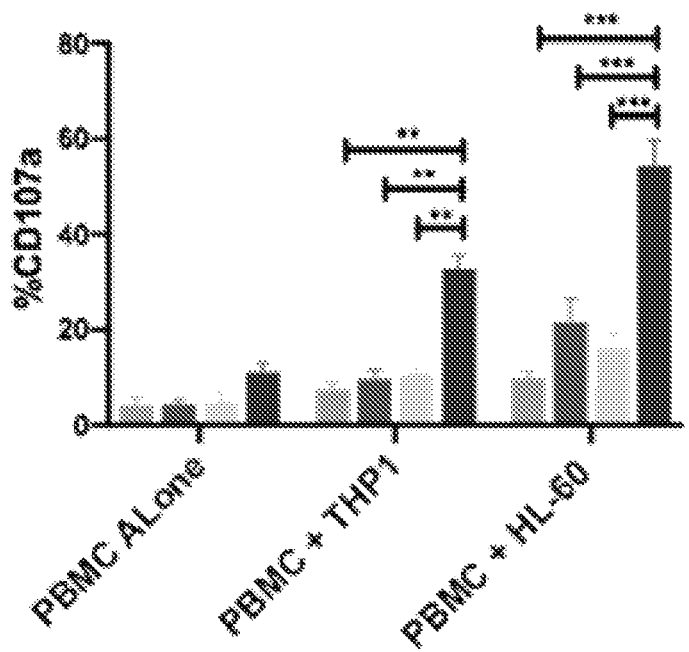
FIGS. 10A-10D illustrate functional validation of the CD16-IL15-CLEC12A TriKE.
Figure 10B:
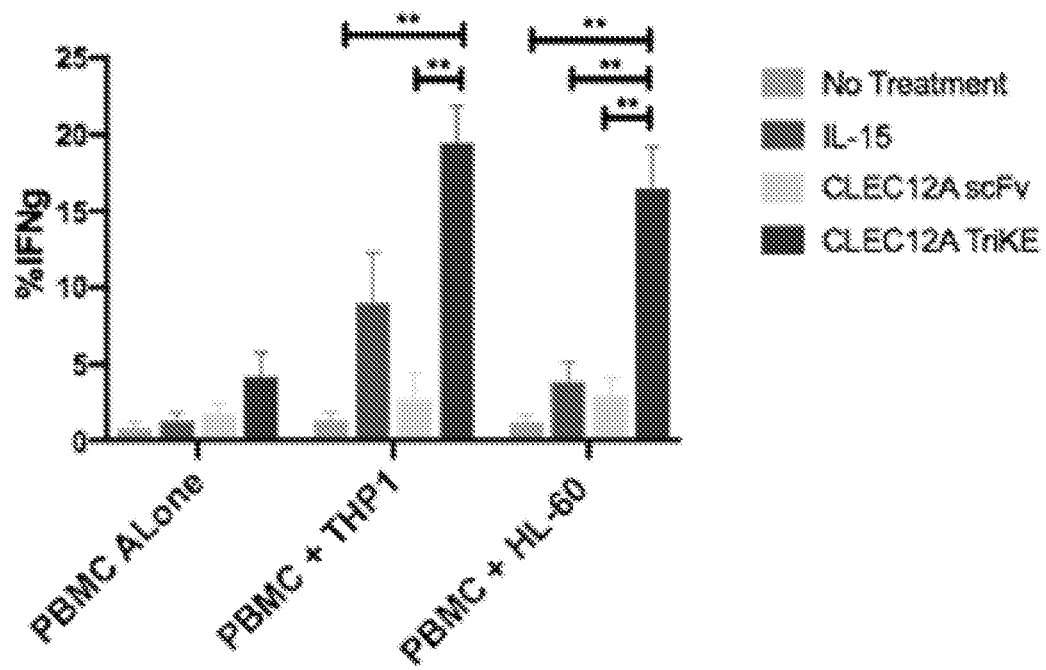
Figure 10C:
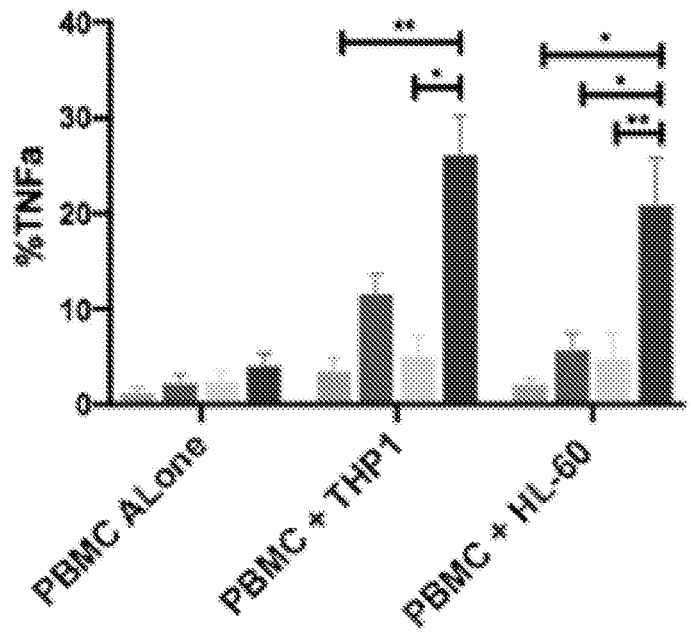
Figure 10D:
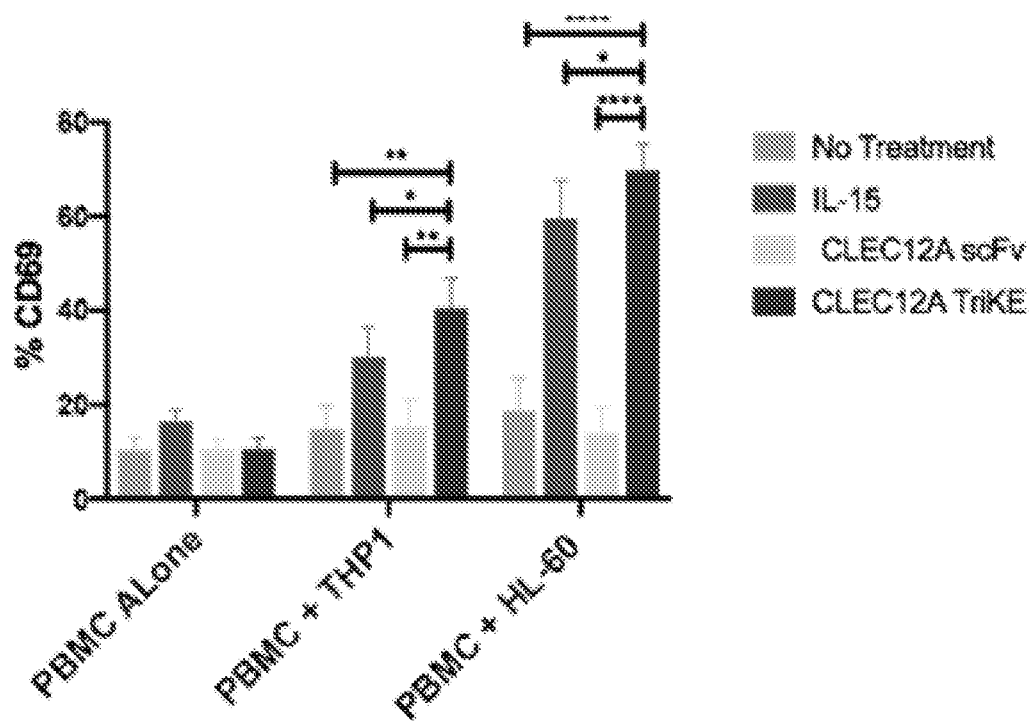

In other experiments, frozen PBMCs from healthy donors (n=6) were incubated with the indicated treatments (30 nM) to evaluate CD107a expression as a marker of degranulation (FIG. 10A), intracellular IFNg production (FIG. 10B), or intracellular TNFa expression in NK cells (CD3−, CD56+; FIG. 10C) in a 4-hour assay. The cells were evaluated with PBMCs alone or in the presence of THP1 and HL-60 targets at a 2:1 effector/target ratio. Activation of NK cells (CD3−, CD56+) in PBMCs were evaluated using CD69 expression in a 4-hour assay with PBMCs alone or in the presence of THP1 and HL-60 targets at a 2:1 effector/target ratio (FIG. 10D). One-way analysis of variance (ANOVA) with repeated measures was used to calculate differences against the 1615CLEC12A group. Error bars indicate+/−standard error of the mean. Statistical significance are determined as *P, 0.05, P, 0.01, *P, 0.001, and ****P, 0.0001.

Greater NK cell activation was seen, demonstrated by increased staining for CD107a, IFNg, TNFa, and CD69 upon incubation with CLEC12A TriKE as compared to no treatment, treatment with IL-15, or treatment with scFv for both THP1 target cells and HL60 target cells (FIGS. 10A-D).

These data show that the 1615CLEC12A TriKE induced degranulation and cytokine production against AML target cells, including THP1 and HL-60 targets.

Example 7

This example describes CD16-IL15-CLEC12A TriKE-induced killing of AML targets.

Figure 7A:
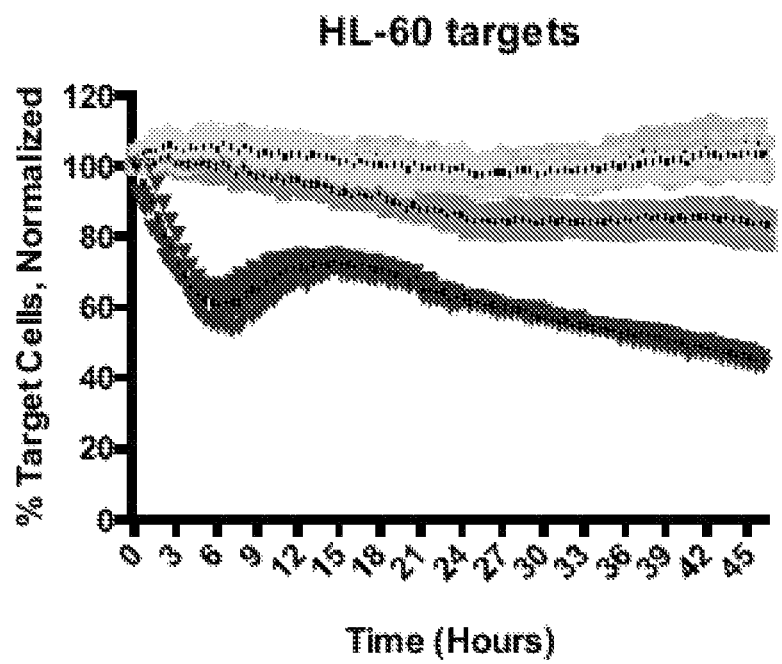
FIGS. 7A-7B illustrate CD16-IL15-CLEC12A TriKE induction of AML target cell killing.
Figure 7B:
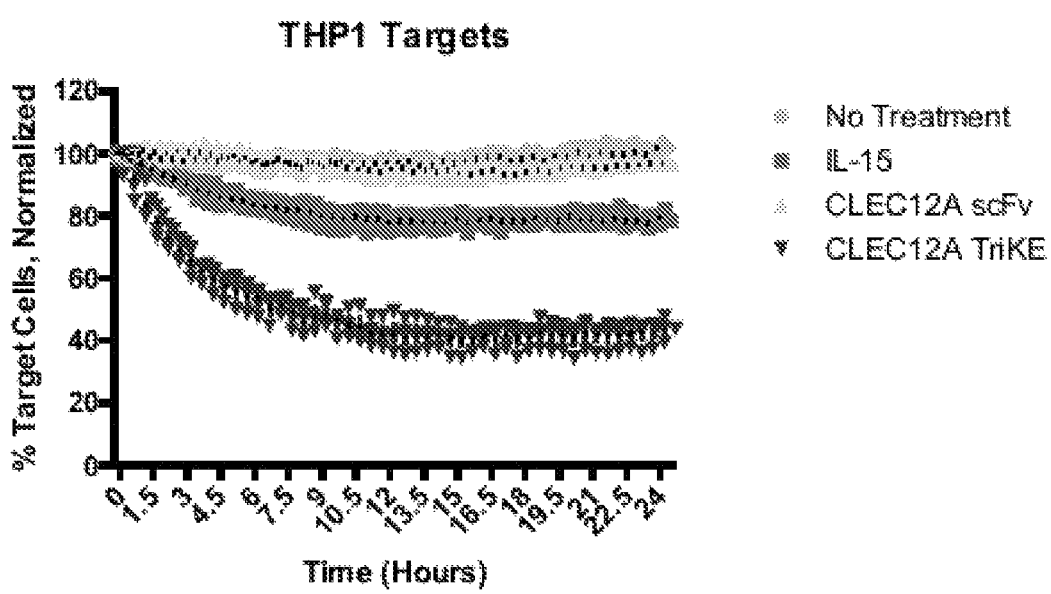

Enriched NK cells were incubated with CLEC12A+ HL-60 (FIG. 7A) and THP1 (FIG. 7B) targets at a 2:1 effector to target ratio in the presence of IL-15, CLEC12A scFv or CLEC12A TriKE at equimolar concentrations. The target cells were labeled with a Cell Trace Far Red dye and a Caspase 3/7 green apoptosis assay reagent (Essen Biosciences). Killing was assessed using an Incucyte Zoom machine and analyzed by normalizing cell numbers to initial number of target cells. Graphs in FIGS. 7A-B depict the following (from the top): (i) no treatment (first from top); (ii) treatment with CLEC12A scFv (second from top); (iii) treatment with IL-15 (third from top/second from bottom); (iv) treatment with CLEC12A TriKE (fourth from top/ bottom). The percentage of live target cells was lowest upon treatment with CLEC12A TriKE.

Figure 11A:
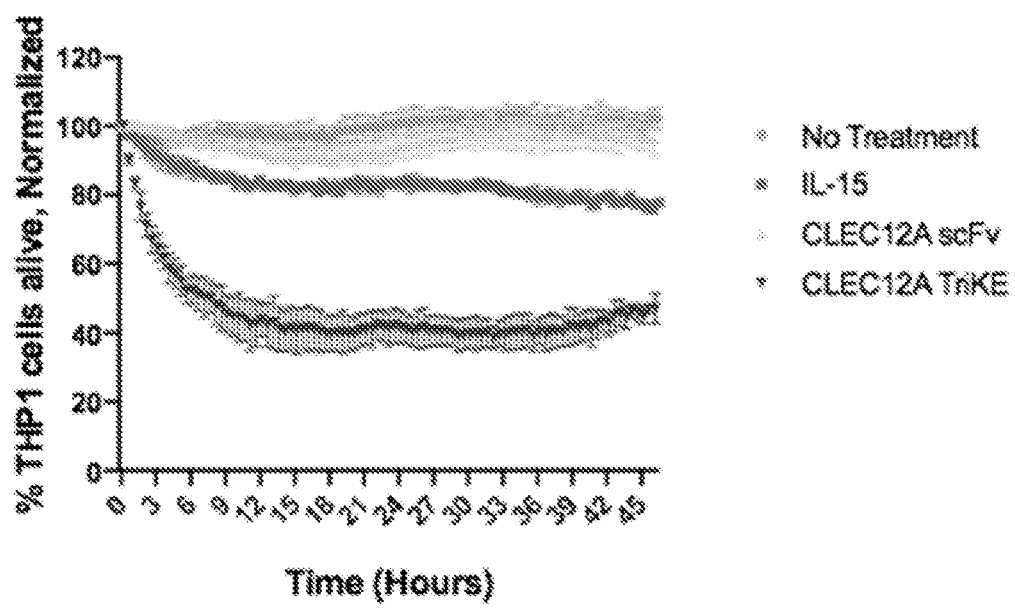
FIGS. 11A-11C illustrate CD16-IL15-CLEC12A TriKE induction of target cell killing in a real-time imaging assay. THP-1 tumor targets are shown.

1615CLEC12A TriKE-mediated induction of target cell killing was evaluated in a real-time imaging assay. Enriched NK cells (CD3−, CD56+) were incubated with CellTrace Far Red labeled THP-1 cells at a 2:1 effector to target ratio with the noted treatments (30 nM) for 48 hours within an IncuCyte S3 imager. Dead THP-1 cells were measured using a Caspase 3/7 reagent. FIG. 11A shows quantification of the percentage of live THP-1 tumor targets (CellTrace Far Red/Caspase 3/7) normalized to targets alone at the 0-hour time point. Readings were taken every 30 minutes over a 48-hour period. Representative of 3 separate experiments. First from top corresponds to no treatment, second from top corresponds to treatment with CLEC12A scFv, third from top corresponds to treatment with IL-15, fourth from top corresponds to treatment with CLEC12A TriKE. The lowest percentage of live THP-1 cells was seen in the presence of CLEC12A TriKE.

Figure 11B:
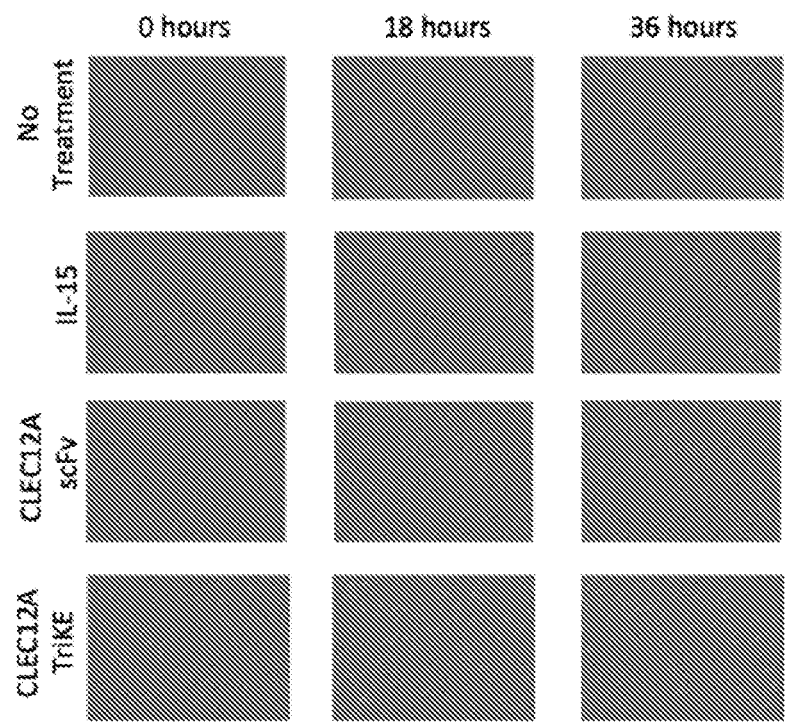

FIG. 11B are representative images (original magnification 34: 2.82 mm/pixel) at 0, 18, and 36 hours showing THP-1 cells (larger cells) and NK cells (smaller cells). At 0 hours, few dead cells were present for all indicated treatment conditions. At 18 and 36 hours, few clusters of dead THP-1 cells were apparent throughout the no treatment and CLEC12A scFv conditions, with some clusters of dying THP-1 cells present for treatment with IL-15 and many more clusters of dying cells present with treatment with CLEC12A TriKE.

Figure 11C:
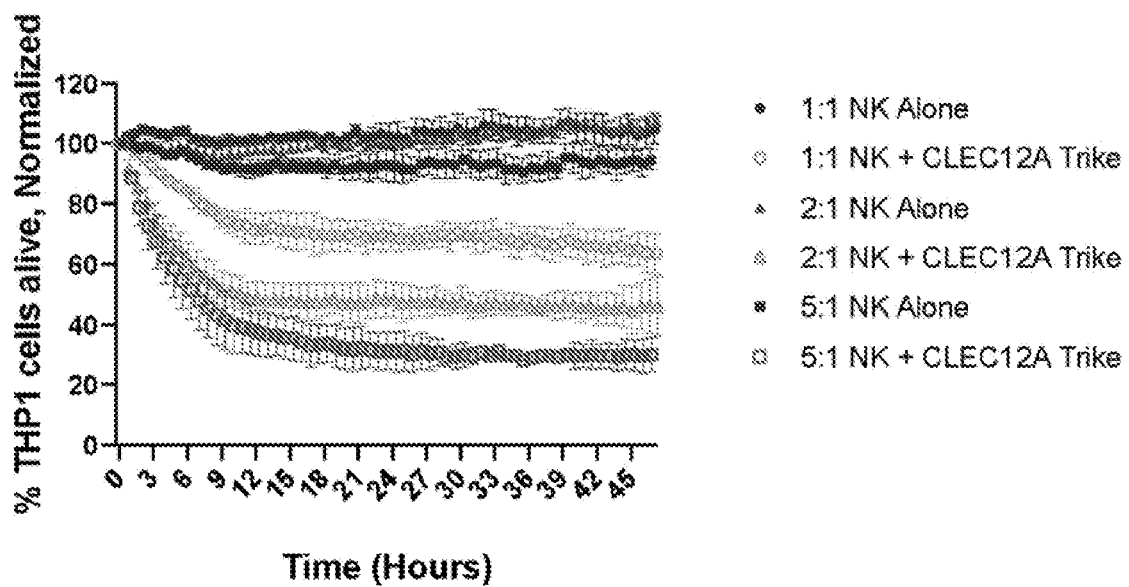

FIG. 11C shows quantification of the percentage of live THP-1 tumor targets at different effector to target rations (1:1, 2:1 and 5:1). First, second and third from top correspond to NK Alone, fourth from top corresponds to 1:1 NK+CLEC12A TriKE, fifth from top corresponds to 2:1 NK+CLEC12A TriKE, sixth from top corresponds to 5:1 NK+CLEC12A TriKE. Lower percentages of live THP-1 cells were seen for all effector to target ratios as compared to NK cells alone, with an effector to target ratio of 5:1 resulting in the lowest percentage of live THP-1 cells, but this decrease in viability of THP-1 cells was maximal when CLEC12A TriKE treatment was present.

In other experiments, enriched NK cells were incubated with CellTrace Far Red labeled HL-60 cells at a 2:1 effector to target ratio with the indicated treatments (30 nM for each) for 48 hours within an IncuCyte s3 imager. Dead HL-60 cells were measured using a Caspase 3/7 reagent.

Figure 15A:
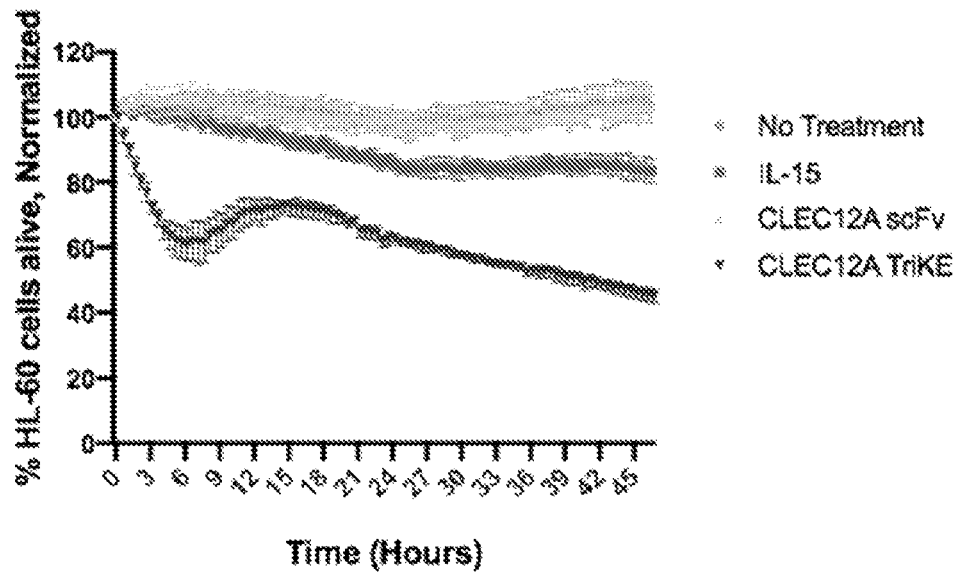
FIGS. 15A-15B illustrate CD16-IL15-CLEC12A TriKE induction of target cell killing in a real-time imaging assay. HL-60 tumor targets are shown.

FIG. 15A shows quantification of the percentage of live HL-60 tumor targets (CellTrace Far Red/Caspase 3/7) normalized to targets alone and the 0-hour time point. Readings were taken every 30 minutes over a 48-hour period. Representative of 3 separate experiments. First from top corresponds to no treatment, second from top corresponds to treatment with CLEC12A scFv, third from top corresponds to treatment with IL-15, fourth from top corresponds to treatment with CLEC12A TriKE. The lowest percentage of live HL-60 cells was seen in the presence of CLEC12A TriKE.

Figure 15B:
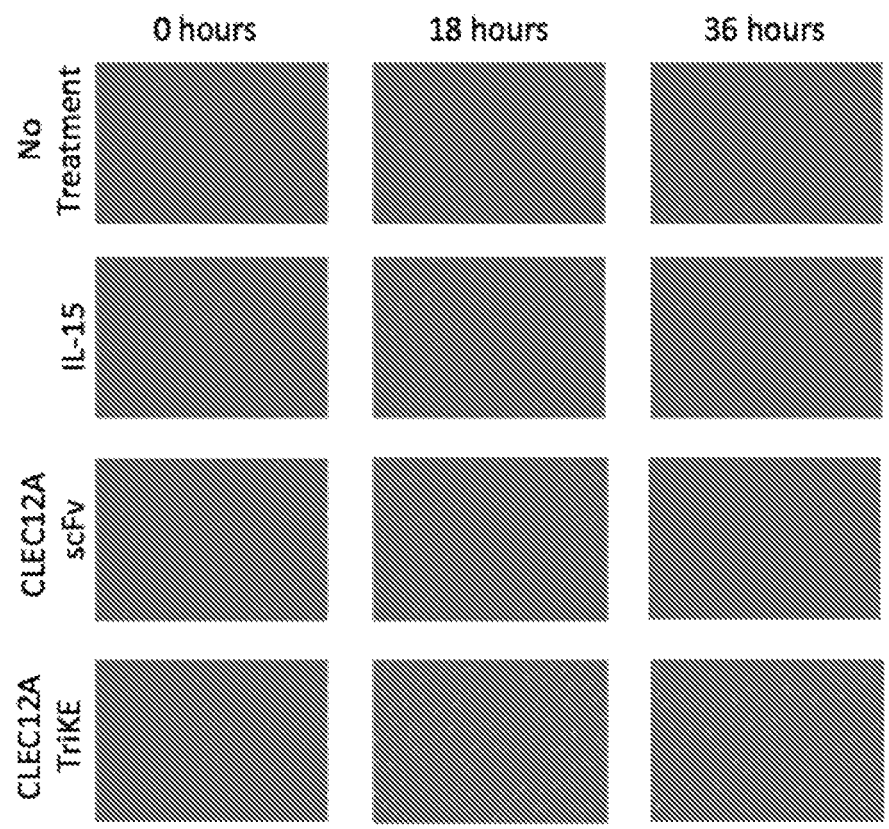

FIG. 15B are representative images at 0, 18, and 36 hours showing HL-60 target cells (larger cells) and NK cells (smaller cells). At 0 hours, few dead cells were present for all indicated treatment conditions. At 18 and 36 hours, few clusters of dead HL-60 cells were apparent throughout the no treatment and CLEC12A scFv conditions, with some clusters of dying HL-60 cells present for treatment with IL-15 and many more clusters of dying cells present with treatment with CLEC12A TriKE.

These data show that the CD16-IL15-CLEC12A TriKE induced killing of AML targets, including THP-1 and HL-60 target cells.

Example 8

This example illustrates CD16-IL15-CLEC12A TriKE-induced killing of primary AML blast targets in vitro.

Figure 8A:
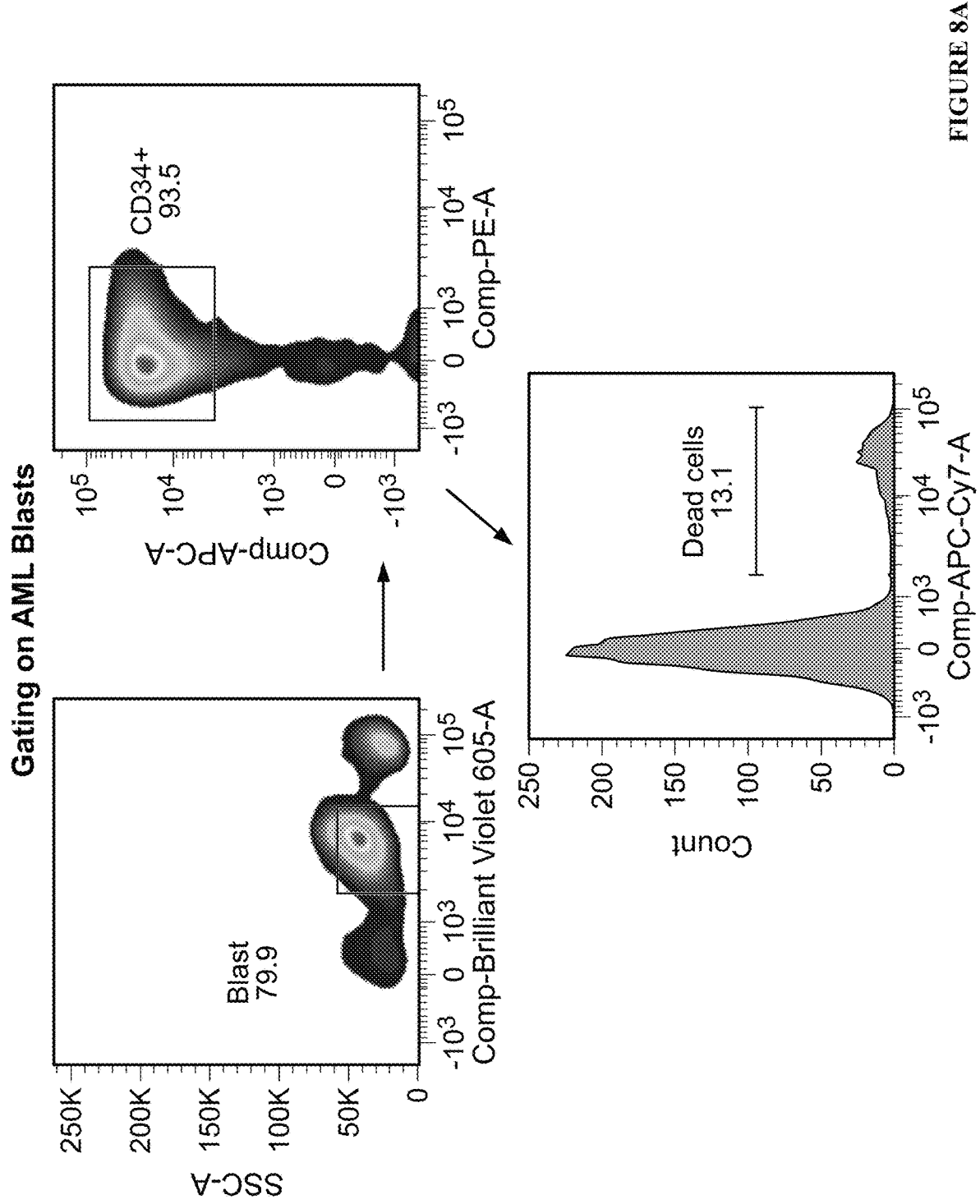
FIGS. 8A-8D illustrate CD16-IL15-CLEC12A TriKE induced killing of primary AML targets in vitro.
Figure 8B:
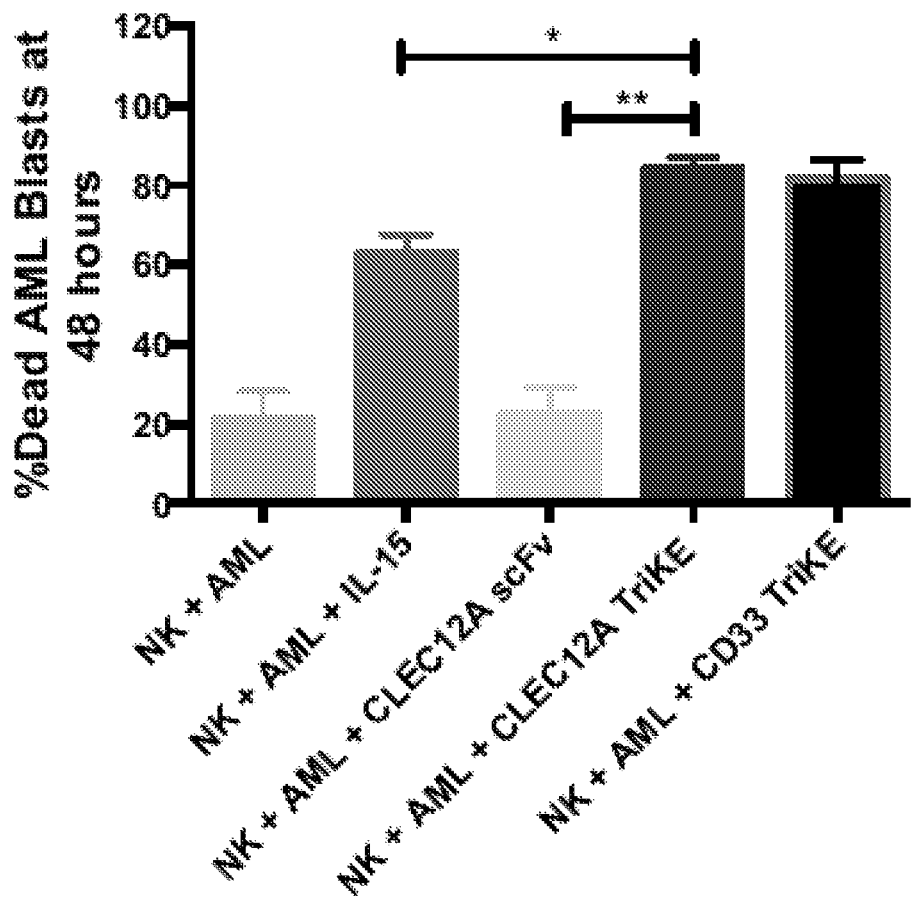
Figure 8C:
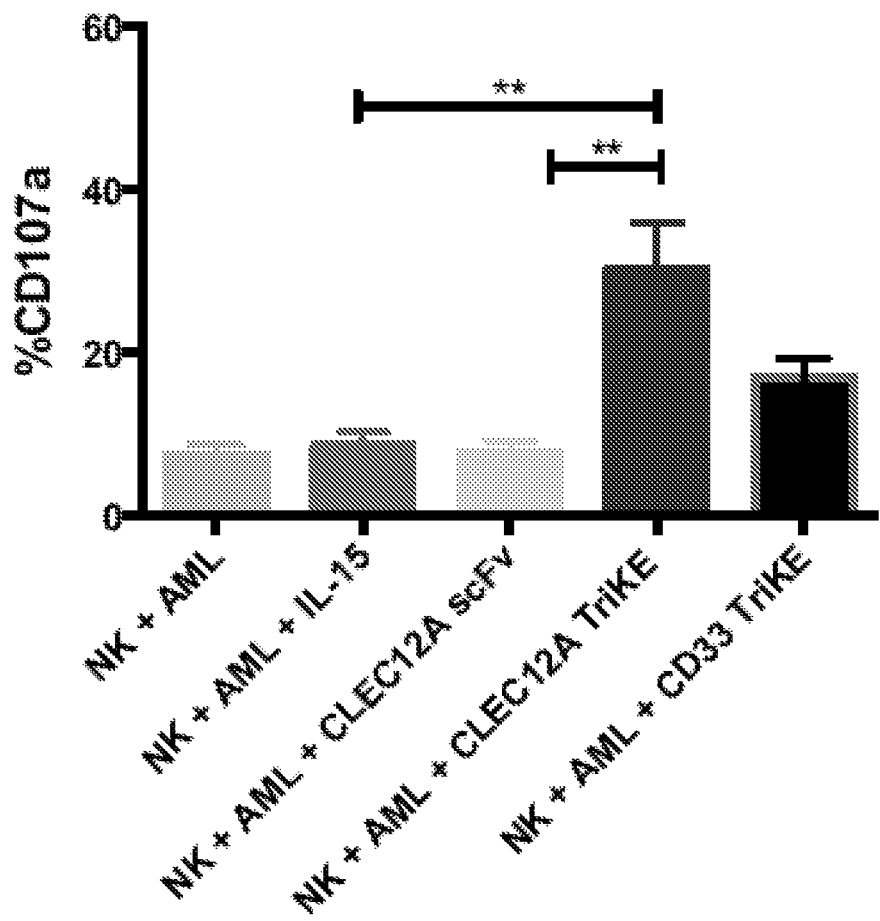
Figure 8D:
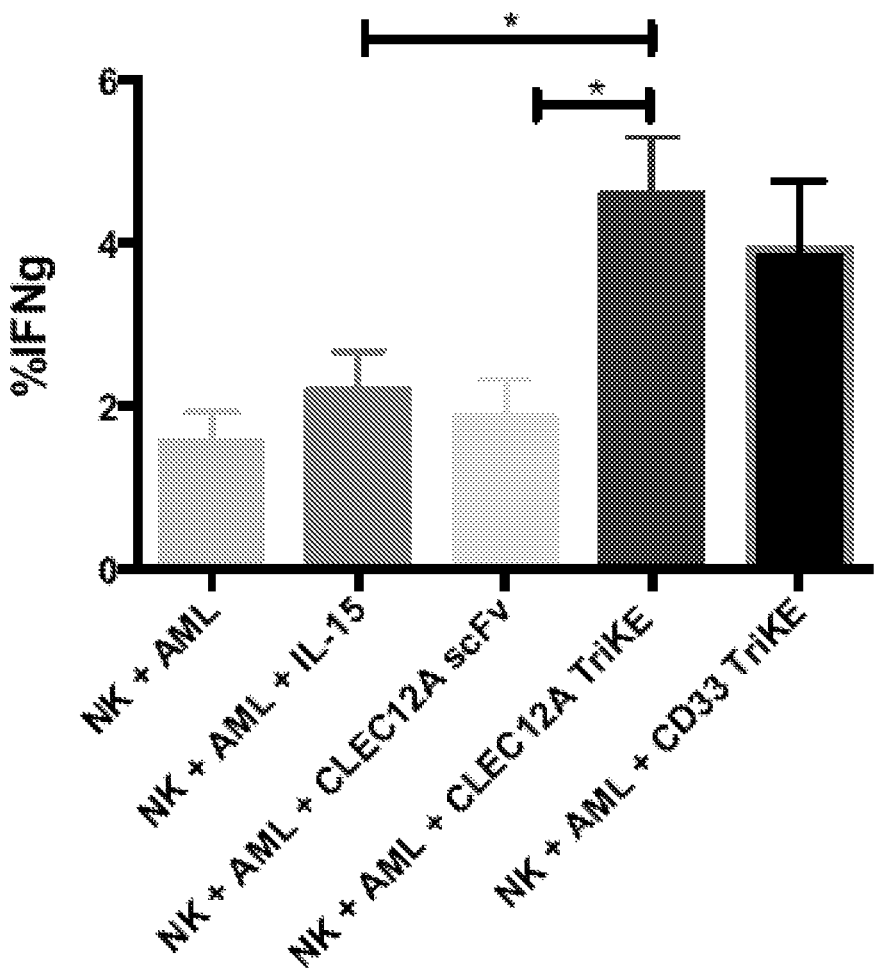

Enriched NK cells were incubated with primary AML blasts at a 2:1 effector to target ratio in the presence of IL-15, CLEC12A scFv, CLEC12A TriKE or CD33 TriKE at equimolar concentrations. FIG. 8A shows the gating scheme to identify AML blasts using FlowJo Analyzer. FIG. 8B shows the percentage of killing of AML blasts as assessed by the live/dead marker after gating on blasts cells after 48 hours. Surface CD107a expression to evaluate degranulation (FIG. 8C) and intracellular IFNg to evaluate inflammatory cytokine production (FIG. 8D) were assessed on CD56+CD3− NK cells by flow cytometry after 4 hours. Statistics reflect significant differences between the groups as calculated with a One Way ANOVA, *P<0.05 **P<0.005, N=10. The percentage of dead AML blast cells and percentages of staining for CD107a and IFNg were significantly greater upon incubation with CLEC12A TriKE as compared to incubation with IL-15 or incubation with CLEC12A scFv (FIGS. 8B-D).

Figure 12A:
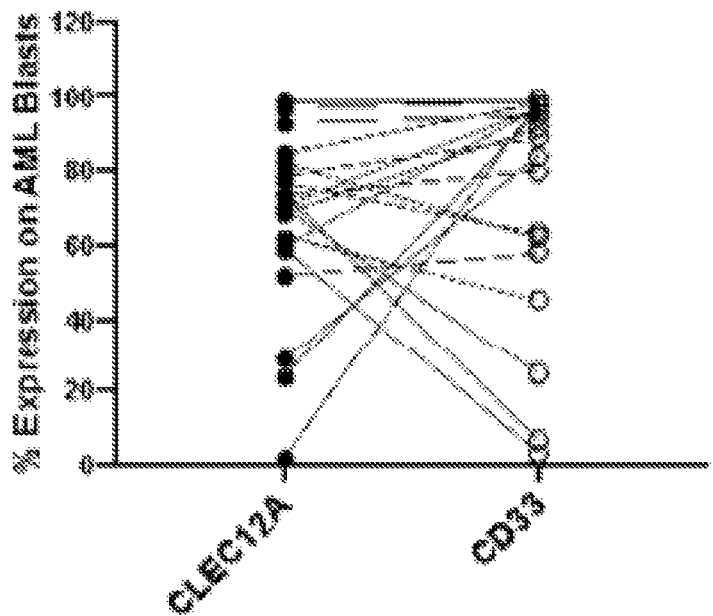
FIGS. 12A-12G illustrate CD16-IL15-CLEC12A TriKE-induced killing of primary AML blasts.

In other experiments, primary AML blasts (SSCh low, CD45int, CD117+, CD14−, CD34+) were assessed for expression of CD33 and CLEC12A using flow cytometry (FIG. 12A). Cells expressed CD33, CLEC12A, or both CD33 and CLEC12A as shown.

Figure 12B:
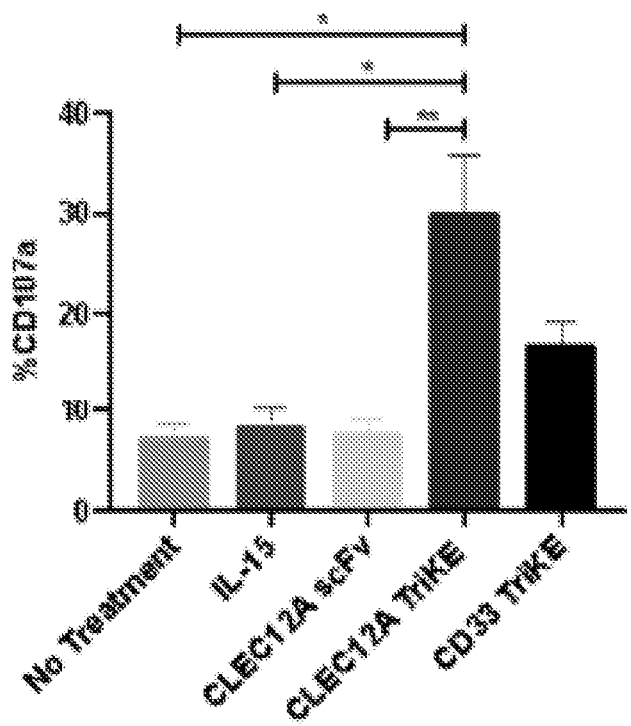
Figure 12C:
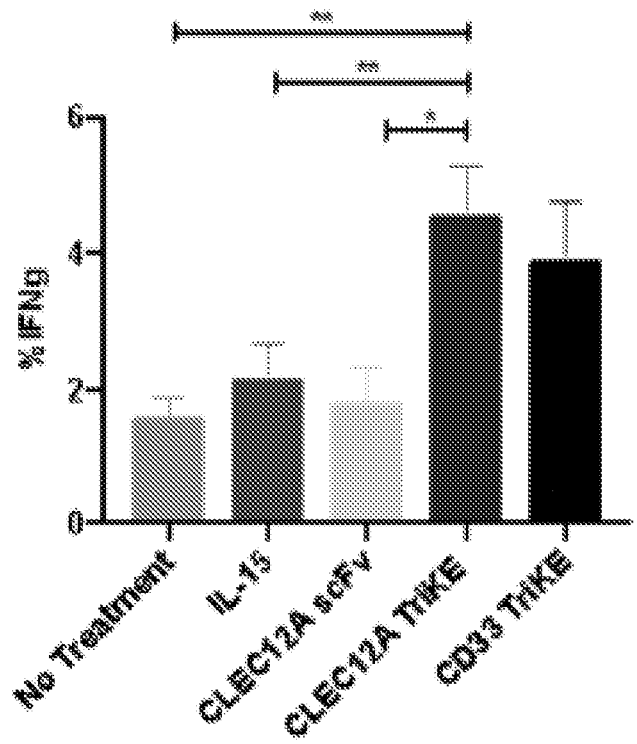
Figure 12D:
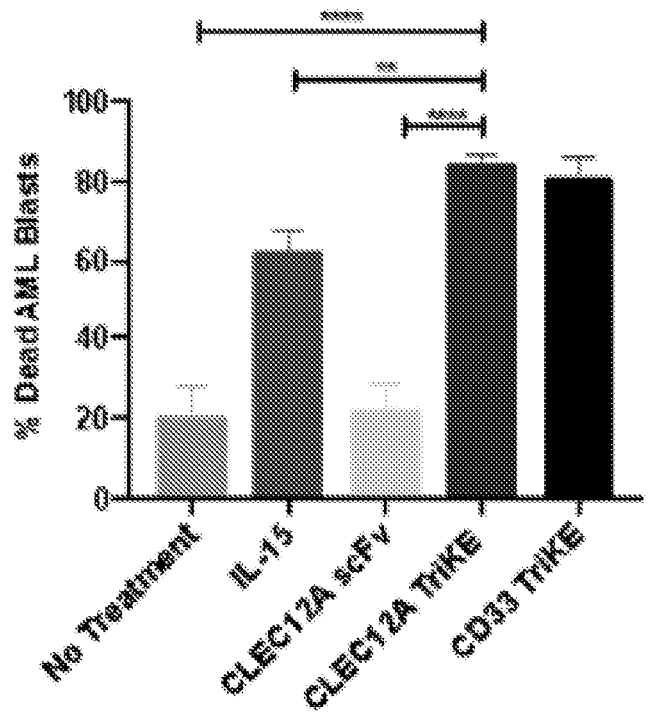

Enriched NK cells (CD56+, CD3−) from healthy donors (n=10) were incubated with primary AML blasts with the indicated treatments (30 nM) to evaluate CD107a expression as a marker of degranulation (FIG. 12B) and intracellular IFNg production (FIG. 12C) in a 4-hour assay at a 2:1 effector/target ratio. CLEC12A TriKE and CD33 TriKE induced degranulation and IFNg production as shown. Target cell killing was also evaluated using flow cytometry and a live/dead marker over 48 hours (FIG. 12D). Treatment with IL-15, CLEC12A TriKE, and CD33 TriKE resulted in killing of AML blast cells as shown, with greater CLEC12A TriKE-mediated killing.

Figure 12E:
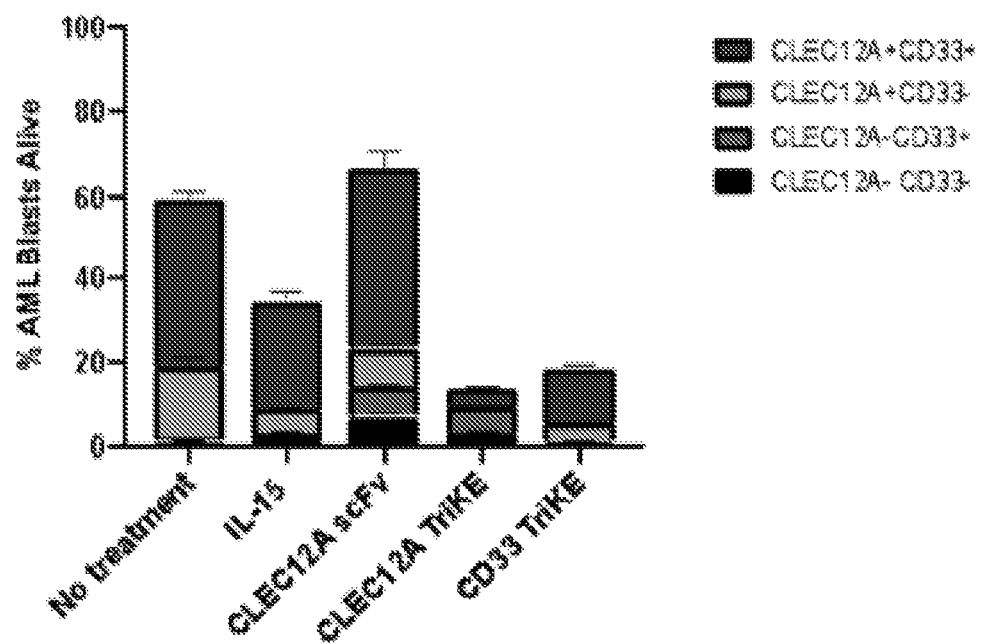

The proportion of different groups of AML blasts (based on CD33 and CLEC12A expression) were tracked over 48 hours to assess specificity of the 1615CLEC12A TriKE compared to the 1615CD33 TriKE (FIG. 12E). Bars showing % AML blasts alive correspond to the following (from the top of each bar): (i) for no treatment, CLEC12A+CD33+ and CLEC12A+CD33−; (ii) for IL-15, CLEC12A+CD33+, CLEC12A+CD33−, and CLEC12A−CD33−; (iii) for CLEC12A scFv, CLEC12A+CD33+, CLEC12A+CD33−, CLEC12A−CD33+, and CLEC12A−CD33−; (iv) for CLEC12A TriKE, CLEC12A+CD33+, CLEC12A−CD33+, and CLEC12A−CD33−; (v) for CD33 TriKE, CLEC12A+CD33+ and CLEC12A+CD33−. These data confirm specificity of the 1615CLEC12A TriKE compared to the 1615CD33 TriKE.

Figure 12F:
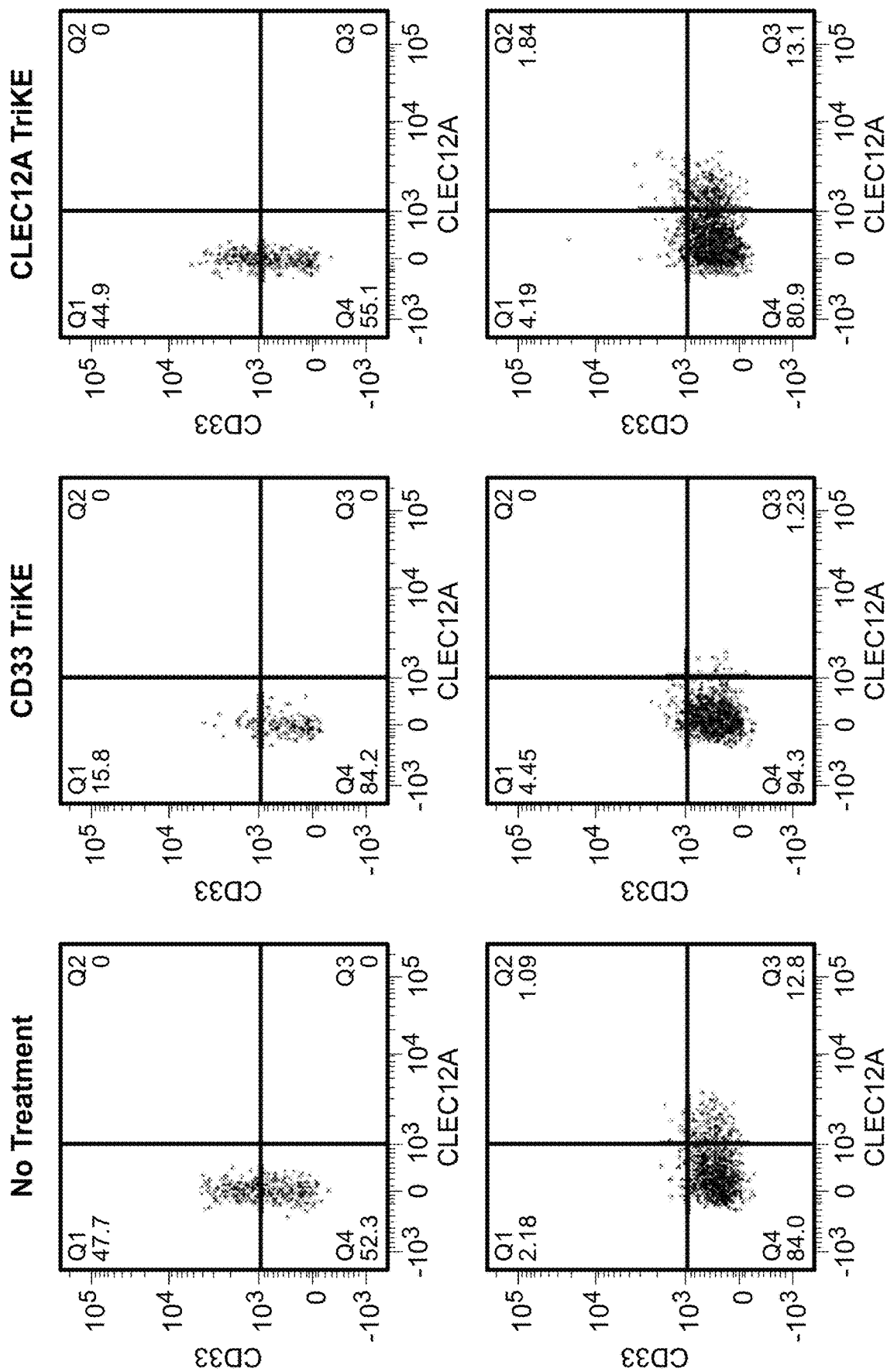

In other experiments, enriched NK cells (CD56+, CD3−) from healthy donors (n=5) were incubated with bone marrow samples from AML patients with the indicated treatments (30 nM) to evaluate killing of cancer stem cells (SSCh low, CD45int, CD34+, CD38−) in a 4-hour assay at a 2:1 effector/target ratio (FIG. 12F). Representative flow plots show killing of CLEC12A and CD33 positive cancer stem cells.

Figure 12G:
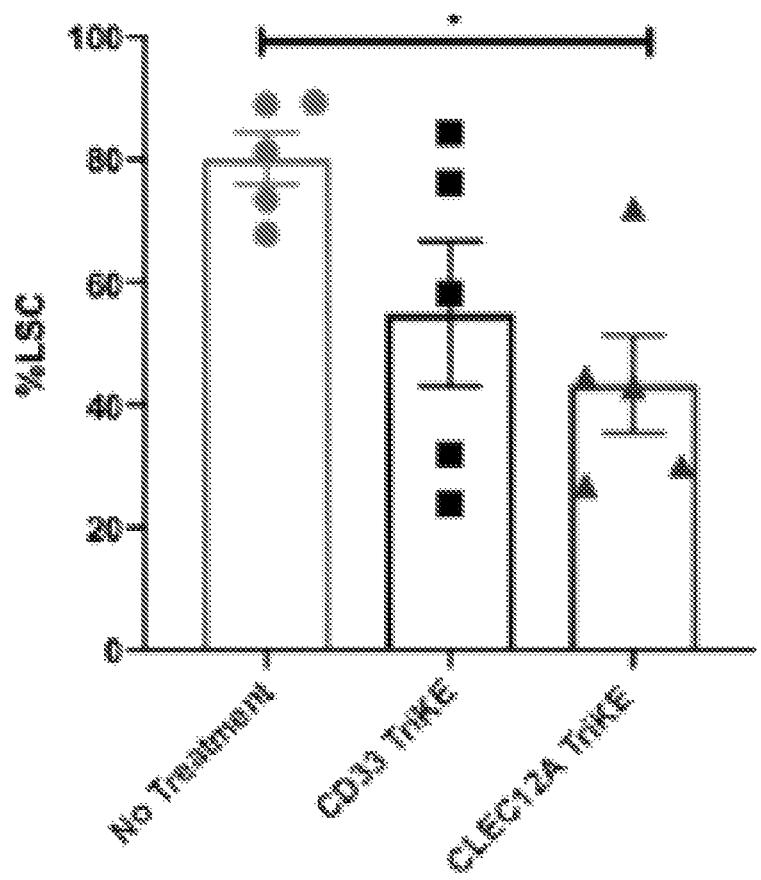

FIG. 12G shows combined data from the cancer stem cell killing assay showing percentage of cancer stem cells present at the end of the assay. One-way analysis of variance (ANOVA) with repeated measures was used to calculate differences against the 1615CLEC12A group. Error bars indicate +/−standard error of the mean. Statistical significance are determined as *P, 0.05, P, 0.01, *P, 0.001, and ****P, 0.0001. Treatment with CLEC12A TriKE resulted in significantly lower percentages of LSC compared to no treatment.

Figure 16A:
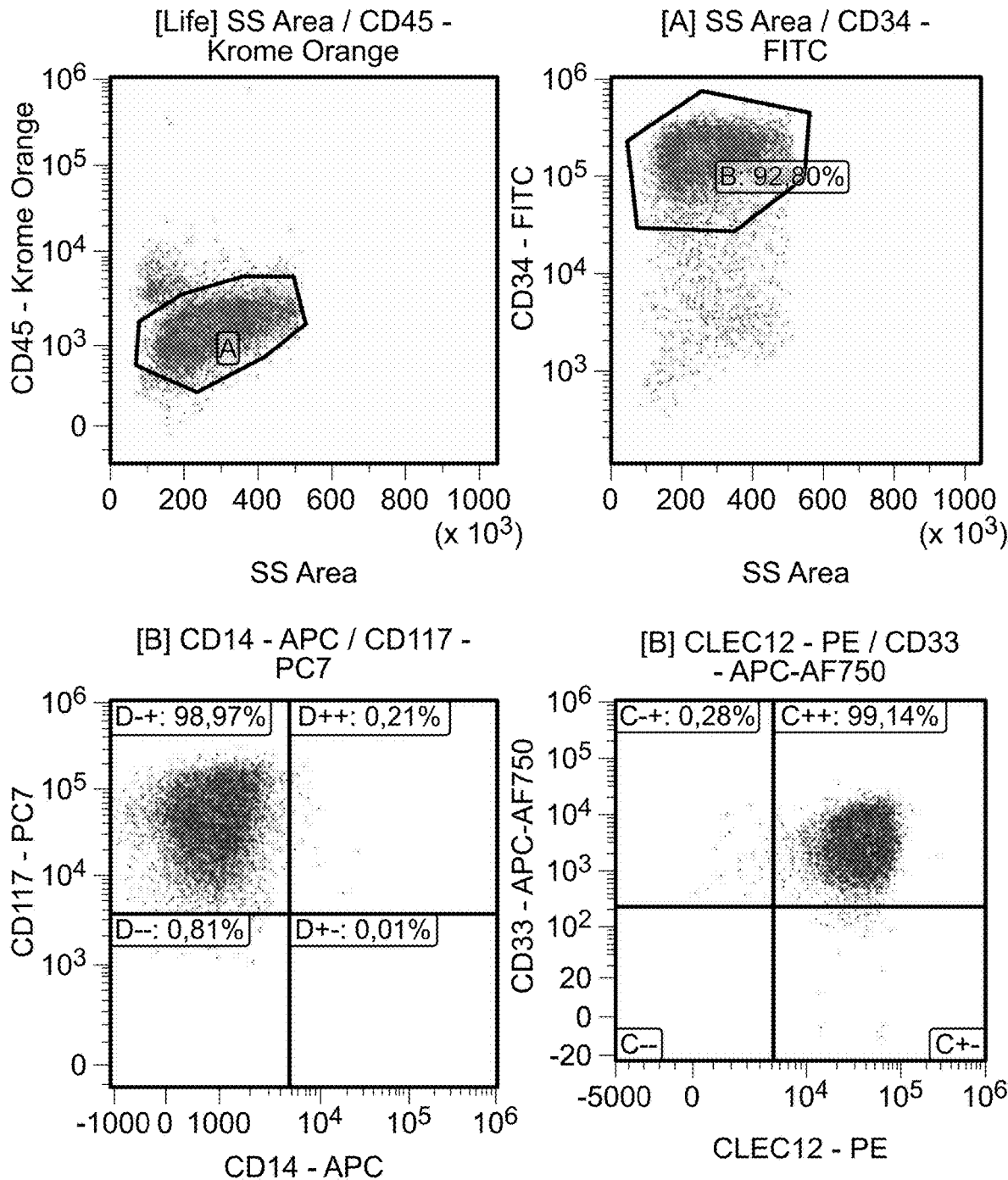
FIGS. 16A-16B illustrate CD16-IL15-CLEC12A TriKE-mediated target killing. Target gating strategy (FIG. 16A) and target cell killing (FIG. 16B) are shown. AML blast targets are shown.
Figure 16B:
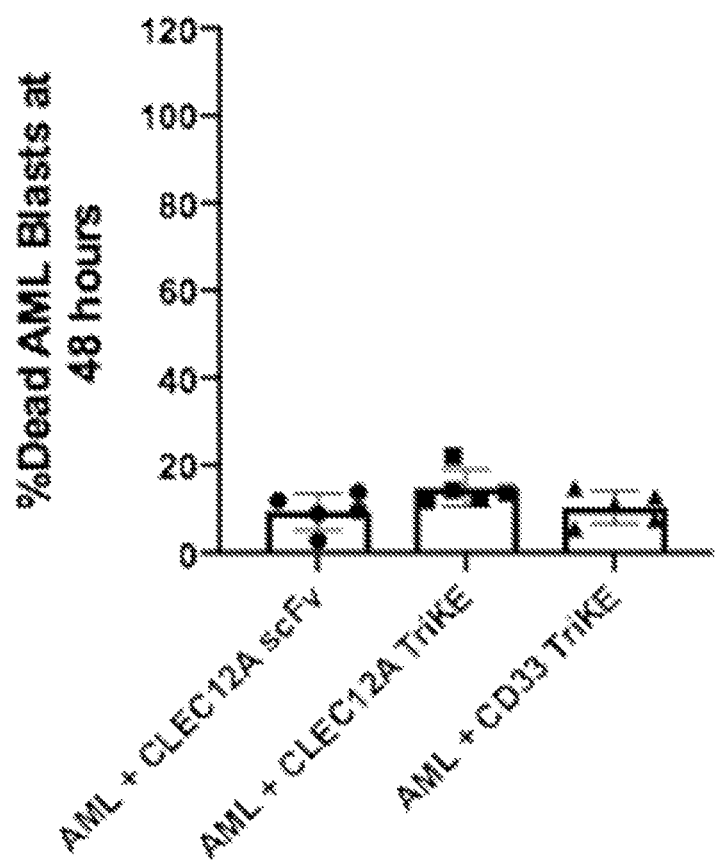

To examine primary AML blasts as target cells for killing mediated by the CLEC12A TriKE, a gating strategy was employed. The gating strategy to identify primary AML blasts is shown in FIG. 16A. Primary AML blasts (n=5) were then incubated with the indicted treatments (30 nM) to evaluate target cell killing using flow cytometry and a live/dead marker over 48 hours (FIG. 16B). The percentage of dead AMP blasts at 48 hours is shown.

These data show that the 1615CLEC12A TriKE induced a slight increase in killing of primary AML blasts in patient samples at blast crisis, where NK cells are limiting.

Example 9

This example describes 1615CLEC12A TriKE-mediated limitation of tumor growth in vivo.

Figure 13A:
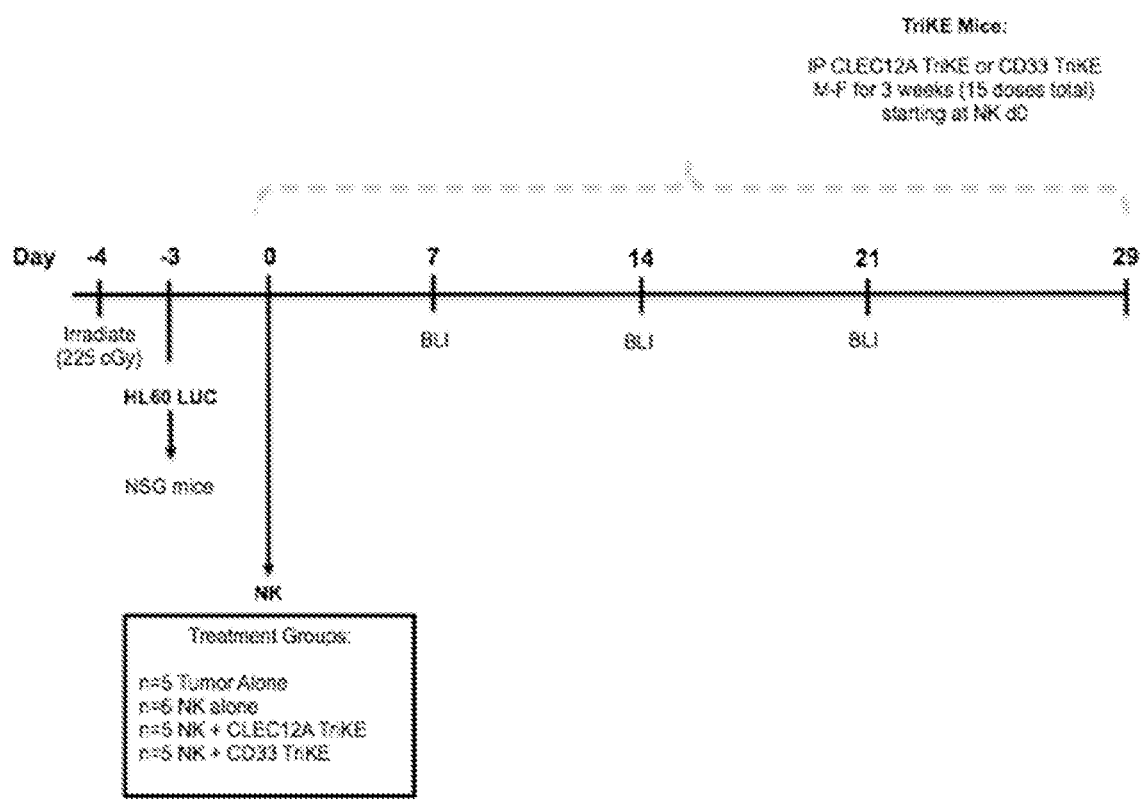
FIGS. 13A-13G illustrate that CD16-IL15-CLEC12A TriKE limits tumor growth in vivo.

FIG. 13A shows a schematic of HL-60luc mouse experiments. The model was established by conditioning NSG mice (225cGy) and then injecting HL-60luc cells intravenously (7.5×105 cells/mouse). Three days later, 1×10$^6$ normal human donor NK cells (calculated from a magnetically depleted CD3/CD19 product) activated overnight with 10 ng/ml IL-15 were infused. The 1615CLEC12A TriKE or 161533 TriKE (20 ug) was administered MTWThF through the next 3 weeks of the study (15 doses total), and a control group only received HL-60luc cells.

Figure 13B:
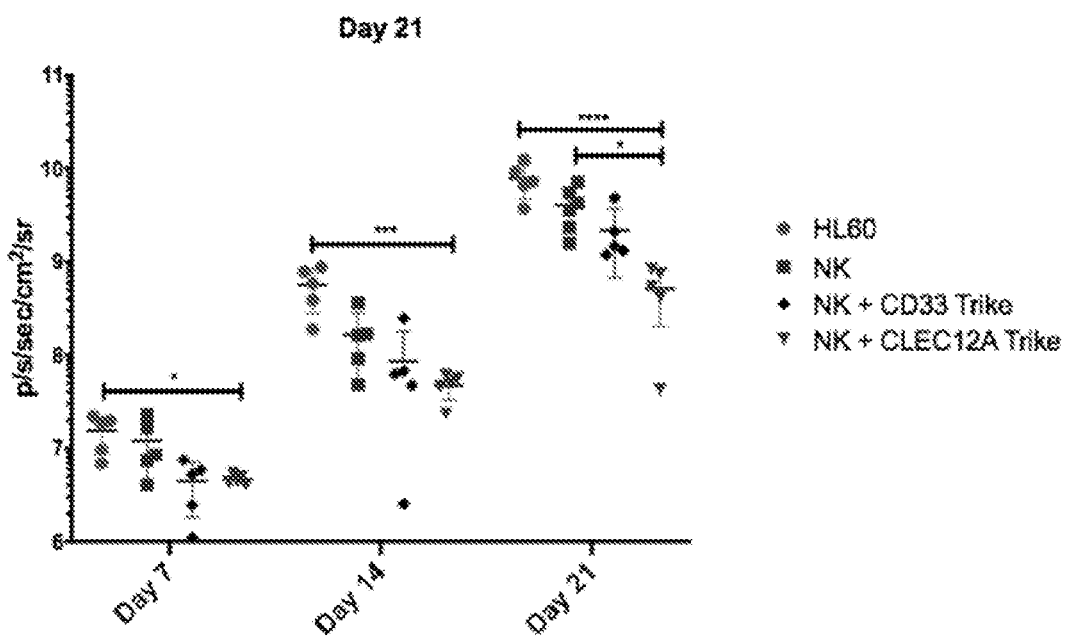
Figure 13C:
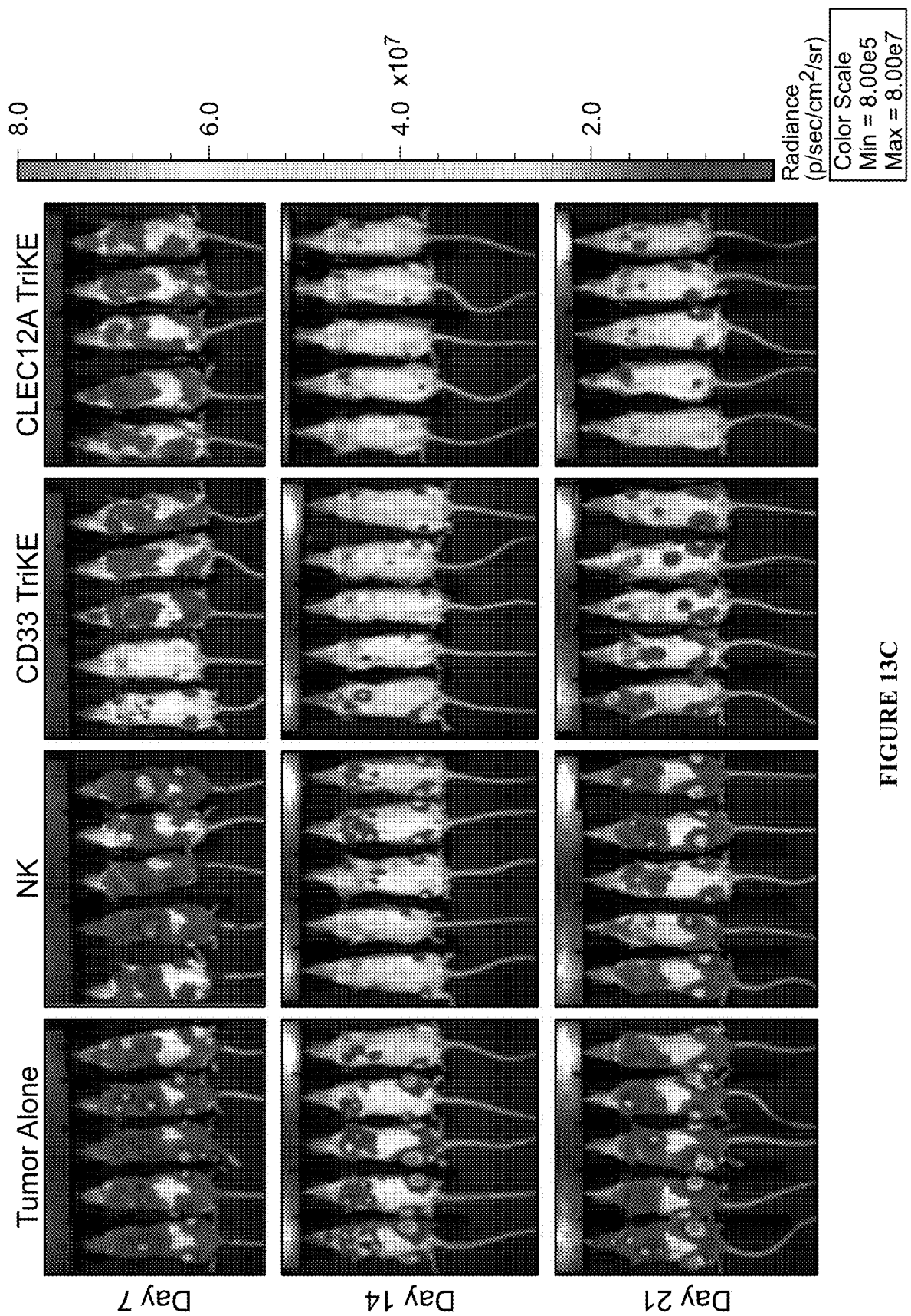

Quantification of luminescence from the four treatment groups at day 7, day 14 and day 21 after NK infusion are shown in FIG. 13B. Each dot represents a different mouse and bars denote mean+/−Standard Deviation. One-way analysis of variance (ANOVA) without matched comparisons was used to calculate differences against the 1615CLEC12A group. Statistical significance was determined as *P, 0.05, *P, 0.001, and **P, 0.0001. FIG. 13C shows individual mouse photoluminescence (dark regions) after 2-minute exposures on day 7, 14 and 21. CLEC12A TriKE treatment resulted in decreased tumor burden at all time points examined compared to HL60 control. In addition, a significant reduction in tumor burden upon CLEC12A TriKE treatment relative to NK cell control treatment was seen at day 21.

Figure 13D:
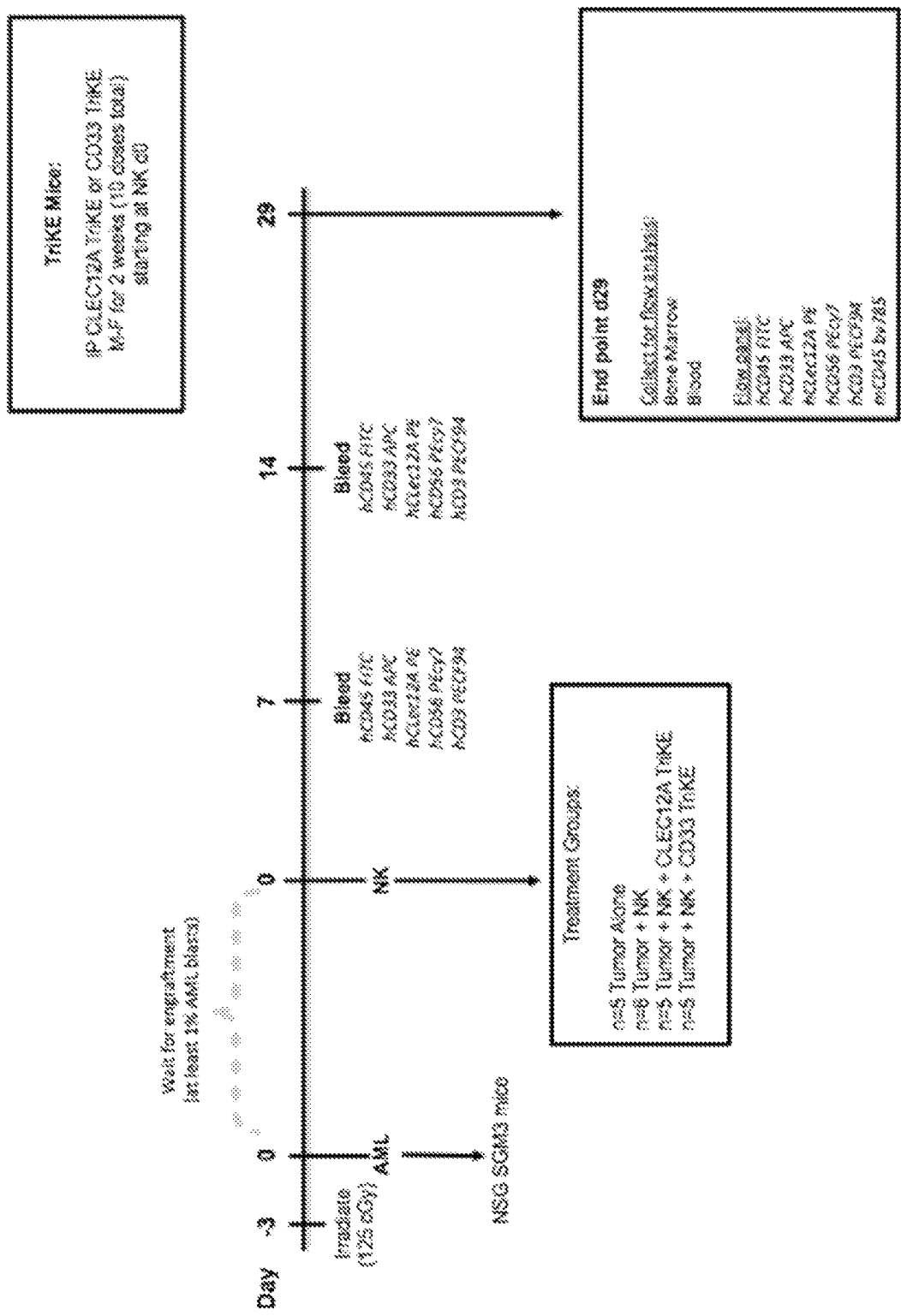
Figure 13E:
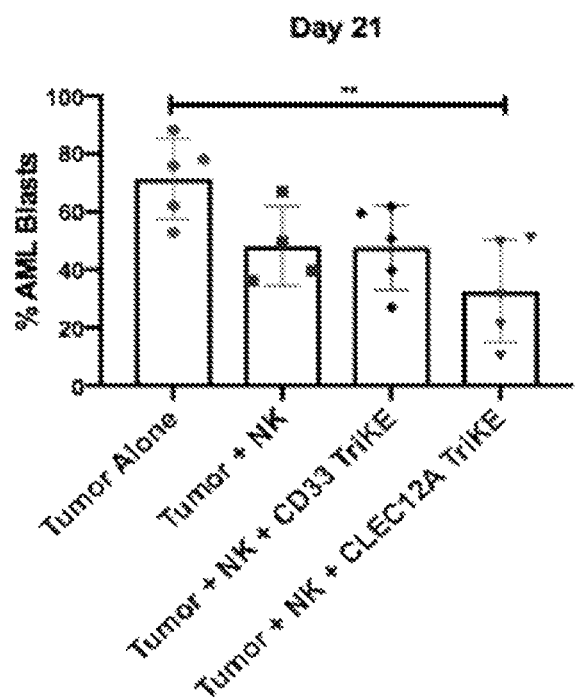
Figure 13F:
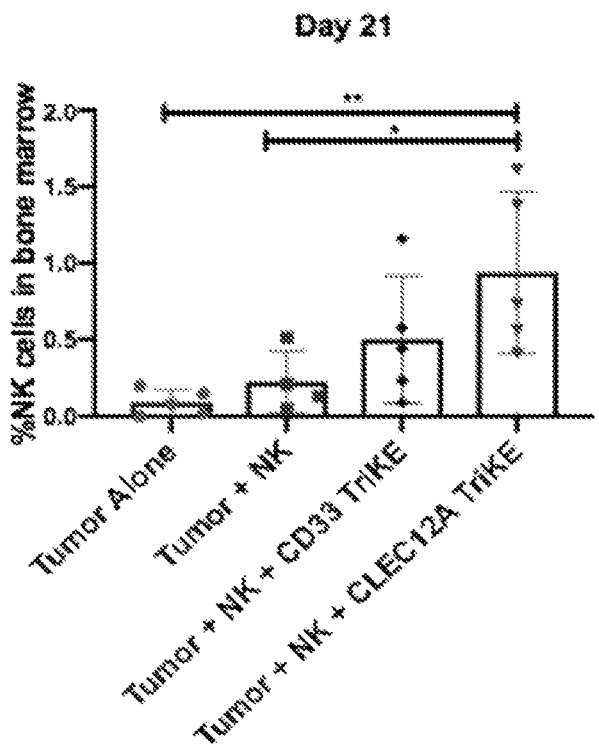
Figure 13G:
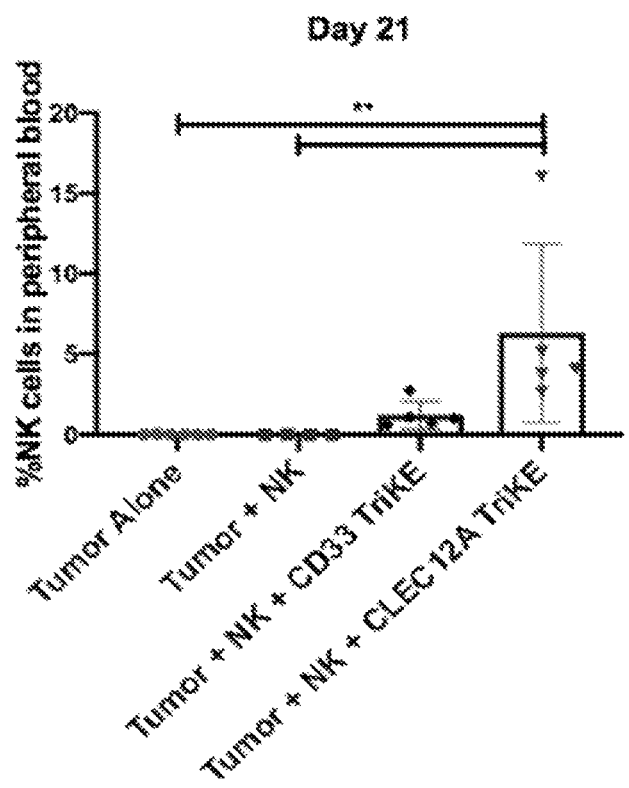

FIG. 13D shows a schematic of pdx mouse experiments. The model was established by conditioning NSG SGM3 mice (125cGy) and then injecting HL-60luc cells intravenously (7.5×10$^5$ cells/mouse). Tumors were allowed to grow until there were at least 1% AML Blasts in the blood. Then 1×10$^6$ normal human donor NK cells (calculated from a magnetically depleted CD3/CD19 product) activated overnight with 10 ng/ml IL-15 were infused. The 1615CLEC12A TriKE or 161533 TriKE (20 ug) was administered MTWThF for the next 3 weeks of the study (15 doses total) and a control group received NK cells but no treatment. The mice were sacrificed on day 21 and the percentage of AML blasts (CD45int, CD33+) in the bone marrow from the femur was calculated by flow cytometry (FIG. 13E). Each dot represents a different mouse. The percentage of NK cells (CD3−, CD56+) was calculated in the bone marrow samples (FIG. 13F) and peripheral blood (FIG. 13G) by flow cytometry. Events were collected over 60 seconds and the number of human NK cell events was calculated. Representative dot plots are shown denoting the number of NK (CD56+CD3−) cell events within the CD45+ gate). One-way analysis of variance (ANOVA) without matched comparisons was used to calculate differences against the 1615CLEC12A group. Error bars denote mean+/−Standard Deviation. Statistical significance was determined as *P, 0.05, *P, 0.001, and **P, 0.0001. Results show that NK+CLEC12A TriKE treatment significantly decreased the percentage of primary AML blast cells compared to tumor alone (FIG. 13E). In addition, NK+CLEC12A TriKE treatment resulted in significantly increased percentages of NK cells in bone marrow (FIG. 13F) and peripheral blood (FIG. 13G) compared to tumor alone or tumor+NK treatment.

Taken together, these results show that 1615CLEC12A TriKE limited tumor growth in vivo.

Example 10

This example describes analysis of stem and progenitor cells.

Figure 17:
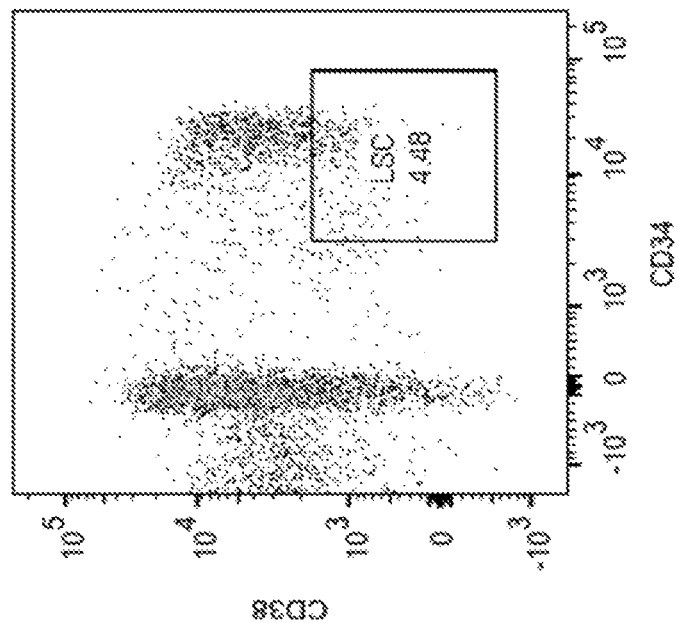
FIG. 17 illustrates a gating strategy to identify cancer stem cells in bone marrow samples from AML patients.
Figure 17:
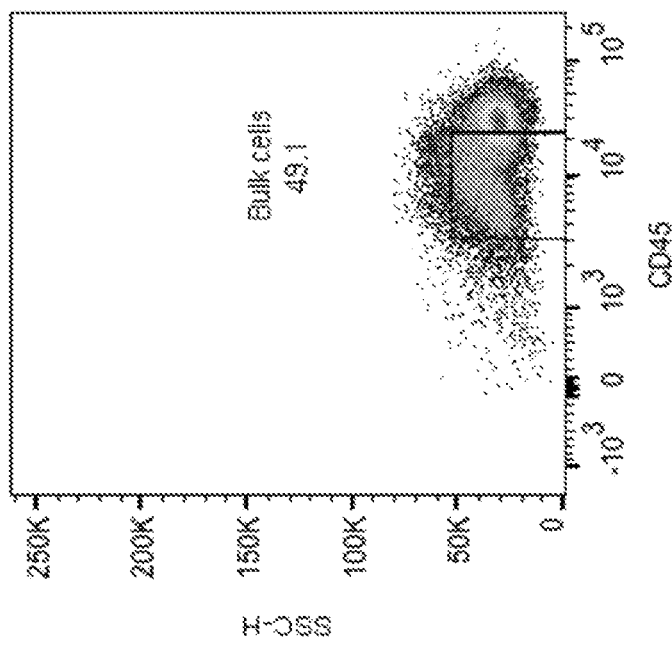

Cancer stem cells were identified in bone marrow samples using the gating strategy shown in FIG. 17. A gating strategy to determine different CD34$^{pos}$ progenitor subpopulations in healthy bone marrow samples is shown in FIG. 19. The gating strategy shown in FIG. 19 was used to analyze cell populations shown in FIG. 18A.

Figure 18A:
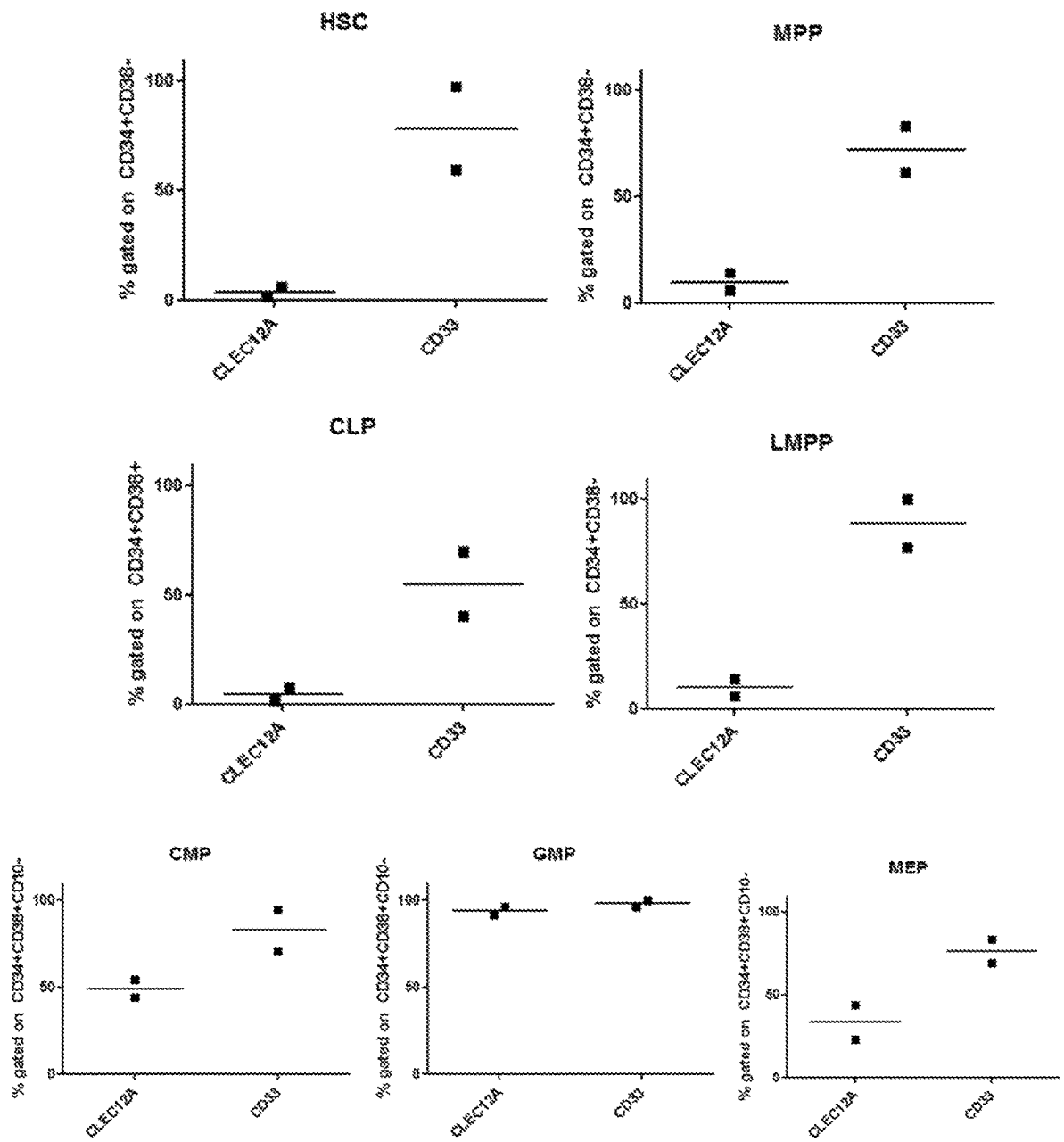
FIGS. 18A-18B illustrate CLEC12A and CD33 expression within the CD34pos progenitor compartment in bone marrow. Cell populations from two representative donors (FIG. 18A) and cell colonies after treatment with the indicated TriKE (FIG. 18B) are shown.
Figure 18B:
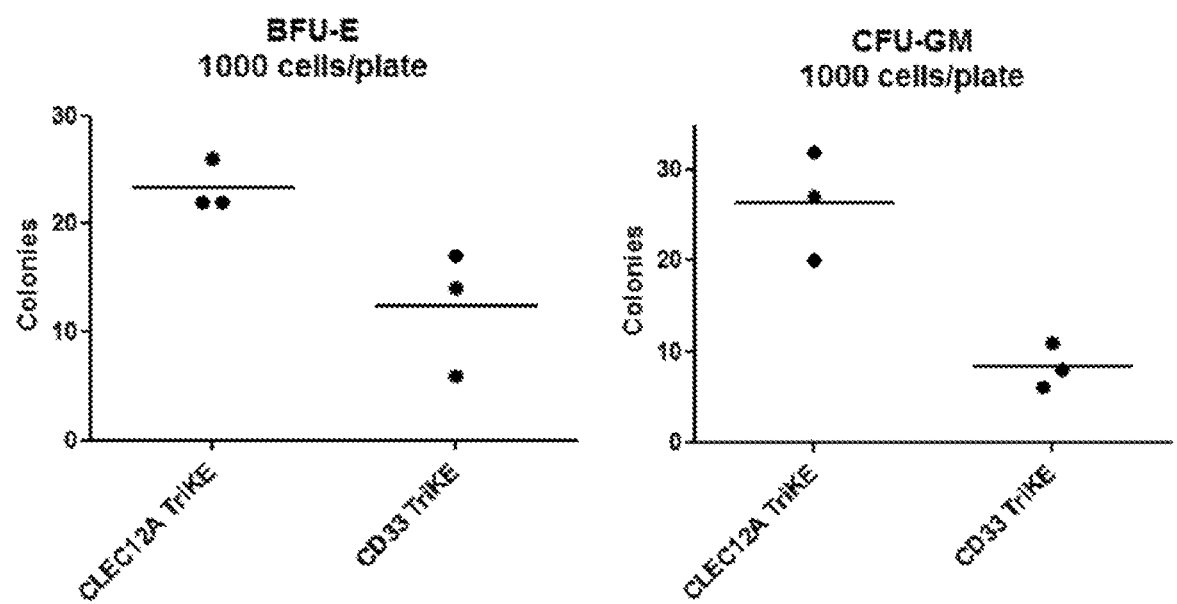
Figure 19:
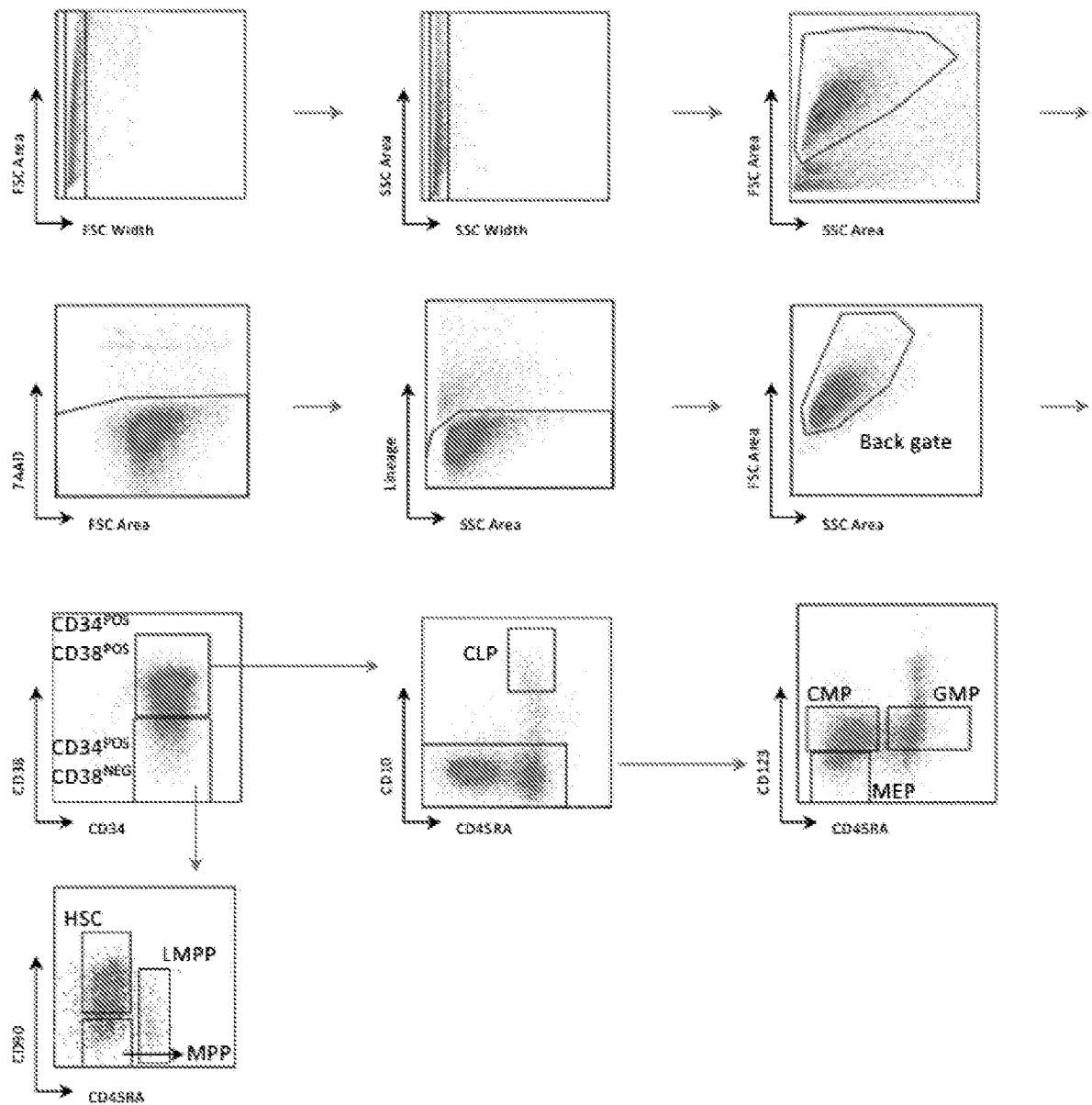
FIG. 19 illustrates a gating strategy to determine different CD34pos progenitor subpopulations in healthy bone marrow samples.

FIG. 18A shows CLEC12A and CD33 expression within the CD34$^{pos}$ progenitor compartment in bone marrow from two representative healthy donors. HSC: hematopoietic stem cell, MPP: multipotent progenitor, LMPP: lymphoid-primed multipotent progenitor, CLP: common lymphoid progenitor, CMP: common myeloid progenitor, GMP: granulocyte-macrophage progenitor, MEP: megakaryocyte-erythroid progenitor. CLEC12A expression was seen in CMP, GMP, and MEP populations, but was relatively lower in HSC, MPP, CLP and LMPP populations. In addition, with the exception of the GMP population, CLEC12A was found at lower levels than CD33. Burst-forming unit-erythroid (BFU-E) and colony-forming unit-erythroid (CFU-E) colonies were counted after treatment with the 1615CLEC12A TriKE or the 161533 TriKE (FIG. 18B). Greater BFU-E and CFU-GM colony numbers were seen upon treatment with 1615CLEC12A TriKE as compared to treatment with 161533 TriKE.

The data show that CLEC12A was differentially expressed in normal donor stem and progenitor cell populations and that treatment with 161533 TriKE decreased stem cell formation and/or differentiation compared to treatment with CLEC12A TriKE. Without being limited by theory, this indicates that while CLEC12A can be used to target leukemic stem cells, it should allow for normal hematopoietic reconstitution, while CD33 targeting is more likely to impact reconstitution. In other words, CLEC12A targeting should have less off target effects in terms of normal myeloid reconstitution.

In summary, taken together, the above data show that the CD16-IL15-CLEC12A TriKE bound specifically to target cells expressing CLEC12A, promoted proliferation of NK cells, enhanced the function of NK cells, promoted killing of AML cell lines in Incucyte zoom assays, and induced killing of primary AML and MDS blasts.

Example 11

This example illustrates the generation of a TetraKE targeting CLEC12A and a second target or tumor antigen.

A TetraKE (tetramer) molecule can be designed that includes more than one targeting domain. As an example, a TetraKE can include a NK engaging domain, an NK activating domain and two targeting domains. Any of the NK engaging domains and NK activating domains described herein can be used. The targeting domains can target different targets or tumor antigens, for example. Any combination of targets or tumor antigens can be included in the TetraKE. For example, a first targeting domain can bind to CLEC12A, while a second targeting domain can bind to another target or tumor antigen.

Any of the targets or tumor antigens described herein can be included in a TetraKE with a first targeting domain that binds to CLEC12A, including, for example, a second targeting domain that binds to CD133, CD20, HER2, CEA, EpCAM, VEGF-A, EGFR, CD33, integrin αVβ3, CD51, CD152, CD125, CTAA16.88, MUC1, CD19, CD22, CD38, mesothelin, ROR1, CSPG4, SS1, or IGFR1, NKG2C, BCMA, APRIL, B7H3, and PSMA, or a viral antigen derived from EBV, HBV, HCV, and/or HPV. Further, TetraKE domains can be operably linked to each other using flanking or linker sequences as described herein. An exemplary TetraKE includes a compound that has a moiety that selectively binds to CD16, an NK activating domain that comprises IL-15, a first targeting domain selectively binds to CLEC12A, and a second targeting domain that selectively binds to CD33.

```
                                                            SEQ ID NO.: 1
MKWVTFISLLFLFSSAYSQVQLVESGGGLVQPGGSLRLSCAASGLTFSSYNMGWFRQAPGQ

GLEAVASITWSGRDTFYADSVKGRFTISRDNSKNTLYLQMNSLRAEDTAVYYCAANPWPVA

APRSGTYWGQGTLVTVSSSGGGGSGGGGSGGGGSGGGGSGNWVNVISDLKKIEDLIQSMHI

DATLYTESDVHPSCKVTAMKCFLLELQVISLESGDASIHDTVENLIILANNSLSSNGNVTE

SGCKECEELEEKNIKEFLQSFVHIVQMFINTSGSTSGSGKPGSGEGSTKGQVQLQESGPGL

VKPSETLSLTCVVSGGSISSSNWWSWVRQPPGKGLEWIGEIYHSGSPDYNPSLKSRVTISV

DKSRNQFSLKLSSVTAADTAVYYCAKVSTGGFFDYWGQGTLVTVSSGGGGSGGGGSGGGGS

EIELTQSPSSLSASVGDRVTITCRASQSISSYLNWYQQKPGKAPKLLIYAASSLQSGVPSR

FSGSGSGTDFTLTISSLQPEDFATYYCQQSYSTPPTFGPGTKVEIK

SEQ ID NO.: 2
MKWVTFISLLFLFSSAYSQVQLVESGGGLVQPGGSLRLSCAASGLTFSSYNMGWFRQAPGQ

GLEAVASITWSGRDTFYADSVKGRFTISRDNSKNTLYLQMNSLRAEDTAVYYCAANPWPVA

APRSGTYWGQGTLVTVSSSGGGGSGGGGSGGGGSGGGGSGNWVNVISDLKKIEDLIQSMHI

DATLYTESDVHPSCKVTAMKCFLLELQVISLESGDASIHDTVENLIILANNSLSSNGNVTE

SGCKECEELEEKNIKEFLQSFVHIVQMFINTSGSTSGSGKPGSGEGSTKGQVQLQESGPGL

VKPSETLSLTCVVSGGSISSSNWWSWVRQPPGKGLEWIGEIYHSGSPDYNPSLKSRVTISV

DKSRNQFSLKLSSVTAADTAVYYCAKVSTGGFFDYWGQGTLVTVSSGGGGSGGGGSGGGGS
```

-continued

EIELTQSPSSLSASVGDRVTITCRASQSISSYLNWYQQKPGKAPKLLIYAASSLQSGVPSR
FSGSGSGTDFTLTISSLQPEDFATYYCQQSYSTPPTFGPGTKVEIKVDEHHHHHHHHHH

SEQ ID NO.: 3
VDEHHHHHHHHHH

SEQ ID NO.: 4
QVQLQESGPGLVKPSETLSLTCVVSGGSISSSNWWSWVRQPPGKGLEWIGEIYHSGSPDYN
PSLKSRVTISVDKSRNQFSLKLSSVTAADTAVYYCAKVSTGGFFDYWGQGTLVTVSSGGGG
SGGGGSGGGGSEIELTQSPSSLSASVGDRVTITCRASQSISSYLNWYQQKPGKAPKLLIYA
ASSLQSGVPSRFSGSGSGTDFTLTISSLQPEDFATYYCQQSYSTPPTFGPGTKVEIK

SEQ ID NO.: 5
atgaagtgggtaacctttattccttcttttctctttagctcggcttattcccaggtgc
agctggtggagtctggggaggcttggtgcagcctgggggctctctgagactctcctgtgc
agcctctggcctcaccttcagtagctataacatgggctggttccgccaggctccagggcaa
ggccttgaggctgtagcatctattacctggagtggtcgggacacattctatgcagactccg
tgaagggccgattcaccatctccagagacaactccaagaacactctctatctgcaaatgaa
cagcctgcgcgcggaggacacggccgtttattattgtgctgcaaaccccctggccagtggcg
gcgccacgtagtggcacctactggggccaagggaccctggtcaccgtctcctcatctggcg
gcggcggttctggtggaggaggtagtgggggggaggaagcggaggggtggctcagggaa
ctgggtgaatgtaataagtgatttgaaaaaaattgaagatcttattcaatctatgcatatt
gatgctactttatatacggaaagtgatgttcaccccagttgcaaagtaacagcaatgaagt
gctttctcttggagttacaagttatttcacttgagtccggagatgcaagtattcatgatac
agtagaaaatctgatcatcctagcaaacaacagtttgtcttctaatgggaatgtaacagaa
tctggatgcaaagaatgtgaggaactggaggaaaaaaatattaaagaattttgcagagtt
ttgtacatattgtccaaatgttcatcaacacttctggcagtaccagcgggtcagggaaacc
tggcagtggggaaggttccacaaaaggtcaagtacaactccaggagtccgggccagggttg
gtcaagccatccgagacgcttagtttgacctgtgttgtcagcggaggctctatatcatctt
caaactggtggtcttgggtacggcaaccaccgggcaaggggctcgaatggatcggggaaat
ctaccactccggaagccccgactataatccgtcactgaagagcagagtcactatatccgtg
gacaagagcagaaaccaattttctcttaagctctcctcagtgacagcagcagatacagcgg
tctattattgtgccaaggtatcaacaggcggattcttcgattattggggacagggcacttt
ggttacggtttcttctggaggcggggaagtggtggagggggtctggggaggtggctca
gaaatcgaacttacgcagtcaccctcctccctctcagcatccgtaggtgacagagttacga
taacctgtagagcaagtcaatccatttctagctaccttaactggtatcagcaaaaacctgg
gaaagcccccaagctgcttatctatgcggcatcctccctccaaagtggagttcccagtcgg
ttcagtggttccggctcagggactgactttaccctcacaatcagctcattgcaaccagagg
actttgcaacgtattactgtcagcaaagctactaacgccgcctacgttcggtcccggaac
caaagttgagattaaagtagacgaacaccatcatcatcatcaccatcaccaccattga SEQ ID NO.: 6
atgaagtgggtaacctttattccttcttttctctttagctcggcttattcccaggtgc
agctggtggagtctggggaggcttggtgcagcctgggggctctctgagactctcctgtgc
agcctctggcctcaccttcagtagctataacatgggctggttccgccaggctccagggcaa
ggccttgaggctgtagcatctattacctggagtggtcgggacacattctatgcagactccg

```
tgaagggccgattcaccatctccagagacaactccaagaacactctctatctgcaaatgaa cagcctgcgcgcggaggacacggccgtttattattgtgctgcaaacccctggccagtggcg gcgccacgtagtggcacctactggggccaagggaccctggtcaccgtctcctcatctggcg gcggcggttctggtggaggaggtagtgggggggaggaagcggaggggtggctcagggaa ctgggtgaatgtaataagtgatttgaaaaaaattgaagatcttattcaatctatgcatatt gatgctactttatatacggaaagtgatgttcaccccagttgcaaagtaacagcaatgaagt gctttctcttggagttacaagttatttcacttgagtccggagatgcaagtattcatgatac agtagaaaatctgatcatcctagcaaacaacagtttgtcttctaatgggaatgtaacagaa tctggatgcaaagaatgtgaggaactggaggaaaaaaatattaaagaattttttgcagagtt ttgtacatattgtccaaatgttcatcaacacttctggcagtaccagcgggtcagggaaacc tggcagtggggaaggttccacaaaaggtcaagtacaactccaggagtccgggccagggttg gtcaagccatccgagacgcttagtttgacctgtgttgtcagcggaggctctatatcatctt caaactggtggtcttgggtacggcaaccaccgggcaaggggctcgaatggatcggggaaat ctaccactccggaagccccgactataatccgtcactgaagagcagagtcactatatccgtg gacaagagcagaaaccaatttttctcttaagctctcctcagtgacagcagcagatacagcgg tctattattgtgccaaggtatcaacaggcggattcttcgattattggggacagggcacttt ggttacggtttcttctggaggcggggaagtggtggagggggtctggggaggtggctca gaaatcgaacttacgcagtcaccctcctccctctcagcatccgtaggtgacagagttacga taacctgtagagcaagtcaatccatttctagctaccttaactggtatcagcaaaaacctgg gaaagcccccaagctgcttatctatgcggcatcctccctccaaagtggagttcccagtcgg ttcagtggttccggctcagggactgactttaccctcacaatcagctcattgcaaccagagg actttgcaacgtattactgtcagcaaagctactcaacgccgcctacgttcggtcccggaac caaagttgagattaaatga
```

SEQ ID NO.: 7
```
caagtacaactccaggagtccgggccagggttggtcaagccatccgagacgcttagtttga cctgtgttgtcagcggaggctctatatcatcttcaaactggtggtcttgggtacggcaacc accgggcaaggggctcgaatggatcggggaaatctaccactccggaagccccgactataat ccgtcactgaagagcagagtcactatatccgtggacaagagcagaaaccaatttttctctta agctctcctcagtgacagcagcagatacagcggtctattattgtgccaaggtatcaacagg cggattcttcgattattggggacagggcactttggttacggtttcttctggaggcggggga agtggtggagggggtctggggaggtggctcagaaatcgaacttacgcagtcaccctcct ccctctcagcatccgtaggtgacagagttacgataacctgtagagcaagtcaatccatttc tagctaccttaactggtatcagcaaaaacctgggaaagcccccaagctgcttatctatgcg gcatcctccctccaaagtggagttcccagtcggttcagtggttccggctcagggactgact ttaccctcacaatcagctcattgcaaccagaggactttgcaacgtattactgtcagcaaag ctactcaacgccgcctacgttcggtcccggaaccaaagttgagattaaa
```

SEQ ID NO.: 8
```
QVQLVESGGGLVQPGGSLRLSCAASGLTFSSYNMGWFRQAPGQGLEAVASITWSGRDTFYA

DSVKGRFTISRDNSKNTLYLQMNSLRAEDTAVYYCAANPWPVAAPRSGTYWGQGTLVTVSS
```

SEQ ID NO.: 9
```
NWVNVISDLKKIEDLIQSMHIDATLYTESDVHPSCKVTAMKCFLLELQVISLESGDASIHD

TVENLIILANNSLSSNGNVTESGCKECEELEEKNIKEFLQSFVHIVQMFINTS
```

-continued

SEQ ID NO.: 10
MKWVTFISLLFLFSSAYS

SEQ ID NO.: 11
SGGGGSGGGGSGGGGSGGGGSG

SEQ ID NO.: 12
GSTSGSGKPGSGEGSTKG

SEQ ID NO.: 13
PSGQAGAAASESLFVSNHAY

SEQ ID NO.: 14
EASGGPE

SEQ ID NO.: 15
GGGGSGGGGS

SEQ ID NO.: 16
MGWSCIILFLVATATGVHSS

SEQ ID NO.: 17
MGWSCIILFLVATATGVHS

SEQ ID NO.: 18
EVQLVESGGELVQAGGSLRLSCAASGLTFSSYNMGWFRRAPGKEREFVASITWSGRDTFYADSVKGRFTISRDNAKNTVYLQMSSLKPEDTAVYYCAANPWPVAAPRSGTYWGQGTQVTVSSVDE

| SEQ ID NO. | Description |
| --- | --- |
| SEQ ID NO.: 1 | CLEC12A TriKE |
| SEQ ID NO.: 2 | CLEC12A TriKE with His tag and spacer |
| SEQ ID NO.: 3 | His tag and spacer |
| SEQ ID NO.: 4 | CLEC12A targeting domain |
| SEQ ID NO.: 5 | DNA encoding CLEC12A TriKE with His tag and spacer |
| SEQ ID NO.: 6 | DNA encoding CLEC12A TriKE |
| SEQ ID NO.: 7 | DNA encoding CLEC12A targeting domain |
| SEQ ID NO.: 8 | Humanized Cam16 |
| SEQ ID NO.: 9 | Wild-type IL-15 |
| SEQ ID NO.: 10 | Signal peptide |
| SEQ ID NO.: 11 | Linker |
| SEQ ID NO.: 12 | Linker |
| SEQ ID NO.: 13 | Linker |
| SEQ ID NO.: 14 | Linker |
| SEQ ID NO.: 15 | Linker |
| SEQ ID NO.: 16 | Signal peptide |
| SEQ ID NO.: 17 | Signal peptide |
| SEQ ID NO.: 18 | Non-humanized Cam16 |

Any and all references and citations to other documents, such as patents, patent applications, patent publications, journals, books, papers, web contents, that have been made throughout this disclosure are hereby incorporated herein by reference in their entirety for all purposes.

Although the present invention has been described with reference to specific details of certain embodiments thereof in the above examples, it will be understood that modifications and variations are encompassed within the spirit and scope of the invention. Accordingly, the invention is limited only by the following claims.

What is claimed is:

1. An isolated amino acid sequence comprising SEQ ID NO:1.

2. An isolated DNA sequence encoding the amino acid sequence of SEQ ID NO: 1.

3. An isolated amino acid sequence comprising SEQ ID NO:2.

4. An isolated DNA sequence encoding the amino acid sequence of SEQ ID NO:2.

5. A compound comprising:
   (i) a natural killer cell (NK) engaging domain;
   (ii) an NK activating domain operably linked to the NK engaging domain; and
   (iii) a targeting domain that selectively binds to a target cell and is operably linked to the NK activating domain and the NK engaging domain,
   wherein the compound has an amino acid sequence comprising SEQ ID NO: 1 or SEQ ID NO: 2.

6. A composition comprising:
   the compound of claim 5; and
   a pharmaceutically acceptable carrier.

7. A method comprising: administering to a subject the compound of claim 5 in an amount effective to induce NK-mediated killing of a target cell, wherein the target cell expresses CLEC12A.

8. The method of claim 7, wherein the target cell is a cancer cell.

9. A method for stimulating expansion of NK cells in vivo, the method comprising: administering to a subject an amount of the compound of claim 5 effective to stimulate expansion of NK cells in the subject.

10. A method of treating cancer in a subject, the method comprising: administering to the subject an amount of the compound of claim 5 effective for treating the cancer, wherein cells from the cancer express CLEC12A.

11. The method of claim 10, wherein the cancer comprises prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, or hematopoietic cancer.

12. The method of claim 11, further comprising administering the compound prior to, simultaneously with, or following chemotherapy, surgical resection of a tumor, or radiation therapy.

13. The method of claim 12, wherein the chemotherapy comprises altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine.

14. The method of claim 11, wherein the hematopoietic cancer is AML.

* * * * *

SEQUENCE LISTING

```
<160> NUMBER OF SEQ ID NOS: 18

<210> SEQ ID NO 1
<211> LENGTH: 534
<212> TYPE: PRT
<213> ORGANISM: Artificial Sequence
<220> FEATURE:
<223> OTHER INFORMATION: Synthetic

<400> SEQUENCE: 1

Met Lys Trp Val Thr Phe Ile Ser Leu Leu Phe Leu Phe Ser Ser Ala
1               5                   10                  15

Tyr Ser Gln Val Gln Leu Val Glu Ser Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Asn Met Gly Trp Phe Arg Gln Ala Pro Gly Gln Gly Leu Glu
    50                  55                  60
```

```
Ala Val Ala Ser Ile Thr Trp Ser Gly Arg Asp Thr Phe Tyr Ala Asp
 65              70                  75                  80

Ser Val Lys Gly Arg Phe Thr Ile Ser Arg Asp Asn Ser Lys Asn Thr
             85                  90                  95

Leu Tyr Leu Gln Met Asn Ser Leu Arg Ala Glu Asp Thr Ala Val Tyr
            100                 105                 110

Tyr Cys Ala Ala Asn Pro Trp Pro Val Ala Ala Pro Arg Ser Gly Thr
            115                 120                 125

Tyr Trp Gly Gln Gly Thr Leu Val Thr Val Ser Ser Ser Gly Gly Gly
            130                 135                 140

Gly Ser Gly Gly Gly Ser Gly Gly Gly Ser Gly Gly Gly Gly
145                 150                 155                 160

Ser Gly Asn Trp Val Asn Val Ile Ser Asp Leu Lys Lys Ile Glu Asp
                165                 170                 175

Leu Ile Gln Ser Met His Ile Asp Ala Thr Leu Tyr Thr Glu Ser Asp
            180                 185                 190

Val His Pro Ser Cys Lys Val Thr Ala Met Lys Cys Phe Leu Leu Glu
            195                 200                 205

Leu Gln Val Ile Ser Leu Glu Ser Gly Asp Ala Ser Ile His Asp Thr
210                 215                 220

Val Glu Asn Leu Ile Ile Leu Ala Asn Asn Ser Leu Ser Ser Asn Gly
225                 230                 235                 240

Asn Val Thr Glu Ser Gly Cys Lys Glu Cys Glu Glu Leu Glu Glu Lys
                245                 250                 255

Asn Ile Lys Glu Phe Leu Gln Ser Phe Val His Ile Val Gln Met Phe
            260                 265                 270

Ile Asn Thr Ser Gly Ser Thr Ser Gly Ser Gly Lys Pro Gly Ser Gly
            275                 280                 285

Glu Gly Ser Thr Lys Gly Gln Val Gln Leu Gln Glu Ser Gly Pro Gly
290                 295                 300

Leu Val Lys Pro Ser Glu Thr Leu Ser Leu Thr Cys Val Val Ser Gly
305                 310                 315                 320

Gly Ser Ile Ser Ser Ser Asn Trp Trp Ser Trp Val Arg Gln Pro Pro
                325                 330                 335

Gly Lys Gly Leu Glu Trp Ile Gly Glu Ile Tyr His Ser Gly Ser Pro
            340                 345                 350

Asp Tyr Asn Pro Ser Leu Lys Ser Arg Val Thr Ile Ser Val Asp Lys
            355                 360                 365

Ser Arg Asn Gln Phe Ser Leu Lys Leu Ser Ser Val Thr Ala Ala Asp
            370                 375                 380

Thr Ala Val Tyr Tyr Cys Ala Lys Val Ser Thr Gly Gly Phe Phe Asp
385                 390                 395                 400

Tyr Trp Gly Gln Gly Thr Leu Val Thr Val Ser Ser Gly Gly Gly Gly
                405                 410                 415

Ser Gly Gly Gly Gly Ser Gly Gly Gly Ser Glu Ile Glu Leu Thr
            420                 425                 430

Gln Ser Pro Ser Ser Leu Ser Ala Ser Val Gly Asp Arg Val Thr Ile
            435                 440                 445

Thr Cys Arg Ala Ser Gln Ser Ile Ser Ser Tyr Leu Asn Trp Tyr Gln
            450                 455                 460

Gln Lys Pro Gly Lys Ala Pro Lys Leu Leu Ile Tyr Ala Ala Ser Ser
465                 470                 475                 480
```

```
Leu Gln Ser Gly Val Pro Ser Arg Phe Ser Gly Ser Gly Ser Gly Thr
                485                 490                 495

Asp Phe Thr Leu Thr Ile Ser Ser Leu Gln Pro Glu Asp Phe Ala Thr
            500                 505                 510

Tyr Tyr Cys Gln Gln Ser Tyr Ser Thr Pro Pro Thr Phe Gly Pro Gly
        515                 520                 525

Thr Lys Val Glu Ile Lys
        530

<210> SEQ ID NO 2
<211> LENGTH: 547
<212> TYPE: PRT
<213> ORGANISM: Artificial Sequence
<220> FEATURE:
<223> OTHER INFORMATION: Synthetic

<400> SEQUENCE: 2

Met Lys Trp Val Thr Phe Ile Ser Leu Leu Phe Leu Phe Ser Ser Ala
1               5                   10                  15

Tyr Ser Gln Val Gln Leu Val Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Asn Met Gly Trp Phe Arg Gln Ala Pro Gly Gln Gly Leu Glu
    50                  55                  60

Ala Val Ala Ser Ile Thr Trp Ser Gly Arg Asp Thr Phe Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Ala Asn Pro Trp Pro Val Ala Ala Pro Arg Ser Gly Thr
        115                 120                 125

Tyr Trp Gly Gln Gly Thr Leu Val Thr Val Ser Ser Gly Gly Gly Gly
    130                 135                 140

Gly Ser Gly Gly Gly Ser Gly Gly Gly Ser Gly Gly Gly Gly
145                 150                 155                 160

Ser Gly Asn Trp Val Asn Val Ile Ser Asp Leu Lys Lys Ile Glu Asp
                165                 170                 175

Leu Ile Gln Ser Met His Ile Asp Ala Thr Leu Tyr Thr Glu Ser Asp
            180                 185                 190

Val His Pro Ser Cys Lys Val Thr Ala Met Lys Cys Phe Leu Leu Glu
        195                 200                 205

Leu Gln Val Ile Ser Leu Glu Ser Gly Asp Ala Ser Ile His Asp Thr
    210                 215                 220

Val Glu Asn Leu Ile Ile Leu Ala Asn Asn Ser Leu Ser Ser Asn Gly
225                 230                 235                 240

Asn Val Thr Glu Ser Gly Cys Lys Glu Cys Glu Glu Leu Glu Glu Lys
                245                 250                 255

Asn Ile Lys Glu Phe Leu Gln Ser Phe Val His Ile Val Gln Met Phe
            260                 265                 270

Ile Asn Thr Ser Gly Ser Thr Ser Gly Ser Gly Lys Pro Gly Ser Gly
        275                 280                 285

Glu Gly Ser Thr Lys Gly Gln Val Gln Leu Gln Glu Ser Gly Pro Gly
    290                 295                 300
```

```
Leu Val Lys Pro Ser Glu Thr Leu Ser Leu Thr Cys Val Val Ser Gly
305                 310                 315                 320

Gly Ser Ile Ser Ser Asn Trp Trp Ser Trp Val Arg Gln Pro Pro
            325                 330                 335

Gly Lys Gly Leu Glu Trp Ile Gly Glu Ile Tyr His Ser Gly Ser Pro
                340                 345                 350

Asp Tyr Asn Pro Ser Leu Lys Ser Arg Val Thr Ile Ser Val Asp Lys
            355                 360                 365

Ser Arg Asn Gln Phe Ser Leu Lys Leu Ser Ser Val Thr Ala Ala Asp
        370                 375                 380

Thr Ala Val Tyr Tyr Cys Ala Lys Val Ser Thr Gly Gly Phe Phe Asp
385                 390                 395                 400

Tyr Trp Gly Gln Gly Thr Leu Val Thr Val Ser Ser Gly Gly Gly
                405                 410                 415

Ser Gly Gly Gly Gly Ser Gly Gly Gly Ser Glu Ile Glu Leu Thr
            420                 425                 430

Gln Ser Pro Ser Ser Leu Ser Ala Ser Val Gly Asp Arg Val Thr Ile
            435                 440                 445

Thr Cys Arg Ala Ser Gln Ser Ile Ser Ser Tyr Leu Asn Trp Tyr Gln
450                 455                 460

Gln Lys Pro Gly Lys Ala Pro Lys Leu Leu Ile Tyr Ala Ala Ser Ser
465                 470                 475                 480

Leu Gln Ser Gly Val Pro Ser Arg Phe Ser Gly Ser Gly Ser Gly Thr
                485                 490                 495

Asp Phe Thr Leu Thr Ile Ser Ser Leu Gln Pro Glu Asp Phe Ala Thr
            500                 505                 510

Tyr Tyr Cys Gln Gln Ser Tyr Ser Thr Pro Pro Thr Phe Gly Pro Gly
            515                 520                 525

Thr Lys Val Glu Ile Lys Val Asp Glu His His His His His His
        530                 535                 540

His His His
545

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Val Asp Glu His His His His His His His His His
1               5                   10

<210> SEQ ID NO 4
<211> LENGTH: 240
<212> TYPE: PRT
<213> ORGANISM: Artificial Sequence
<220> FEATURE:
<223> OTHER INFORMATION: Synthetic

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser
            20                  25                  30

Asn Trp Trp Ser Trp Val Arg Gln Pro Pro Gly Lys Gly Leu Glu Trp
            35                  40                  45
```

```
Ile Gly Glu Ile Tyr His Ser Gly Ser Pro Asp Tyr Asn Pro Ser Leu
 50                  55                  60
Lys Ser Arg Val Thr Ile Ser Val Asp Lys Ser Arg Asn Gln Phe Ser
 65                  70                  75                  80
Leu Lys Leu Ser Ser Val Thr Ala Ala Asp Thr Ala Val Tyr Tyr Cys
                 85                  90                  95
Ala Lys Val Ser Thr Gly Gly Phe Phe Asp Tyr Trp Gly Gln Gly Thr
                100                 105                 110
Leu Val Thr Val Ser Ser Gly Gly Gly Gly Ser Gly Gly Gly Gly Ser
            115                 120                 125
Gly Gly Gly Gly Ser Glu Ile Glu Leu Thr Gln Ser Pro Ser Ser Leu
        130                 135                 140
Ser Ala Ser Val Gly Asp Arg Val Thr Ile Thr Cys Arg Ala Ser Gln
145                 150                 155                 160
Ser Ile Ser Ser Tyr Leu Asn Trp Tyr Gln Gln Lys Pro Gly Lys Ala
                165                 170                 175
Pro Lys Leu Leu Ile Tyr Ala Ala Ser Ser Leu Gln Ser Gly Val Pro
                180                 185                 190
Ser Arg Phe Ser Gly Ser Gly Ser Gly Thr Asp Phe Thr Leu Thr Ile
            195                 200                 205
Ser Ser Leu Gln Pro Glu Asp Phe Ala Thr Tyr Tyr Cys Gln Gln Ser
        210                 215                 220
Tyr Ser Thr Pro Pro Thr Phe Gly Pro Gly Thr Lys Val Glu Ile Lys
225                 230                 235                 240

<210> SEQ ID NO 5
<211> LENGTH: 1644
<212> TYPE: DNA
<213> ORGANISM: Artificial Sequence
<220> FEATURE:
<223> OTHER INFORMATION: Synthetic

<400> SEQUENCE: 5
atgaagtggg taacctttat ttcccttctt tttctcttta gctcggctta ttcccaggtg      60
cagctggtgg agtctggggg aggcttggtg cagcctgggg gctctctgag actctcctgt    120
gcagcctctg gcctcacctt cagtagctat aacatgggct ggttccgcca ggctccaggg    180
caaggccttg aggctgtagc atctattacc tggagtggtc gggacacatt ctatgcagac    240
tccgtgaagg gccgattcac catctccaga gacaactcca agaacactct ctatctgcaa    300
atgaacagcc tgcgcgcgga ggacacggcc gtttattatt gtgctgcaaa cccctggcca    360
gtggcggcgc cacgtagtgg cacctactgg ggccaaggga ccctggtcac cgtctcctca    420
tctggcggcg gcggttctgg tggaggaggt agtgggggga gaggaagcgg aggggtggc    480
tcagggaact gggtgaatgt aataagtgat tgaaaaaaaa ttgaagatct tattcaatct    540
atgcatattg atgctacttt atatacggaa agtgatgttc accccagttg caaagtaaca    600
gcaatgaagt gctttctctt ggagttacaa gttatttcac ttgagtccgg agatgcaagt    660
attcatgata cagtagaaaa tctgatcatc ctagcaaaca acagtttgtc ttctaatggg    720
aatgtaacag aatctggatg caaagaatgt gaggaactgg aggaaaaaaa tattaaagaa    780
tttttgcaga gttttgtaca tattgtccaa atgttcatca cacttctgg cagtaccagc    840
gggtcaggga aacctggcag tggggaaggt tccacaaaag gtcaagtaca actccaggag    900
tccgggccag ggttggtcaa gccatccgag acgcttagtt tgacctgtgt tgtcagcgga    960
```

| | |
|---|---|
| ggctctatat catcttcaaa ctggtggtct tgggtacggc aaccaccggg caaggggctc | 1020 |
| gaatggatcg gggaaatcta ccactccgga agccccgact ataatccgtc actgaagagc | 1080 |
| agagtcacta tatccgtgga caagagcaga aaccaatttt ctcttaagct ctcctcagtg | 1140 |
| acagcagcag atacagcggt ctattattgt gccaaggtat caacaggcgg attcttcgat | 1200 |
| tattggggac agggcacttt ggttacggtt tcttctggag gcggggaag tggtggaggg | 1260 |
| gggtctgggg gaggtggctc agaaatcgaa cttacgcagt caccctcctc cctctcagca | 1320 |
| tccgtaggtg acagagttac gataacctgt agagcaagtc aatccatttc tagctacctt | 1380 |
| aactggtatc agcaaaaacc tgggaaagcc cccaagctgc ttatctatgc ggcatcctcc | 1440 |
| ctccaaagtg gagttcccag tcggttcagt ggttccggct cagggactga ctttacccctc | 1500 |
| acaatcagct cattgcaacc agaggacttt gcaacgtatt actgtcagca aagctactca | 1560 |
| acgccgccta cgttcggtcc cggaaccaaa gttgagatta agtagacga acaccatcat | 1620 |
| catcatcacc atcaccacca ttga | 1644 |

<210> SEQ ID NO 6
<211> LENGTH: 1605
<212> TYPE: DNA
<213> ORGANISM: Artificial Sequence
<220> FEATURE:
<223> OTHER INFORMATION: Synthetic

<400> SEQUENCE: 6

| | |
|---|---|
| atgaagtggg taacctttat ttcccttctt tttctcttta gctcggctta ttcccaggtg | 60 |
| cagctggtgg agtctggggg aggcttggtg cagcctgggg gctctctgag actcctgtgt | 120 |
| gcagcctctg gcctcacctt cagtagctat aacatgggct ggttccgcca ggctccaggg | 180 |
| caaggccttg aggctgtagc atctattacc tggagtggtc gggacacatt ctatgcagac | 240 |
| tccgtgaagg gccgattcac catctcccaga dacaactcca gaacactct ctatctgcaa | 300 |
| atgaacagcc tgcgcgcgga ggacacggcc gtttattatt gtgctgcaaa ccccctggcca | 360 |
| gtggcggcgc cacgtagtgg cacctactgg ggccaaggga ccctggtcac cgtctcctca | 420 |
| tctggcggcg gcggttctgg tggaggaggt agtgggggg gaggaagcgg aggggggtggc | 480 |
| tcagggaact gggtgaatgt aataagtgat ttgaaaaaaa ttgaagatct tattcaatct | 540 |
| atgcatattg atgctacttt atatacggaa agtgatgttc accccagttg caaagtaaca | 600 |
| gcaatgaagt gctttctctt ggagttacaa gttatttcac ttgagtccgg agatgcaagt | 660 |
| attcatgata cagtagaaaa tctgatcatc ctagcaaaca acagtttgtc ttctaatggg | 720 |
| aatgtaacag aatctggatg caaagaatgt gaggaactgg aggaaaaaaa tattaaagaa | 780 |
| ttttttgcaga gttttgtaca tattgtccaa atgttcatca acacttctgg cagtaccagc | 840 |
| gggtcaggga aacctggcag tggggaaggt tccacaaaag gtcaagtaca actccaggag | 900 |
| tccgggccag ggttggtcaa gccatccgag acgcttagtt tgacctgtgt tgtcagcgga | 960 |
| ggctctatat catcttcaaa ctggtggtct tgggtacggc aaccaccggg caaggggctc | 1020 |
| gaatggatcg gggaaatcta ccactccgga agccccgact ataatccgtc actgaagagc | 1080 |
| agagtcacta tatccgtgga caagagcaga accaattttt ctcttaagct ctcctcagtg | 1140 |
| acagcagcag atacagcggt ctattattgt gccaaggtat caacaggcgg attcttcgat | 1200 |
| tattggggac agggcacttt ggttacggtt tcttctggag gcggggaag tggtggaggg | 1260 |
| gggtctgggg gaggtggctc agaaatcgaa cttacgcagt caccctcctc cctctcagca | 1320 |
| tccgtaggtg acagagttac gataacctgt agagcaagtc aatccatttc tagctacctt | 1380 |

```
aactggtatc agcaaaaacc tgggaaagcc cccaagctgc ttatctatgc ggcatcctcc    1440
ctccaaagtg gagttcccag tcggttcagt ggttccggct cagggactga ctttacccctc   1500 acaatcagct cattgcaacc agaggacttt gcaacgtatt actgtcagca aagctactca    1560
acgccgccta cgttcggtcc cggaaccaaa gttgagatta aatga                    1605
```

<210> SEQ ID NO 7
<211> LENGTH: 720
<212> TYPE: DNA
<213> ORGANISM: Artificial Sequence
<220> FEATURE:
<223> OTHER INFORMATION: Synthetic

<400> SEQUENCE: 7

```
caagtacaac tccaggagtc cgggccaggg ttggtcaagc catccgagac gcttagtttg      60
acctgtgttg tcagcggagg ctctatatca tcttcaaact ggtggtcttg ggtacggcaa    120
ccaccgggca aggggctcga atggatcggg gaaatctacc actccggaag ccccgactat    180
aatccgtcac tgaagagcag agtcactata tccgtggaca gagcagaaa ccaattttct     240 cttaagctct cctcagtgac agcagcagat acagcggtct attattgtgc caaggtatca    300
acaggcggat tcttcgatta ttggggacag ggcactttgg ttacggtttc ttctggaggc    360 ggggaagtg gtggagggg gtctggggga ggtggctcag aaatcgaact tacgcagtca      420
ccctcctccc tctcagcatc cgtaggtgac agagttacga taacctgtag agcaagtcaa    480
tccatttcta gctaccttaa ctggtatcag caaaaacctg ggaaagcccc caagctgctt    540
atctatgcgg catcctccct ccaaagtgga gttcccagtc ggttcagtgg ttccggctca    600
gggactgact ttaccctcac aatcagctca ttgcaaccag aggactttgc aacgtattac    660
tgtcagcaaa gctactcaac gccgcctacg ttcggtcccg aaccaaagt tgagattaaa     720
```

<210> SEQ ID NO 8
<211> LENGTH: 122
<212> TYPE: PRT
<213> ORGANISM: Artificial Sequence
<220> FEATURE:
<223> OTHER INFORMATION: Synthetic

<400> SEQUENCE: 8

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Asn Met Gly Trp Phe Arg Gln Ala Pro Gly Gln Gly Leu Glu Ala Val
        35                  40                  45

Ala Ser Ile Thr Trp Ser Gly Arg Asp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Leu Val Thr Val Ser Ser
        115                 120
```

<210> SEQ ID NO 9

<211> LENGTH: 114
<212> TYPE: PRT
<213> ORGANISM: Artificial Sequence
<220> FEATURE:
<223> OTHER INFORMATION: Synthetic

<400> SEQUENCE: 9

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
Val Ile Ser Leu Glu Ser Gly Asp Ala Ser Ile His Asp Thr Val Glu
    50                  55                  60
Asn Leu Ile Ile Leu Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Met Lys Trp Val Thr Phe Ile Ser Leu Leu Phe Leu Phe Ser Ser Ala
1               5                   10                  15
Tyr Ser

<210> SEQ ID NO 11
<211> LENGTH: 22
<212> TYPE: PRT
<213> ORGANISM: Artificial Sequence
<220> FEATURE:
<223> OTHER INFORMATION: Synthetic

<400> SEQUENCE: 11

Ser Gly Gly Gly Gly Ser Gly Gly Gly Ser Gly Gly Gly Gly Ser
1               5                   10                  15
Gly Gly Gly Gly Ser Gly
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic

<400> SEQUENCE: 12

Gly Ser Thr Ser Gly Ser Gly Lys Pro Gly Ser Gly Glu Gly Ser Thr
1               5                   10                  15
Lys Gly

<210> SEQ ID NO 13

```
<211> LENGTH: 20
<212> TYPE: PRT
<213> ORGANISM: Artificial Sequence
<220> FEATURE:
<223> OTHER INFORMATION: Synthetic

<400> SEQUENCE: 13

Pro Ser Gly Gln Ala Gly Ala Ala Ala Ser Glu Ser Leu Phe Val Ser
1               5                   10                  15

Asn His Ala Tyr
            20

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Glu Ala Ser Gly Gly Pro Glu
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Gly Gly Gly Gly Ser Gly Gly Gly Gly Ser
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Synthetic

<400> SEQUENCE: 16

Met Gly Trp Ser Cys Ile Ile Leu Phe Leu Val Ala Thr Ala Thr Gly
1               5                   10                  15

Val His Ser Ser
            20

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Met Gly Trp Ser Cys Ile Ile Leu Phe Leu Val Ala Thr Ala Thr Gly
1               5                   10                  15

Val His Ser

<210> SEQ ID NO 18
<211> LENGTH: 125
<212> TYPE: PRT
<213> ORGANISM: Artificial Sequence
<220> FEATURE:
<223> OTHER INFORMATION: Synthetic
```

```
<400> SEQUENCE: 18

Glu Val Gln Leu Val Glu Ser Gly Gly Glu Leu Val Gln Ala Gly Gly
1               5                   10                  15

Ser Leu Arg Leu Ser Cys Ala Ala Ser Gly Leu Thr Phe Ser Ser Tyr
            20                  25                  30

Asn Met Gly Trp Phe Arg Arg Ala Pro Gly Lys Glu Arg Glu Phe Val
        35                  40                  45

Ala Ser Ile Thr Trp Ser Gly Arg Asp Thr Phe Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Gln Val Thr Val Ser Ser Val Asp Glu
            115                 120                 125
```